(12) United States Patent
Hollis et al.

(10) Patent No.: US 11,109,902 B2
(45) Date of Patent: Sep. 7, 2021

(54) BONE PLATES WITH DYNAMIC ELEMENTS

(71) Applicant: Crossroads Extremity Systems, LLC, Memphis, TN (US)

(72) Inventors: Michael Chad Hollis, Collierville, TN (US); Vernon Raymond Hartdegen, Collierville, TN (US); Daniel Sayger, Southaven, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 0 days.

(21) Appl. No.: 17/001,371

(22) Filed: Aug. 24, 2020

(65) Prior Publication Data

US 2020/0383711 A1 Dec. 10, 2020

Related U.S. Application Data

(63) Continuation of application No. 16/595,303, filed on Oct. 7, 2019, which is a continuation of application No. 16/368,794, filed on Mar. 28, 2019, now Pat. No. 10,433,888, which is a continuation of application No. 15/209,623, filed on Jul. 13, 2016, now Pat. No. 10,299,842, which is a continuation-in-part of (Continued)

(51) Int. Cl.
| | |
|---|---|
| *A61B 17/80* | (2006.01) |
| *A61B 17/064* | (2006.01) |
| *A61B 17/17* | (2006.01) |
| *A61B 17/84* | (2006.01) |
| *A61B 17/86* | (2006.01) |
| *A61B 17/88* | (2006.01) |

(52) U.S. Cl.
CPC ...... *A61B 17/8085* (2013.01); *A61B 17/0642* (2013.01); *A61B 17/1728* (2013.01); *A61B 17/809* (2013.01); *A61B 17/8042* (2013.01); *A61B 17/8057* (2013.01); *A61B 17/8061* (2013.01); *A61B 17/84* (2013.01); *A61B 17/846* (2013.01); *A61B 17/848* (2013.01); *A61B 17/8605* (2013.01); *A61B 17/8625* (2013.01); *A61B 17/888* (2013.01); *A61B 17/8863* (2013.01); *A61B 17/8888* (2013.01); *A61B 17/863* (2013.01)

(58) Field of Classification Search
CPC .......................................... A61B 17/80–8095
See application file for complete search history.

(56) References Cited

U.S. PATENT DOCUMENTS

| | | |
|---|---|---|
| 2,010,913 A | 8/1935 | Bruce |
| 2,544,492 A | 3/1951 | Downing |

(Continued)

FOREIGN PATENT DOCUMENTS

| | | |
|---|---|---|
| CA | 2063484 | 9/1993 |
| CN | 2404495 | 11/2000 |

(Continued)

*Primary Examiner* — Zade Coley
(74) *Attorney, Agent, or Firm* — Knobbe Martens Olson & Bear, LLP

(57) ABSTRACT

Bone fixation systems include various combinations of stabilizing members, dynamic elements, fasteners, and locking mechanisms. Bone plates receive dynamic bone staples and bone screws. Other dynamic elements include elbow pegs, straight pegs, and wire pegs.

19 Claims, 59 Drawing Sheets

Related U.S. Application Data application No. PCT/US2014/070495, filed on Dec. 16, 2014, and a continuation-in-part of application No. PCT/US2015/039551, filed on Jul. 8, 2015, and a continuation-in-part of application No. PCT/US2015/039556, filed on Jul. 8, 2015.

(60) Provisional application No. 62/192,059, filed on Jul. 13, 2015, provisional application No. 61/919,069, filed on Dec. 20, 2013, provisional application No. 62/022,811, filed on Jul. 10, 2014, provisional application No. 62/036,240, filed on Aug. 12, 2014.

(56) References Cited

U.S. PATENT DOCUMENTS

| | | |
|---|---|---|
| 3,741,205 A | 6/1973 | Markolf |
| 4,263,903 A | 4/1981 | Griggs |
| 4,278,091 A * | 7/1981 | Borzone ............ A61B 17/0642 411/469 |
| 4,415,111 A | 11/1983 | McHarrie |
| 4,438,769 A | 3/1984 | Pratt |
| 4,454,875 A | 6/1984 | Pratt |
| 4,484,570 A | 11/1984 | Sutter |
| 4,655,222 A | 4/1987 | Florez |
| 4,805,617 A * | 2/1989 | Bedi ................ A61B 17/0643 606/220 |
| 4,852,558 A | 8/1989 | Outerbridge |
| 5,013,315 A * | 5/1991 | Barrows ................ A61B 17/80 606/71 |
| 5,044,540 A | 9/1991 | Dulebohn |
| 5,209,756 A | 5/1993 | Seedhom |
| 5,246,443 A | 9/1993 | Mai |
| 5,258,012 A | 11/1993 | Luscombe |
| 5,352,229 A | 10/1994 | Goble |
| 5,395,372 A | 3/1995 | Holt |
| 5,449,359 A | 9/1995 | Groiso |
| 5,454,814 A | 10/1995 | Comte |
| 5,490,409 A | 2/1996 | Weber |
| 5,498,749 A | 3/1996 | Heise |
| 5,520,700 A | 5/1996 | Beyar |
| 5,578,034 A | 11/1996 | Estes |
| 5,607,425 A | 3/1997 | Rogozinski |
| 5,628,740 A | 5/1997 | Mullane |
| 5,634,926 A | 6/1997 | Jobe |
| 5,660,188 A | 8/1997 | Groiso |
| 5,662,655 A * | 9/1997 | Laboureau ......... A61B 17/0642 606/75 |
| 5,716,357 A | 2/1998 | Rogozinski |
| 5,749,564 A | 5/1998 | Malek |
| 5,779,707 A | 7/1998 | Bertholet |
| 5,785,713 A * | 7/1998 | Jobe ................ A61B 17/0401 606/75 |
| 5,788,698 A | 8/1998 | Savornin |
| 5,807,403 A | 9/1998 | Beyar |
| 5,853,414 A | 12/1998 | Groiso |
| 5,904,682 A | 5/1999 | Rogozinski |
| 5,931,839 A * | 8/1999 | Medoff .............. A61B 17/8061 606/286 |
| 5,947,968 A | 9/1999 | Rogozinski |
| 5,947,999 A | 9/1999 | Groiso |
| 5,972,000 A | 10/1999 | Beyar |
| 5,993,476 A | 11/1999 | Groiso |
| 6,010,504 A | 1/2000 | Rogozinski |
| 6,017,343 A | 1/2000 | Rogozinski |
| 6,019,759 A | 2/2000 | Rogozinski |
| 6,059,787 A | 5/2000 | Allen |
| 6,089,435 A | 7/2000 | Malek |
| 6,105,936 A | 8/2000 | Malek |
| 6,179,840 B1 | 1/2001 | Bowman |
| 6,187,009 B1 | 2/2001 | Herzog |
| 6,281,262 B1 | 8/2001 | Shikinami |
| 6,322,562 B1 | 11/2001 | Wolter |
| 6,325,805 B1 * | 12/2001 | Ogilvie ................ A61B 17/70 606/75 |
| 6,334,446 B1 | 1/2002 | Beyar |
| 6,336,927 B2 | 1/2002 | Rogozinski |
| 6,348,054 B1 | 2/2002 | Allen |
| 6,364,884 B1 | 4/2002 | Bowman |
| 6,379,354 B1 | 4/2002 | Rogozinski |
| 6,387,041 B1 | 5/2002 | Harari |
| 6,402,765 B1 | 6/2002 | Monassevitch |
| 6,402,766 B2 | 6/2002 | Bowman |
| 6,406,480 B1 | 6/2002 | Beyar |
| 6,423,073 B2 | 7/2002 | Bowman |
| 6,436,110 B2 | 8/2002 | Bowman |
| 6,447,517 B1 | 9/2002 | Bowman |
| 6,497,707 B1 | 12/2002 | Bowman |
| 6,544,273 B1 | 4/2003 | Harari |
| 6,575,984 B2 | 6/2003 | Beyar |
| 6,575,998 B2 | 6/2003 | Beyar |
| 6,582,435 B2 | 6/2003 | Wellisz |
| 6,592,610 B2 | 7/2003 | Beyar |
| 6,635,058 B2 | 10/2003 | Beyar |
| 6,652,531 B2 | 11/2003 | Wellisz |
| 6,663,642 B2 | 12/2003 | Beyar |
| 6,679,885 B2 | 1/2004 | Wellisz |
| 6,709,437 B2 | 3/2004 | Wellisz |
| 6,730,110 B1 | 5/2004 | Harari |
| 6,746,455 B2 | 6/2004 | Beyar |
| 6,783,531 B2 | 8/2004 | Allen |
| 6,896,684 B2 | 5/2005 | Monassevitch |
| 6,966,911 B2 | 11/2005 | Groiso |
| 6,974,461 B1 | 12/2005 | Wolter |
| 7,090,676 B2 | 8/2006 | Huebner |
| 7,147,640 B2 | 12/2006 | Huebner |
| 7,153,309 B2 | 12/2006 | Huebner |
| 7,179,260 B2 | 2/2007 | Gerlach |
| 7,189,237 B2 | 3/2007 | Huebner |
| 7,214,232 B2 | 5/2007 | Bowman |
| 7,226,408 B2 | 6/2007 | Harai |
| 7,229,452 B2 | 6/2007 | Kayan |
| 7,235,079 B2 | 6/2007 | Jensen |
| 7,250,054 B2 | 7/2007 | Allen |
| 7,255,701 B2 | 8/2007 | Allen |
| 7,311,712 B2 | 12/2007 | Dalton |
| 7,326,212 B2 | 2/2008 | Huebner |
| 7,438,209 B1 | 10/2008 | Hess |
| 7,473,257 B2 | 1/2009 | Knopfle |
| 7,500,979 B2 | 3/2009 | Hueil |
| 7,506,791 B2 | 3/2009 | Omaits |
| 7,537,596 B2 | 5/2009 | Jensen |
| 7,537,603 B2 | 5/2009 | Huebner |
| 7,537,604 B2 | 5/2009 | Huebner |
| 7,556,647 B2 | 7/2009 | Drews |
| 7,578,825 B2 | 8/2009 | Huebner |
| 7,604,151 B2 | 10/2009 | Hess |
| 7,618,441 B2 | 11/2009 | Groiso |
| 7,651,498 B2 | 1/2010 | Shifrin |
| 7,665,647 B2 | 2/2010 | Shelton |
| 7,669,746 B2 | 3/2010 | Shelton |
| 7,669,747 B2 | 3/2010 | Weisenburgh |
| 7,673,781 B2 | 3/2010 | Swayze |
| 7,673,782 B2 | 3/2010 | Hess |
| 7,704,251 B2 | 4/2010 | Huebner |
| 7,704,279 B2 | 4/2010 | Moskowitz |
| 7,717,945 B2 | 5/2010 | Jensen |
| 7,735,703 B2 | 6/2010 | Morgan |
| 7,740,634 B2 | 6/2010 | Orbay |
| 7,766,209 B2 | 8/2010 | Baxter |
| 7,766,948 B1 | 8/2010 | Leung |
| 7,771,433 B2 | 8/2010 | Orbay |
| 7,794,475 B2 | 9/2010 | Hess |
| 7,832,612 B2 | 11/2010 | Baxter |
| 7,846,188 B2 | 12/2010 | Moskowitz |
| 7,857,186 B2 | 12/2010 | Baxter |
| 7,857,836 B2 | 12/2010 | Huebner |
| 7,905,381 B2 | 3/2011 | Baxter |
| 7,905,910 B2 | 3/2011 | Gerlach |
| 7,909,858 B2 | 3/2011 | Gerlach |
| 7,914,532 B2 | 3/2011 | Shaver |
| 7,918,879 B2 | 4/2011 | Yeung |
| 7,927,332 B2 | 4/2011 | Huebner |
| 7,934,630 B2 | 5/2011 | Shelton |

(56) References Cited

U.S. PATENT DOCUMENTS

| | | |
|---|---|---|
| 7,935,126 B2 | 5/2011 | Orbay |
| 7,942,903 B2 | 5/2011 | Moskowitz |
| 7,951,180 B2 | 5/2011 | Moskowitz |
| 7,954,686 B2 | 6/2011 | Baxter |
| 7,955,388 B2 | 6/2011 | Jensen |
| 7,963,982 B2 | 6/2011 | Kirschman |
| 7,966,799 B2 | 6/2011 | Morgan |
| 7,972,363 B2 | 7/2011 | Moskowitz |
| 8,016,867 B2 | 9/2011 | Bowman |
| 8,043,346 B2 | 10/2011 | Markworth |
| 8,100,953 B2 | 1/2012 | White |
| 8,105,367 B2 | 1/2012 | Austin |
| 8,114,139 B2 | 2/2012 | Sournac |
| 8,137,351 B2 | 3/2012 | Prandi |
| 8,141,762 B2 | 3/2012 | Bedi |
| 8,172,886 B2 | 5/2012 | Castaneda |
| 8,177,819 B2 | 5/2012 | Huebner |
| 8,186,560 B2 | 5/2012 | Hess |
| 8,205,781 B2 | 6/2012 | Baxter |
| 8,220,690 B2 | 7/2012 | Hess |
| 8,231,627 B2 | 7/2012 | Huebner |
| 8,231,662 B2 | 7/2012 | Huebner |
| 8,241,326 B2 | 8/2012 | Harari |
| 8,241,338 B2 | 8/2012 | Castaneda |
| 8,252,032 B2 | 8/2012 | White |
| 8,257,370 B2 | 9/2012 | Moskowitz |
| 8,262,711 B2 | 9/2012 | Hess |
| 8,317,070 B2 | 11/2012 | Hueil |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton |
| 8,365,976 B2 | 2/2013 | Hess |
| 8,382,807 B2 | 2/2013 | Austin |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton |
| 8,475,504 B2 | 7/2013 | Gillard |
| 8,485,412 B2 | 7/2013 | Shelton |
| 8,486,116 B2 | 7/2013 | Heilman |
| 8,496,693 B2 | 7/2013 | Robinson |
| 8,499,993 B2 | 8/2013 | Shelton |
| 8,518,090 B2 | 8/2013 | Huebner |
| 8,523,919 B2 | 9/2013 | Huebner |
| 8,540,129 B2 | 9/2013 | Baxter |
| 8,540,133 B2 | 9/2013 | Bedi |
| 8,545,540 B2 | 10/2013 | Castaneda |
| 8,561,870 B2 | 10/2013 | Baxter |
| 8,567,656 B2 | 10/2013 | Shelton |
| 8,574,270 B2 | 11/2013 | Hess |
| 8,584,853 B2 | 11/2013 | Knight |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinman |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton |
| 8,808,325 B2 | 8/2014 | Hess |
| 8,814,915 B2 | 8/2014 | Hess |
| 8,834,537 B2 | 9/2014 | Castaneda |
| 8,858,562 B2 | 10/2014 | Orbay |
| 8,882,812 B2 | 11/2014 | Hess |
| 8,888,824 B2 | 11/2014 | Austin |
| 8,888,826 B2 | 11/2014 | Kinman |
| 8,894,651 B2 | 11/2014 | Aflatoon |
| 8,899,465 B2 | 12/2014 | Shelton |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 | 8/2015 | Taylor |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,204,932 B2 | 12/2015 | Knight |
| 9,220,515 B2 | 12/2015 | Castaneda |
| 9,237,891 B2 | 1/2016 | Shelton |
| 9,247,978 B2 | 2/2016 | Euteneuer |
| 9,265,649 B2 | 2/2016 | Pflueger |
| D752,219 S | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter |
| 9,301,854 B2 | 4/2016 | Moskowitz |
| 9,307,988 B2 | 4/2016 | Shelton |
| 9,308,033 B2 | 4/2016 | Huebner |
| 9,326,768 B2 | 5/2016 | Shelton |
| 9,326,771 B2 | 5/2016 | Baxter |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |
| 9,408,603 B2 | 8/2016 | Patel |
| 9,408,604 B2 | 8/2016 | Shelton |
| 9,414,841 B2 | 8/2016 | Euteneuer |
| 9,414,871 B2 | 8/2016 | Huebner |
| 9,421,013 B2 | 8/2016 | Patel |
| 9,445,808 B2 | 9/2016 | Woodard |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton |
| 9,561,032 B2 | 2/2017 | Shelton |
| 9,566,063 B2 | 2/2017 | Euteneuer |
| 9,603,641 B2 | 3/2017 | Hulliger |
| 9,763,715 B2 | 9/2017 | Mather |
| 9,861,404 B2 | 1/2018 | Reiley |
| 10,299,842 B2 | 5/2019 | Hollis et al. |
| 10,433,888 B2 | 10/2019 | Hollis et al. |
| 2001/0028148 A1 | 10/2001 | White |
| 2002/0035369 A1 | 3/2002 | Beyar |

(56) References Cited

U.S. PATENT DOCUMENTS

| | | | | |
|---|---|---|---|---|
| 2002/0095181 | A1 | 7/2002 | Beyar | |
| 2002/0111641 | A1* | 8/2002 | Peterson | A61B 17/083 606/157 |
| 2002/0173793 | A1 | 11/2002 | Allen | |
| 2002/0177859 | A1 | 11/2002 | Monassevitch | |
| 2003/0083663 | A1 | 5/2003 | Goldhahn | |
| 2003/0100899 | A1 | 5/2003 | Wellisz | |
| 2003/0100900 | A1 | 5/2003 | Wellisz | |
| 2003/0100901 | A1 | 5/2003 | Wellisz | |
| 2003/0100902 | A1 | 5/2003 | Wellisz | |
| 2003/0139746 | A1 | 7/2003 | Groiso | |
| 2003/0225409 | A1 | 12/2003 | Freid | |
| 2004/0073222 | A1 | 4/2004 | Koseki | |
| 2004/0127896 | A1 | 7/2004 | Lombardo | |
| 2004/0133214 | A1 | 7/2004 | Kayan | |
| 2004/0172040 | A1 | 9/2004 | Heggeness | |
| 2004/0176780 | A1 | 9/2004 | Knopfle | |
| 2004/0220570 | A1 | 11/2004 | Frigg | |
| 2005/0021035 | A1 | 1/2005 | Groiso | |
| 2005/0043757 | A1 | 2/2005 | Arad | |
| 2005/0080454 | A1 | 4/2005 | Drews | |
| 2005/0085818 | A1 | 4/2005 | Huebner | |
| 2005/0096660 | A1 | 5/2005 | Allen | |
| 2005/0101961 | A1 | 5/2005 | Huebner | |
| 2005/0107796 | A1 | 5/2005 | Gerlach | |
| 2005/0119667 | A1 | 6/2005 | Leport | |
| 2005/0165400 | A1 | 7/2005 | Fernandez | |
| 2005/0171544 | A1 | 8/2005 | Falkner | |
| 2005/0234458 | A1 | 10/2005 | Huebner | |
| 2005/0240187 | A1 | 10/2005 | Huebner | |
| 2006/0058796 | A1 | 3/2006 | Hartdegen | |
| 2006/0058802 | A1 | 3/2006 | Kofoed | |
| 2006/0106391 | A1 | 5/2006 | Huebner | |
| 2006/0122604 | A1 | 6/2006 | Gorhan | |
| 2006/0129151 | A1 | 6/2006 | Huebner | |
| 2006/0161161 | A1 | 7/2006 | Shifrin | |
| 2006/0200147 | A1 | 9/2006 | Ensign | |
| 2006/0241612 | A1 | 10/2006 | Medoff | |
| 2006/0241618 | A1 | 10/2006 | Gasser | |
| 2006/0264936 | A1 | 11/2006 | Partin | |
| 2007/0055249 | A1 | 3/2007 | Jensen | |
| 2007/0173840 | A1 | 7/2007 | Huebner | |
| 2007/0208358 | A1 | 9/2007 | Kayan | |
| 2007/0233116 | A1 | 10/2007 | Olerud | |
| 2008/0167666 | A1 | 7/2008 | Fiere | |
| 2008/0195099 | A1 | 8/2008 | Minas | |
| 2008/0200955 | A1 | 8/2008 | Tepic | |
| 2008/0255620 | A1 | 10/2008 | Strauss | |
| 2008/0275510 | A1 | 11/2008 | Schonhardt | |
| 2008/0288000 | A1 | 11/2008 | Cawley | |
| 2009/0018556 | A1 | 1/2009 | Prandi | |
| 2009/0054930 | A1 | 2/2009 | Aflatoon | |
| 2009/0099602 | A1 | 4/2009 | Aflatoon | |
| 2009/0138082 | A1* | 5/2009 | Reah | A61B 17/7059 623/13.14 |
| 2009/0177203 | A1 | 7/2009 | Reiley | |
| 2009/0182383 | A1 | 7/2009 | Prybyla | |
| 2009/0254090 | A1 | 10/2009 | Lizee | |
| 2009/0254126 | A1* | 10/2009 | Orbay | A61B 17/1728 606/282 |
| 2009/0281543 | A1 | 11/2009 | Orbay | |
| 2009/0287249 | A1* | 11/2009 | Reynolds | A61B 17/809 606/246 |
| 2010/0036430 | A1* | 2/2010 | Hartdegen | A61B 17/8014 606/281 |
| 2010/0076448 | A1 | 3/2010 | Abdou | |
| 2010/0100138 | A1 | 4/2010 | Reynolds | |
| 2010/0106196 | A1 | 4/2010 | Erickson | |
| 2010/0125275 | A1 | 5/2010 | Kinman | |
| 2010/0133316 | A1 | 6/2010 | Lizee | |
| 2010/0211116 | A1 | 8/2010 | Suh | |
| 2010/0237128 | A1 | 9/2010 | Miller | |
| 2010/0256765 | A1 | 10/2010 | Butler | |
| 2010/0312280 | A1 | 12/2010 | Overes | |
| 2011/0022049 | A1 | 1/2011 | Huebner | |
| 2011/0029016 | A1 | 2/2011 | Yeung | |
| 2011/0029023 | A1 | 2/2011 | Tornier | |
| 2011/0029025 | A1* | 2/2011 | Medoff | A61B 17/8052 606/329 |
| 2011/0054542 | A1 | 3/2011 | Foley | |
| 2011/0092981 | A1 | 4/2011 | Ng | |
| 2011/0098754 | A1 | 4/2011 | Hulliger | |
| 2011/0118742 | A1 | 5/2011 | Hulliger | |
| 2011/0178522 | A1 | 7/2011 | Orbay | |
| 2011/0202092 | A1 | 8/2011 | Frigg | |
| 2011/0270326 | A1 | 11/2011 | Black | |
| 2011/0282393 | A1 | 11/2011 | Gerlach | |
| 2011/0295324 | A1 | 12/2011 | Donley | |
| 2011/0319942 | A1 | 12/2011 | Bottlang | |
| 2012/0022600 | A1* | 1/2012 | Overes | A61B 17/8004 606/286 |
| 2012/0024937 | A1 | 2/2012 | Allen | |
| 2012/0053638 | A1 | 3/2012 | Rusch | |
| 2012/0059425 | A1 | 3/2012 | Biedermann | |
| 2012/0065690 | A1 | 3/2012 | Perrow | |
| 2012/0078371 | A1 | 3/2012 | Gamache | |
| 2012/0085809 | A1 | 4/2012 | Milo | |
| 2012/0095513 | A1 | 4/2012 | Humphreys | |
| 2012/0130374 | A1* | 5/2012 | Bouduban | A61B 17/0642 606/75 |
| 2012/0136396 | A1 | 5/2012 | Baker | |
| 2012/0143193 | A1 | 6/2012 | Hulliger | |
| 2012/0150240 | A1* | 6/2012 | Medoff | A61B 17/8052 606/329 |
| 2012/0179207 | A1 | 7/2012 | Mekhail | |
| 2012/0191141 | A1 | 7/2012 | Costabile | |
| 2012/0323284 | A1 | 12/2012 | Baker | |
| 2013/0006247 | A1 | 1/2013 | Weiner | |
| 2013/0023938 | A1 | 1/2013 | Huebner | |
| 2013/0023940 | A1 | 1/2013 | Hansell | |
| 2013/0026206 | A1 | 1/2013 | Fox | |
| 2013/0026207 | A1 | 1/2013 | Fox | |
| 2013/0030437 | A1 | 1/2013 | Fox | |
| 2013/0109910 | A1 | 5/2013 | Alexander | |
| 2013/0138154 | A1 | 5/2013 | Reiley | |
| 2013/0150900 | A1 | 6/2013 | Haddad | |
| 2013/0206815 | A1 | 8/2013 | Fox | |
| 2013/0213843 | A1 | 8/2013 | Knight | |
| 2013/0218285 | A1 | 8/2013 | Kleinman | |
| 2013/0231667 | A1 | 9/2013 | Taylor | |
| 2013/0238035 | A1* | 9/2013 | Medoff | A61B 17/809 606/297 |
| 2013/0303071 | A1 | 11/2013 | Seki | |
| 2014/0014548 | A1 | 1/2014 | Knight | |
| 2014/0014553 | A1 | 1/2014 | Knight | |
| 2014/0018809 | A1 | 1/2014 | Allen | |
| 2014/0018862 | A1 | 1/2014 | Koay | |
| 2014/0020333 | A1 | 1/2014 | Knight | |
| 2014/0024002 | A1 | 1/2014 | Knight | |
| 2014/0034702 | A1 | 2/2014 | Miller | |
| 2014/0058461 | A1 | 2/2014 | Black | |
| 2014/0097228 | A1 | 4/2014 | Taylor | |
| 2014/0100652 | A1 | 4/2014 | Drews | |
| 2014/0142628 | A1* | 5/2014 | Traynelis | A61B 17/0642 606/246 |
| 2014/0163621 | A1 | 6/2014 | Huebner | |
| 2014/0163682 | A1 | 6/2014 | Lott | |
| 2014/0163683 | A1 | 6/2014 | Seifert | |
| 2014/0172026 | A1 | 6/2014 | Biedermann | |
| 2014/0200670 | A1 | 7/2014 | Chin | |
| 2014/0207195 | A1 | 7/2014 | Appenzeller | |
| 2014/0214037 | A1* | 7/2014 | Mayer | A61B 17/68 606/75 |
| 2014/0222086 | A1 | 8/2014 | Kuster | |
| 2014/0257420 | A1 | 9/2014 | Fox | |
| 2014/0276830 | A1 | 9/2014 | Cheney | |
| 2014/0277516 | A1 | 9/2014 | Miller | |
| 2014/0296925 | A1 | 10/2014 | Lawson | |
| 2014/0316470 | A1* | 10/2014 | Hartdegen | A61B 17/66 606/281 |
| 2014/0358187 | A1 | 12/2014 | Taber | |
| 2015/0012003 | A1 | 1/2015 | Ryan | |

(56) References Cited

U.S. PATENT DOCUMENTS

| | | |
|---|---|---|
| 2015/0045804 A1 | 2/2015 | Orbay |
| 2015/0066095 A1 | 3/2015 | Austin |
| 2015/0080914 A1 | 3/2015 | Roundy |
| 2015/0080969 A1 | 3/2015 | Holly |
| 2015/0108024 A1 | 4/2015 | Knight |
| 2015/0133940 A1 | 5/2015 | Palmer |
| 2015/0142063 A1 | 5/2015 | Austin |
| 2015/0148850 A1 | 5/2015 | Orbay |
| 2015/0164564 A1 | 6/2015 | Reiley |
| 2015/0173749 A1 | 6/2015 | Shelton |
| 2015/0173750 A1 | 6/2015 | Shelton |
| 2015/0173751 A1 | 6/2015 | Shelton |
| 2015/0173756 A1 | 6/2015 | Baxter |
| 2015/0196333 A1 | 7/2015 | Austin |
| 2015/0216570 A1 | 8/2015 | Hess |
| 2015/0216573 A1 | 8/2015 | Chin |
| 2015/0238238 A1 | 8/2015 | Cheney |
| 2015/0282819 A1 | 10/2015 | Austin |
| 2015/0313592 A1 | 11/2015 | Coillard-Lavirotte |
| 2015/0320462 A1 | 11/2015 | Biedermann |
| 2015/0351762 A1 | 12/2015 | Vendely |
| 2015/0351763 A1 | 12/2015 | Shelton |
| 2015/0351764 A1 | 12/2015 | Shelton |
| 2016/0066907 A1 | 3/2016 | Cheney |
| 2016/0074037 A1 | 3/2016 | Cheney |
| 2016/0089191 A1 | 3/2016 | Pak |
| 2016/0157906 A1 | 6/2016 | Hollis |
| 2016/0199060 A1* | 7/2016 | Morgan ............... A61B 17/068 227/175.1 |
| 2016/0235460 A1 | 8/2016 | Wahl |
| 2016/0242771 A1 | 8/2016 | Weinstein |
| 2016/0242927 A1 | 8/2016 | Seifert |
| 2016/0317199 A1 | 11/2016 | Hartdegen |
| 2016/0338697 A1* | 11/2016 | Biedermann ...... A61B 17/0642 |
| 2017/0065312 A1 | 3/2017 | Lauf |
| 2017/0112553 A1 | 4/2017 | Hansell |
| 2017/0119443 A1 | 5/2017 | Cawley |
| 2017/0156776 A1 | 6/2017 | Weiman |
| 2017/0181779 A1* | 6/2017 | Leither .............. A61B 17/8057 |
| 2017/0196604 A1 | 7/2017 | Hartdegen |
| 2017/0196606 A1 | 7/2017 | Cianfrani |
| 2017/0202552 A1 | 7/2017 | Coleman |
| 2017/0202585 A1 | 7/2017 | Leak |
| 2017/0209193 A1 | 7/2017 | Hartdegen |
| 2017/0238974 A1 | 8/2017 | Konieczynski |
| 2017/0245901 A1 | 8/2017 | Grigorian |
| 2017/0281157 A1 | 10/2017 | Hartdegen |
| 2018/0206892 A1 | 7/2018 | Hartdegen |
| 2018/0296257 A1 | 10/2018 | Penzimer |
| 2018/0353172 A1 | 12/2018 | Hartdegen |
| 2020/0100820 A1 | 4/2020 | Hollis |

FOREIGN PATENT DOCUMENTS

| | | |
|---|---|---|
| DE | 3119550 | 12/1982 |
| DE | 19821680 | 8/1999 |
| DE | 102004015223 | 10/2005 |
| EP | 0 092 383 | 11/1987 |
| EP | 0 253 629 | 9/1994 |
| EP | 0 768 062 | 4/1997 |
| EP | 0 826 340 | 3/1998 |
| EP | 0 857 462 | 8/1998 |
| EP | 0 682 920 | 5/2000 |
| EP | 0 867 149 | 9/2000 |
| EP | 1 870 042 | 7/2009 |
| EP | 2 231 044 | 3/2012 |
| EP | 3 082 632 | 10/2016 |
| EP | 3 166 505 | 5/2017 |
| EP | 3 166 522 | 5/2017 |
| EP | 3 179 939 | 6/2017 |
| FR | 2694696 | 11/1994 |
| FR | 2725126 | 4/1997 |
| FR | 2758252 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 | 10/1985 |
| GB | 2471648 | 1/2012 |
| WO | WO 92/017122 | 10/1992 |
| WO | WO 01/056489 | 8/2001 |
| WO | WO 03/068081 | 8/2003 |
| WO | WO 03/071962 | 9/2003 |
| WO | WO 08/007196 | 1/2008 |
| WO | WO 08/129061 | 10/2008 |
| WO | WO 10/004602 | 1/2010 |
| WO | WO 11/014547 | 2/2011 |
| WO | WO 11/110916 | 9/2011 |
| WO | WO 12/071129 | 5/2012 |
| WO | WO 13/010282 | 1/2013 |
| WO | WO 13/055824 | 4/2013 |
| WO | WO 13/130978 | 9/2013 |
| WO | WO 15/004391 | 1/2015 |
| WO | WO 15/095126 | 6/2015 |
| WO | WO 15/107311 | 7/2015 |
| WO | WO 16/007624 | 1/2016 |
| WO | WO 16/007626 | 1/2016 |
| WO | WO 16/025162 | 2/2016 |
| WO | WO 16/110760 | 7/2016 |
| WO | WO 17/011589 | 1/2017 |
| WO | WO 17/139315 | 8/2017 |
| WO | WO 17/139328 | 8/2017 |
| WO | WO 18/145064 | 8/2018 |
| WO | WO 18/148284 | 8/2018 |

* cited by examiner

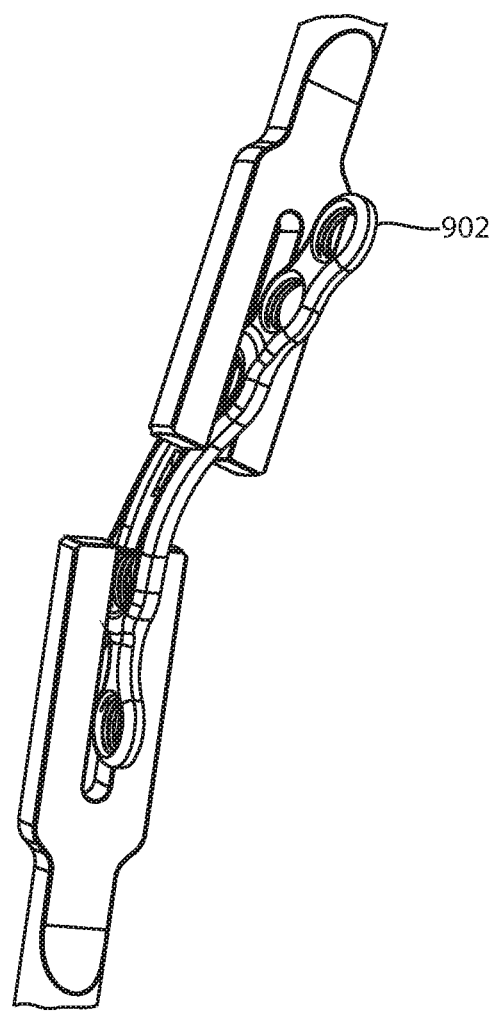
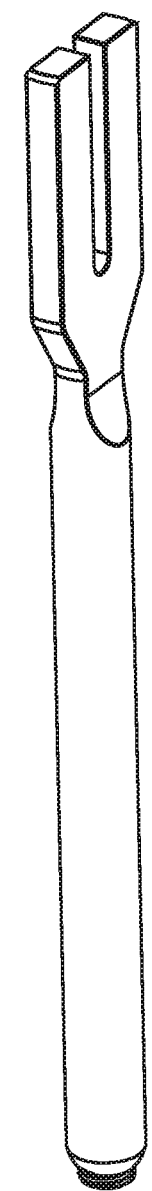
FIG. 16A
FIG. 16B

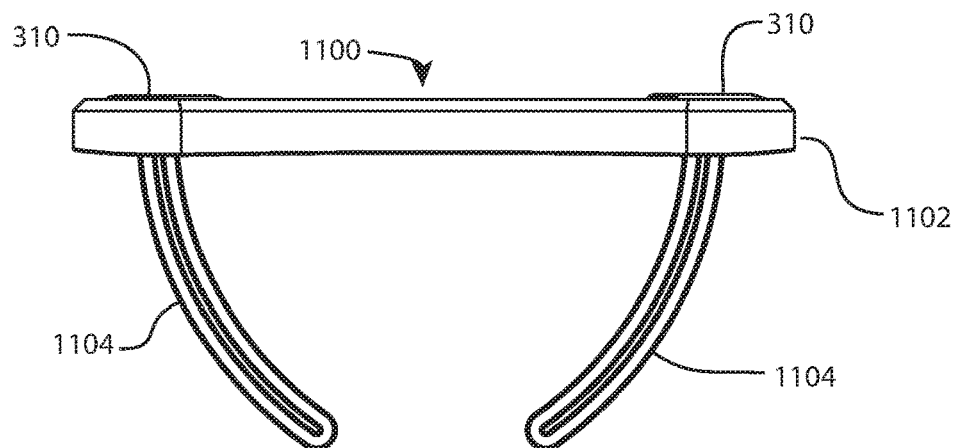
FIG. 25C
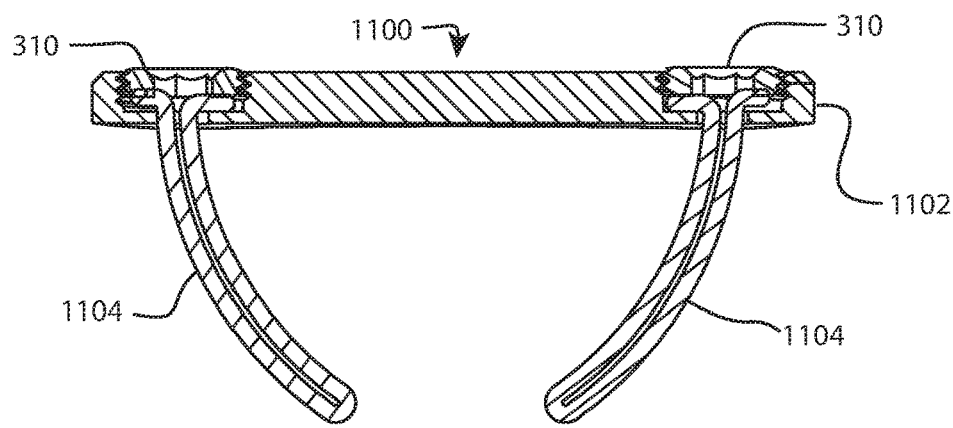
FIG. 25D
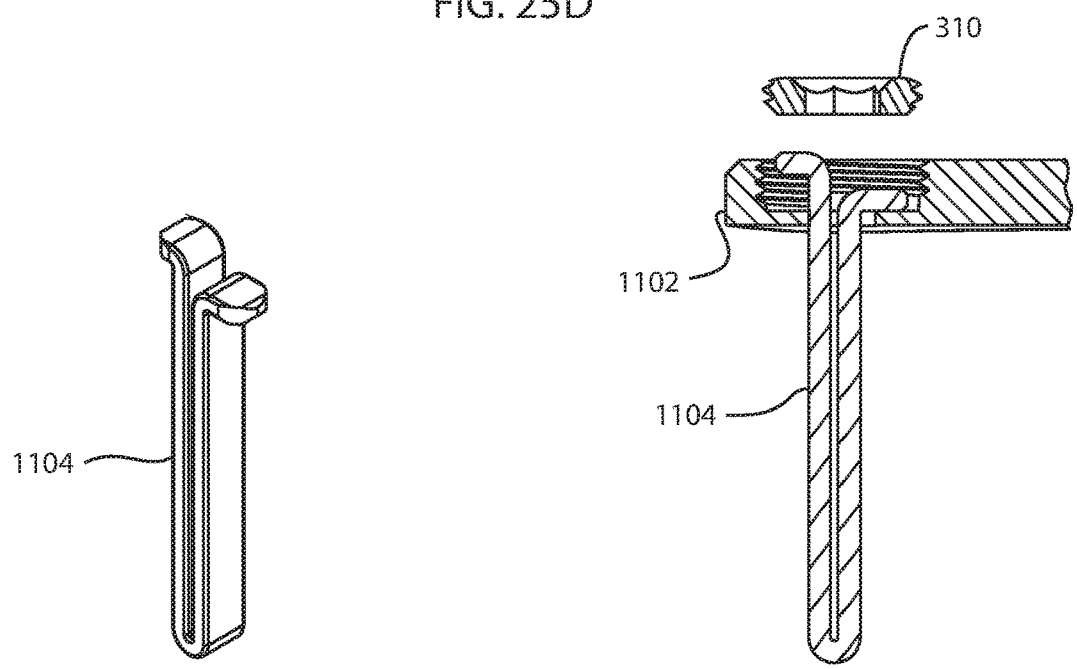
FIG. 25E
FIG. 25F

BONE PLATES WITH DYNAMIC ELEMENTS

CROSS-REFERENCE TO RELATED APPLICATIONS

The present application is a continuation of U.S. application Ser. No. 16/595,303, entitled "BONE PLATES WITH DYNAMIC ELEMENTS," filed Oct. 7, 2019, which is a continuation of U.S. application Ser. No. 16/368,794, entitled BONE PLATES WITH DYNAMIC ELEMENTS, filed Mar. 28, 2019, which is a continuation of U.S. application Ser. No. 15/209,623, entitled BONE PLATES WITH DYNAMIC ELEMENTS, filed Jul. 13, 2016, which claims the benefit of U.S. Provisional Application No. 62/192,059, entitled BONE PLATES WITH DYNAMIC ELEMENTS, filed Jul. 13, 2015. U.S. application Ser. No. 15/209,623 is also a continuation-in-part of International Patent Application No. PCT/US2014/070495, entitled POLYAXIAL LOCKING HOLE, filed Dec. 16, 2014, which claims the benefit of U.S. Provisional Application No. 61/919,069, entitled POLYAXIAL LOCKING HOLE, filed Dec. 20, 2013. U.S. application Ser. No. 15/209,623 is also a continuation-in-part of International Patent Application No. PCT/US2015/039551, entitled BONE IMPLANT AND MEANS OF INSERTION, filed Jul. 8, 2015, which claims the benefit of U.S. Provisional Application No. 62/022,811, entitled BONE IMPLANT AND MEANS OF INSERTION, filed Jul. 10, 2014. U.S. application Ser. No. 15/209,623 is also a continuation-in-part of International Patent Application No. PCT/US2015/039556, entitled BONE IMPLANT WITH ANTI-ROTATION, filed Jul. 8, 2015, which claims the benefit of U.S. Provisional Application No. 62/022,811, entitled BONE IMPLANT AND MEANS OF INSERTION, filed Jul. 10, 2014, and U.S. Provisional Application No. 62/036,240, entitled BONE IMPLANT WITH ANTI-ROTATION, filed on Aug. 12, 2014. The foregoing are incorporated by reference as though set forth herein in their entirety.

TECHNICAL FIELD

The present disclosure relates to plates having dynamic elements, otherwise known as elastic elements. Plates with dynamic elements may be used to stabilize and apply continuous load to hard tissues such as bone, or to soft tissues such as cartilage or ligaments. The present disclosure relates to plates with dynamic elements that provide continuous load across a joint, a resection, an osteotomy, a fracture, a tear, a laceration, or some other discontinuity between hard or soft tissue portions. The continuous load may be compressive or tensile. The present disclosure is made in the context of bone plates for use in the foot, having various dynamic elements including staples, elbow pegs or L-pegs, and straight pegs. However, the principles disclosed herein are applicable in locations throughout the body.

BACKGROUND

There are many circumstances in which bones, bone fragments, or other tissue portions must be fused together, united, or otherwise permanently joined. Some examples include arthrodesis, corrective osteotomy, fracture, tear, or laceration. Bones, bone fragments, or other tissue portions heal better when they are stabilized with some mechanical load or stress across the discontinuity, for example when the bones, bone fragments, or other tissue portions are compressed together or distracted apart. This disclosure describes solutions to the problem of stabilizing bones, bone fragments, or other tissue portions while applying a therapeutic level of continuous mechanical load or stress across the discontinuity.

SUMMARY

The various systems and methods of the present technology have been developed in response to the present state of the art, and in particular, in response to the problems and needs in the art that have not yet been fully solved by currently available fixation systems. The systems and methods of the present technology may provide a means for dynamic loading while providing an overall stable construct.

To achieve the foregoing, and in accordance with the technology as embodied and broadly described herein, plate members provide stabilization and/or deformity correction in conjunction with dynamic elements that provide continuous dynamic load between tissue portions. The plate members may or may not be used with the dynamic elements. The dynamic elements may be separate parts that may be attached to the plate members, or they may be integrally formed with the plate members. The plate members and the dynamic elements may be made from the same materials or from different materials. The dynamic elements may be made from any elastic material, preferably a highly elastic metal, preferably a superelastic metal, preferably nitinol.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

4D is another exploded oblique view of the assembly of FIG. 4A from a different direction.

FIG. 16A is an oblique detail view of a plate of FIG. 10 with two benders of the kit of FIG. 14; and FIG. 16B is an oblique detail view of the plate and a bender of FIG. 16A.

FIG. 18 shows the step of inserting the bone plate.

FIG. 19B shows the step of drilling for a locking screw.

FIG. 20B shows the step of drilling for a non-locking screw.

FIG. 21 shows the step of driving a locking screw.

FIG. 25C is a side view of the assembly of FIG. 25A; FIG. 25D is a longitudinal cross-section of a portion of the assembly of FIG. 25A along a mid-sagittal plane of the bone plate; FIG. 25E is an oblique view of the wire peg of FIG. 25A in a free state; FIG. 25F is a cross sectional view of a portion of the assembly of FIG. 25A, with a wire peg in a free state.

DETAILED DESCRIPTION

Figure 1A:
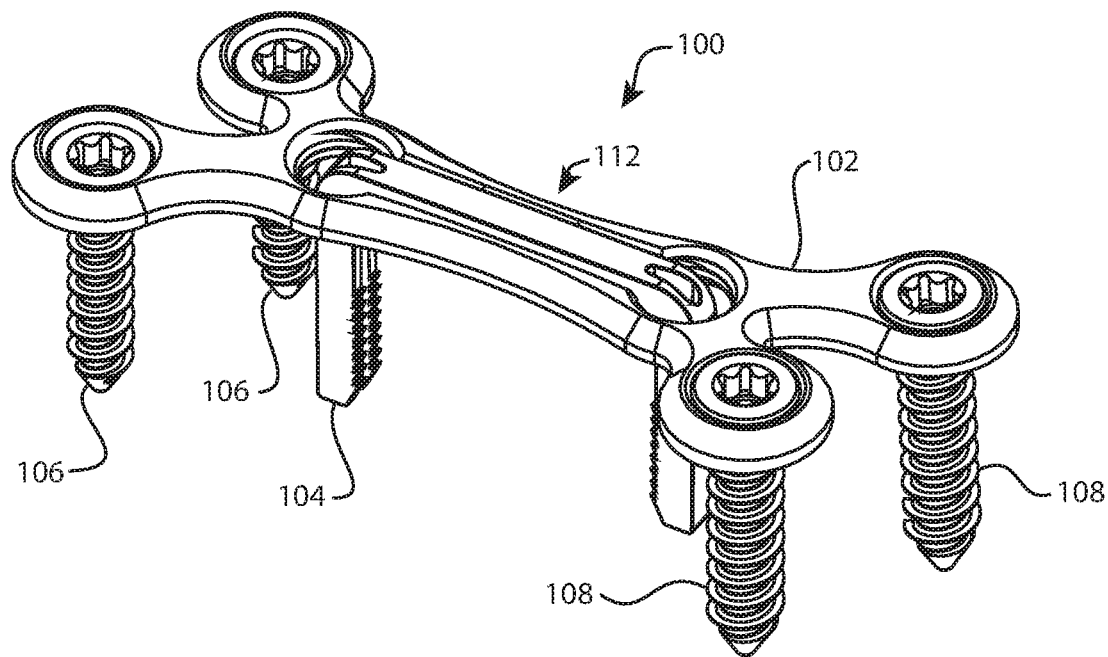
FIG. 1A is an oblique view of an assembly with a bone plate, a staple, and screws.
Figure 1B:
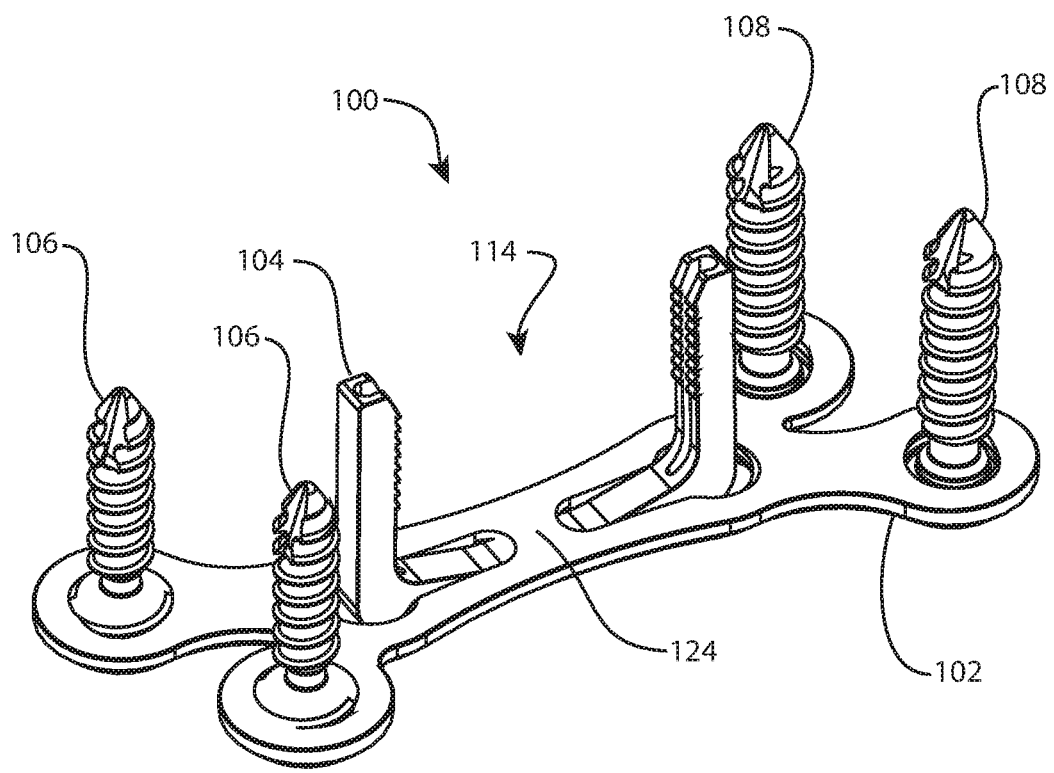
FIG. 1B is another oblique view of the assembly of FIG. 1A from a different direction.
Figure 1C:
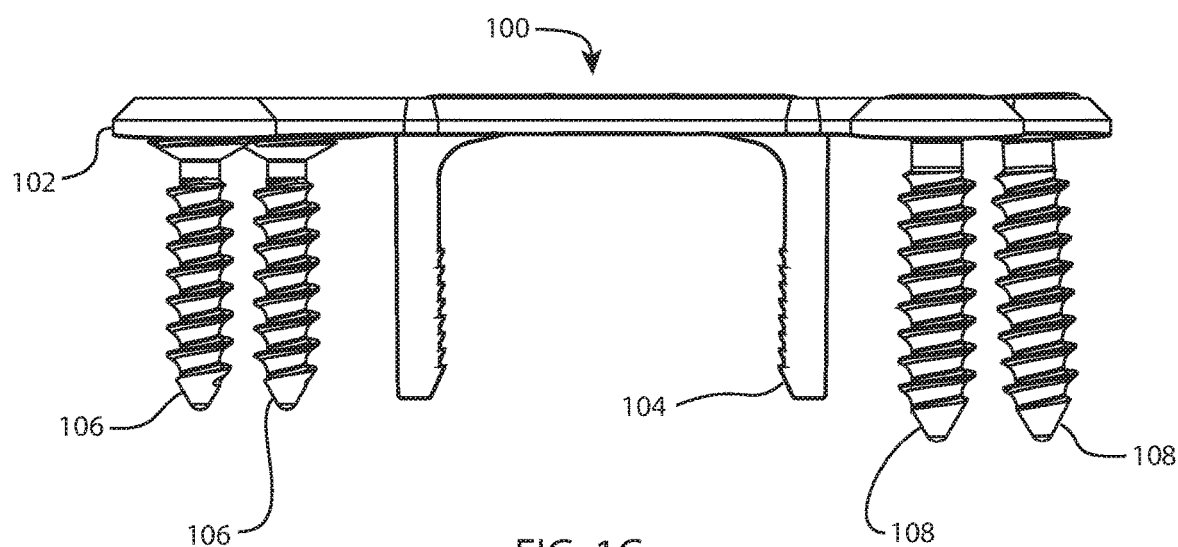
FIG. 1C is a side view of the assembly of FIG. 1A.
Figure 1D:
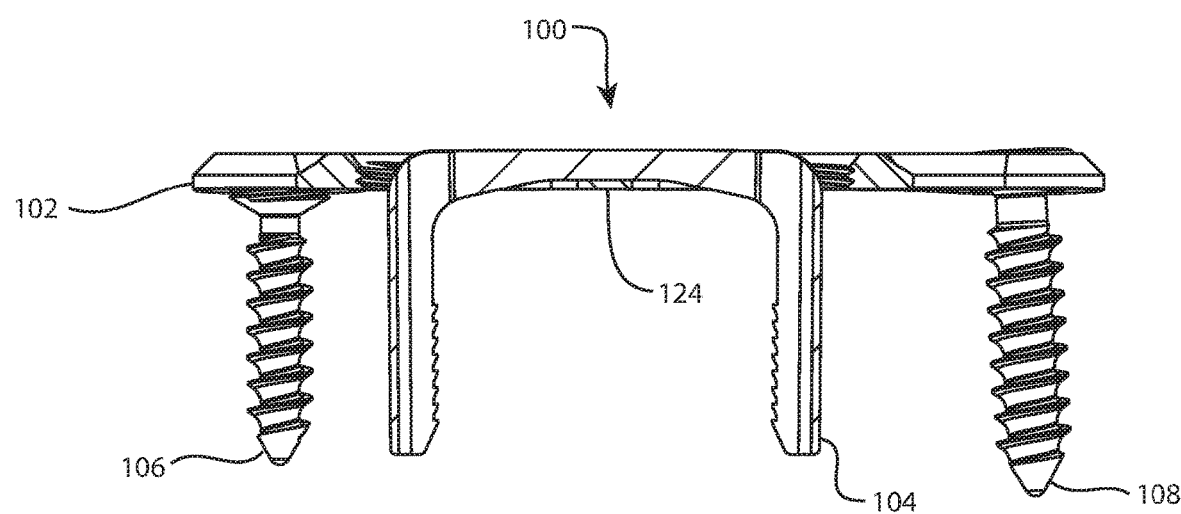
FIG. 1D is a longitudinal cross-section of the assembly of FIG. 1A along a mid-sagittal plane of the bone plate.
Figure 1E:
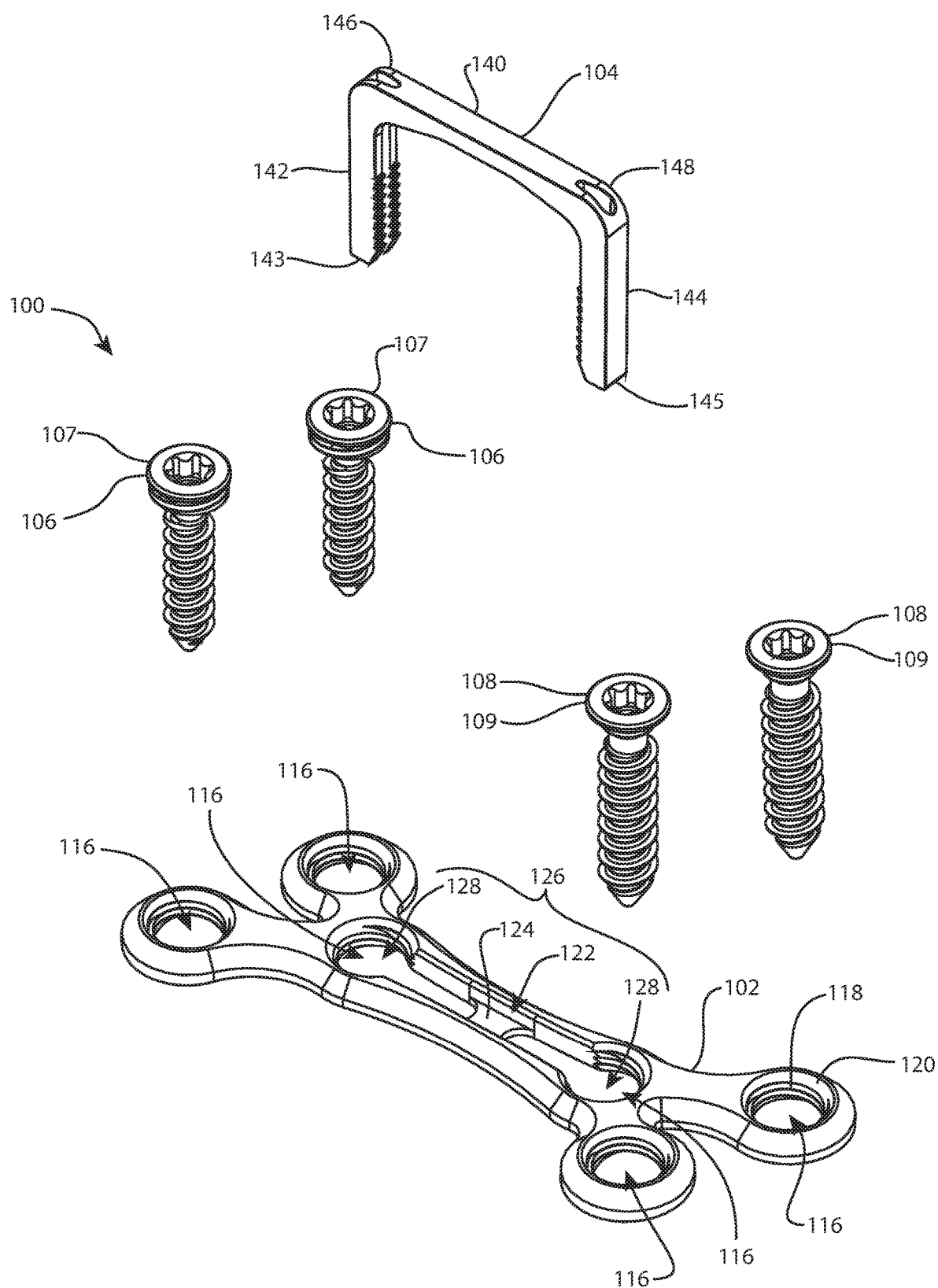
FIG. 1E is an exploded oblique view of the assembly of FIG. 1A.
Figure 1F:
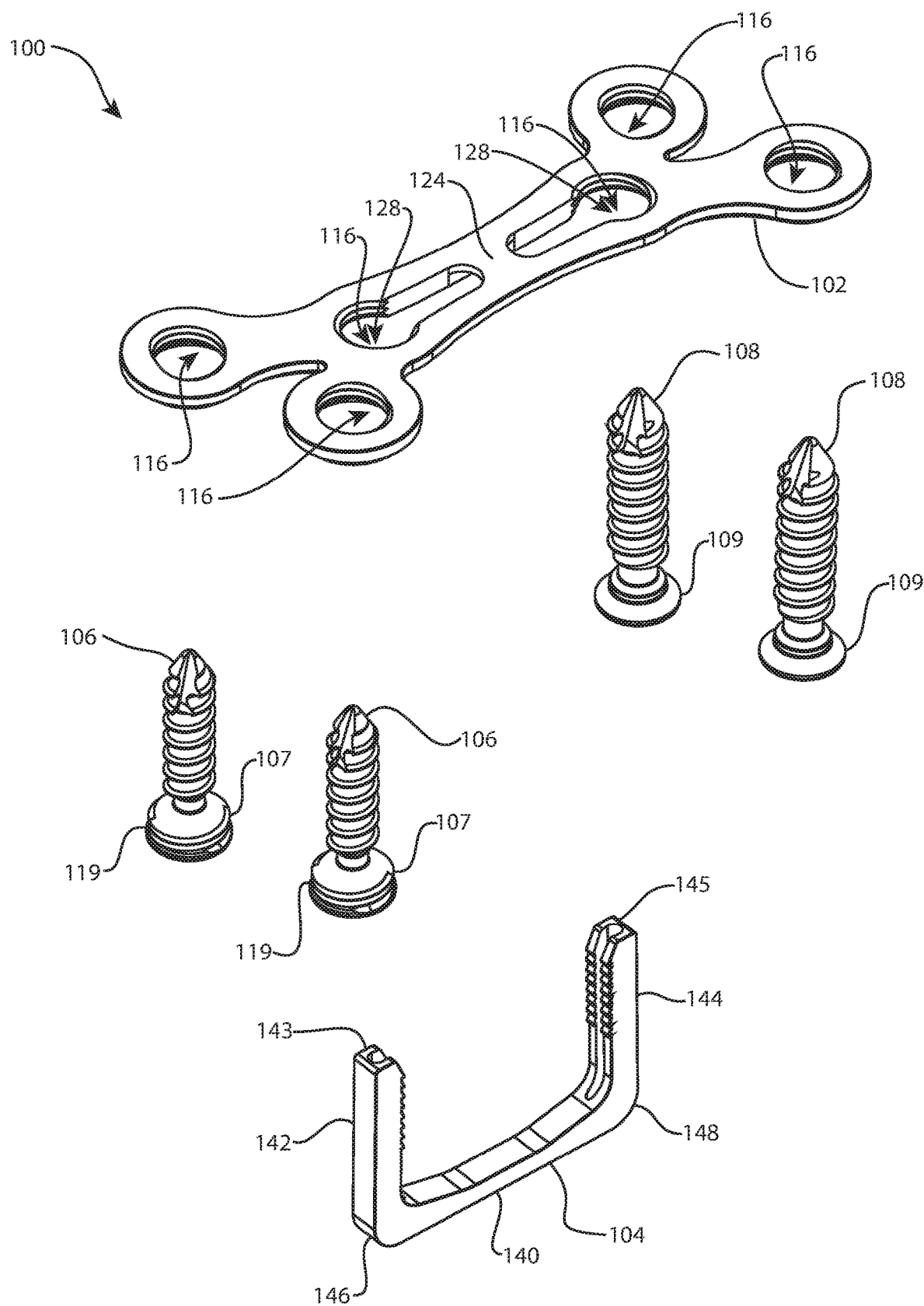
FIG. 1F is another exploded oblique view of the assembly of FIG. 1A from a different direction.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

In this specification, an elastically deformed state is defined as deformation equivalent to strain values above 0.2%, for example strain values between 0.2% and 6%. An elastically deformed state is distinct from the small magnitude of deformation and strain tolerated by most materials under load In this specification, a static material, or a static design, or a static component, is defined as a material, design, or component that tolerates deformation equivalent to no more than 0.2% strain before experiencing permanent plastic deformation, bending, cracking, breaking, or other failure mode Referring to FIGS. 1A-1F, an assembly 100 may include a stabilizing member, a dynamic element, and one or more fasteners. In assembly 100, the stabilizing member may be a bone plate 102, the dynamic element may be a staple 104, and the fasteners may be screws. Assembly 100 is illustrated with locking screws 106 on the left and non-locking screws 108 on the right.

Figure 11:
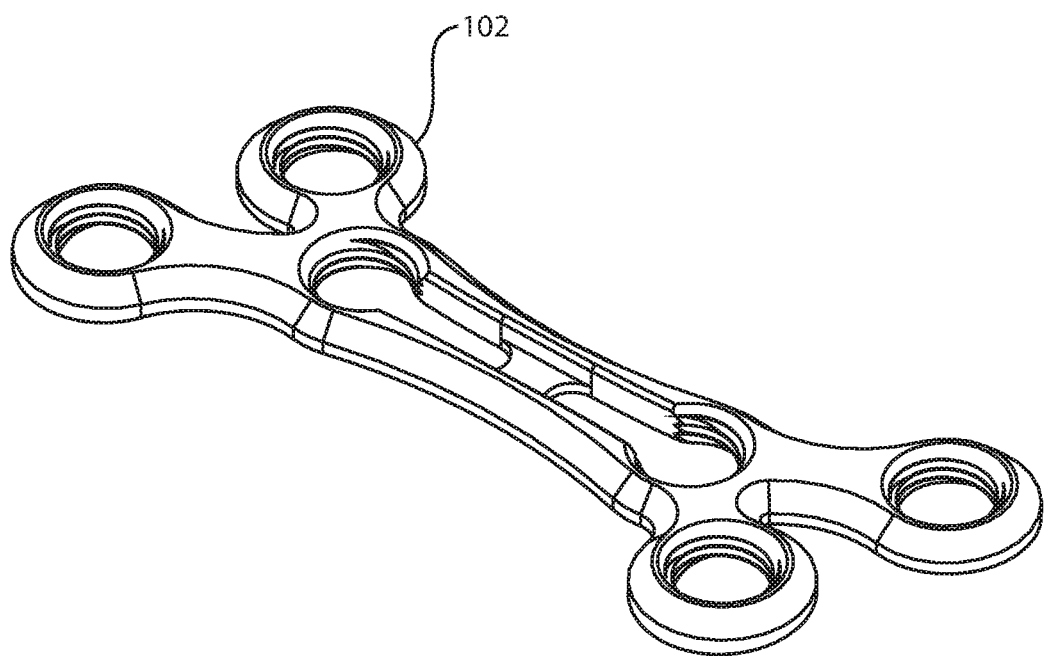
FIG. 11 is another oblique view of the bone plate of FIG. 1A.
Figure 12A:
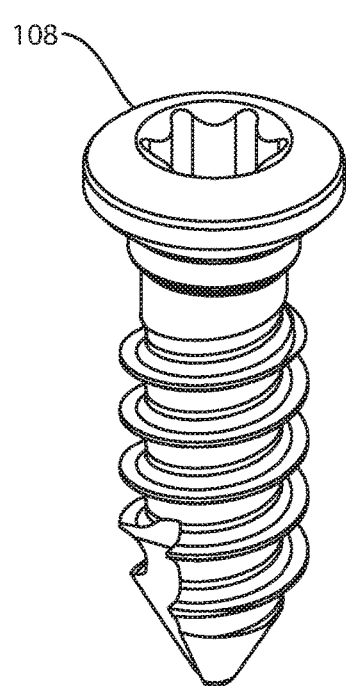
FIG. 12A is an oblique view of the screws of FIG. 1A.
Figure 12A:
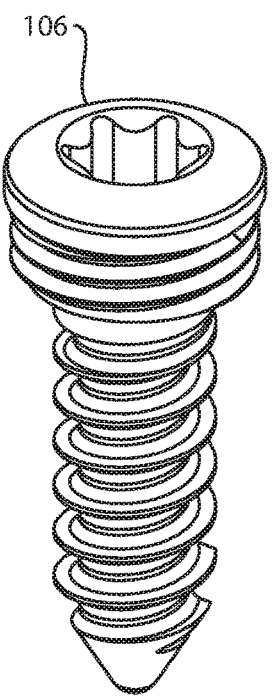
Figure 12B:
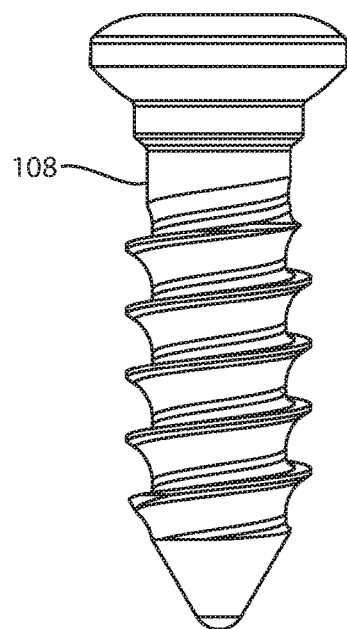
FIG. 12B is a side view of the screws of FIG. 1A.
Figure 12B:
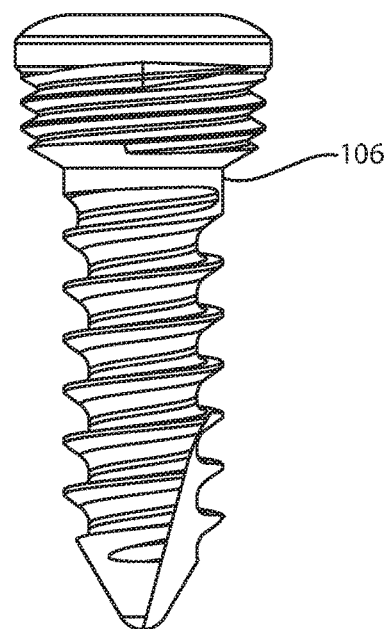
Figure 13A:
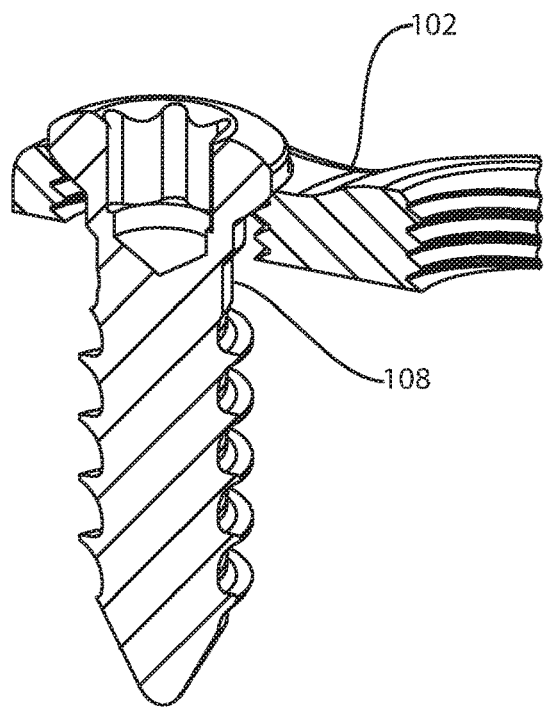
FIG. 13A is an oblique cross-section detail view of the non-locking screw of FIG. 1A in a hole of the bone plate of FIG. 1A.
Figure 13B:
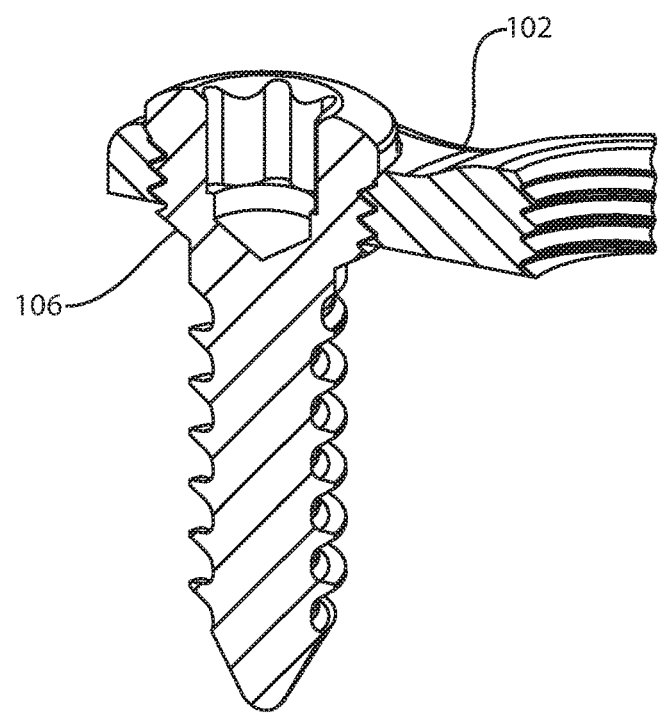
FIG. 13B is an oblique cross-section detail view of the locking screw of FIG. 1A in a hole of the bone plate of FIG. 1A.

The bone plate 102 has an obverse side 112 and a reverse side 114. When the bone plate 102 is implanted, the obverse side 112 faces away from the bone portions and the reverse side 114 faces toward the bone portions. The bone plate 102 includes several holes 116 which extend through the obverse and reverse sides 112, 114. Six holes 116 are illustrated, although any number of holes may be present. Each hole 116 includes an internally threaded portion 118 and a non-threaded portion 120 so that each hole 116 accepts either the locking screw 106 or the non-locking screw 108. See FIGS. 13A and 13B. The internally threaded portion 118 engages external threads 119 on the head 107 of the locking screw 106. The internally threaded portion 118 may be adjacent to the reverse side 114. The non-threaded portion 120 engages the head 109 of the non-locking screw 108. The non-threaded portion 120 may be adjacent to the obverse side 112. The non-threaded portion 120 may be concave and/or elongated. An optional groove 122 in the obverse side 112 extends between two of the holes 116. Each of these two holes 116 is also elongated toward the other hole 116, leaving a web 124 extending between the two holes 116. The web 124 may be adjacent to the reverse side 114. The web 124 separates the two holes 116, and may be present even if the holes 116 are not elongated towards each other. The optional groove 122 if present, the two elongated holes 116, and the web 124 are referred to collectively as a receiver 126, and the involved holes 116 are referred to as receiver holes 128. A receiver 126 may be included between any two holes through a bone plate. Multiple receivers 126 may be included on a single bone plate. For example, referring to FIGS. 1A and 1E, the bone plate 102 may be modified to include a second receiver between the left two holes 116 and/or a third receiver between the right two holes 116. Two receivers 126 may share a common receiver hole 128. The bone plate 102 may be much more stiff than the dynamic element, which in this example is the staple 104. The bone plate 102 may be rigid, or static as defined above. Alternatively, the bone plate 102 may be malleable or elastic. The bone plate 102 may include rigid and malleable regions. The illustrated bone plate 102 may be 2 mm thick in the vicinity of the receiver 126 and 1.5 mm thick in the vicinity of the leftmost two holes 116 and the rightmost two holes 116. The bone plate 102 may accommodate a staple 104 that is 18 mm×14 mm. The bone plate 102 is also illustrated in FIG. 11.

Figure 10:
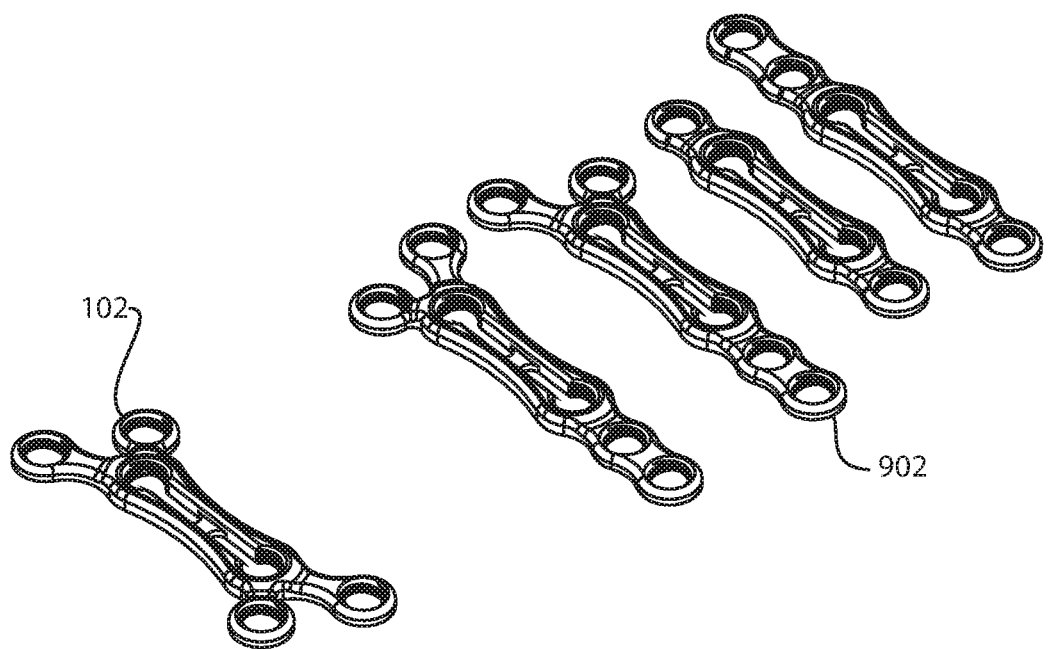
FIG. 10 is an oblique view of a kit of bone plates.

Referring to FIG. 10, several different bone plate shapes may be provided in a kit or a set. FIG. 10 shows, from left to right, a left double Y plate 102, a left Y plate, a right Y plate 902, a straight 4-hole plate, and a straight 5-hole plate. A kit or set may also include a left metatarsophalangeal plate with 10 degree varus and zero degree dorsiflexion (not shown), and a right metatarsophalangeal plate with 10 degree varus and zero degree dorsiflexion (not shown).

The staple 104 is described in at least one of the patent applications identified in this application. The staple 104 may be the implant 200 of FIGS. 11 and 12, implant 300 of FIGS. 15A-16B, implant 600 of FIGS. 21 and 22, implant 800 of FIGS. 23A-24, or implant 2200 of FIGS. 78 and 79 of International Patent Application Serial No. PCT/US2015/039551; or implant 100 of FIGS. 1-3, staple 300 of FIGS. 4 and 5, staple 400 of FIG. 7, staple 480 of FIG. 8, or implant 2100 of FIGS. 10A and 10B of International Patent Application Serial No. PCT/US2015/039556.

The staple 104 includes a body 140 or bridge, a first leg 142, and a second leg 144. The bridge extends between a first end 146 and a second end 148. The first leg 142 is coupled to the first end 146 and terminates in a first free end 143. The second leg 144 extends from the second end 148 and terminates in a second free end 145.

The staple 104 has an insertion state, or elastically deformed state, which is its shape under the influence of an external force, for example, an external force applied by a staple inserter tool. A first distance separates the free ends 143, 145 in the elastically deformed state. The staple 104 also has a free state, or relaxed state, which is its shape when no external forces are acting upon the staple, other than gravity. A second distance separates the free ends 143, 145 in the relaxed state. The second distance is different from the first distance. In the example shown, the legs 142, 144 of the staple 104 are parallel to one another in the elastically deformed state. However, the legs 142, 144 may converge or diverge in the elastically deformed state. In the example shown, the legs 142, 144 of the staple converge at their free ends, or tips, in the relaxed state, so that the second distance is less than the first distance. However, the legs 142, 144 may diverge at their free ends, or the legs 142, 144 may be parallel in the relaxed state. The staple 104 assumes the elastically deformed state under the influence of an external force. The staple 104 may resume the free state as soon as the external force is removed. If the legs 142, 144 of the staple 104 are engaged in bone holes, then the staple may only be able to partially relax toward the free state due to the resistance of the bone. In this situation, the staple 104 may be in a loaded state in between the elastically deformed state and the relaxed state. The loaded state of the staple is shown in FIGS. 1A-1F. The staple 104 is preferably made of a superelastic alloy such as nitinol, although other materials are also suitable. In this example, the staple 104 is not locked to the bone plate 102, although in subsequent examples the staple is locked to the bone plate. In this example, the body 140 of the staple 104 rests within the groove 122 of the receiver 126 against the web 124, and the staple legs 142, 144 extend through the receiver holes 128 and protrude from the reverse side 114 of the bone plate 102. The web 124 prevents the body 140 from passing through the reverse side 114 of the bone plate 102. The receiver 126 holds the staple 104 in a predetermined orientation and relative position with respect to the bone plate 102. The receiver 126 is one example of a group of features that function together to hold a staple a in a predetermined orientation and relative position with respect to a bone plate. Different features, or groups of features, may provide the same function. For example, the groove 122 may be lacking so that the body 140 of the staple 104 rests atop the obverse side 112 of the bone plate 102, or the web 124 may be replaced by ledges or other supports to serve as a stop or a docking point to prevent the body 140 from passing through the reverse side 114. Furthermore, the web 124 may be replaced by one or more stop feature(s) or docking feature(s) on the staple 104 instead of on the bone plate 102.

The locking screw 106 locks securely to any hole 116 in the bone plate 102. The locking screw 106 may include an externally threaded head 107 which locks to the hole 116 in the bone plate 102 when threaded tightly into the internally threaded portion 118 of the hole 116. The locking screw 106 may be the design disclosed in at least one of the patent applications identified in this application. The locking screw 106 may be the bone fixation device 390 of FIG. 11, bone fixation device 500 of FIGS. 24-26, bone fixation device 600 of FIGS. 27-30 of International Patent Application Serial No. PCT/US2014/070495. The locking screw may have a 3.0 mm diameter and lengths from 8 mm to 30 mm in 2 mm increments. The locking screw 106 is also illustrated in FIG. 12.

The non-locking screw 108 does not lock to the holes 116 in the bone plate 102. Instead, it remains free to rotate and translate within the confines of the screw hole 116 after implantation. The non-locking screw 108 may be polyaxially positionable relative to the screw hole 116. The non-locking screw 108 may include a head 109 with an exterior surface that forms a ball-and-socket joint with the non-threaded portion 120 of the hole 116. The exterior surface may be convex, spherical, or conical. The non-locking screw 108 may have a 3.5 mm diameter and lengths from 8 mm to 30 mm in 2 mm increments. The non-locking screw 108 is also illustrated in FIG. 12.

Referring to FIG. 13, the screws 106 and 108 are interchangeable in the screw holes 116 of the bone plate 102.

Figure 2:
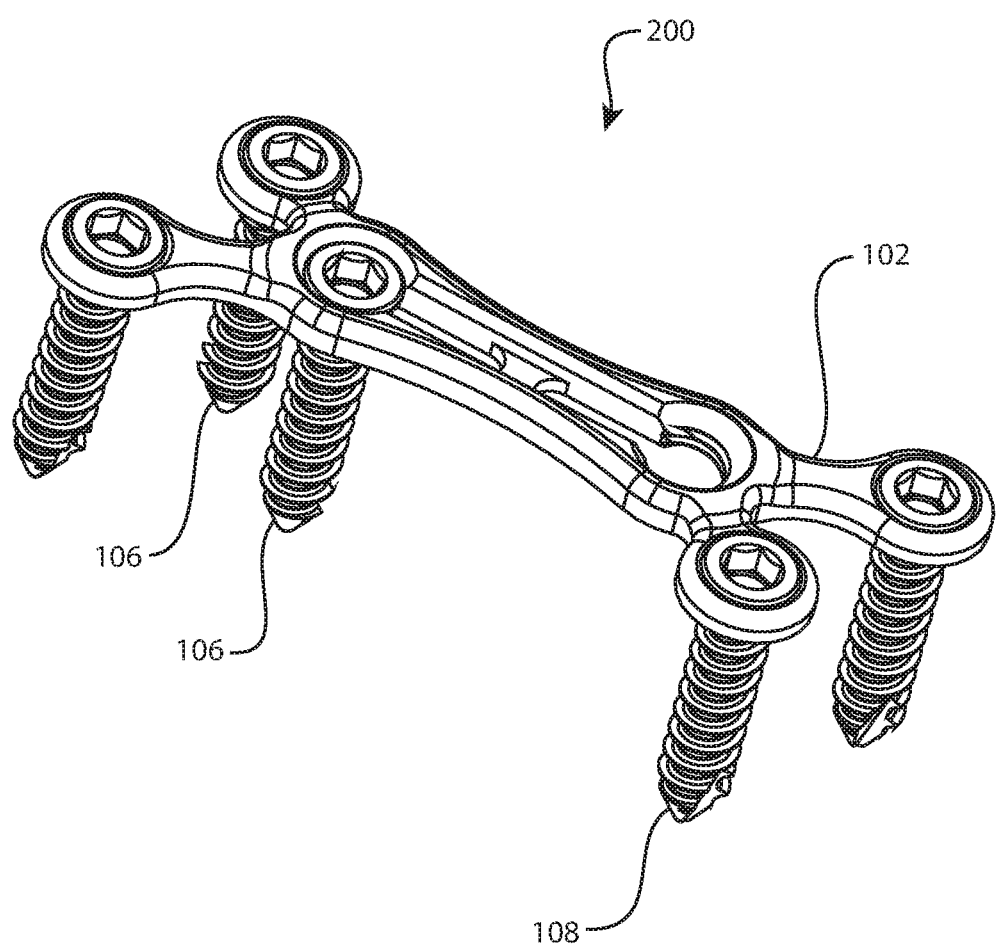
FIG. 2 is an oblique view of an assembly with the bone plate of FIG. 1A and screws.
Figure 3A:
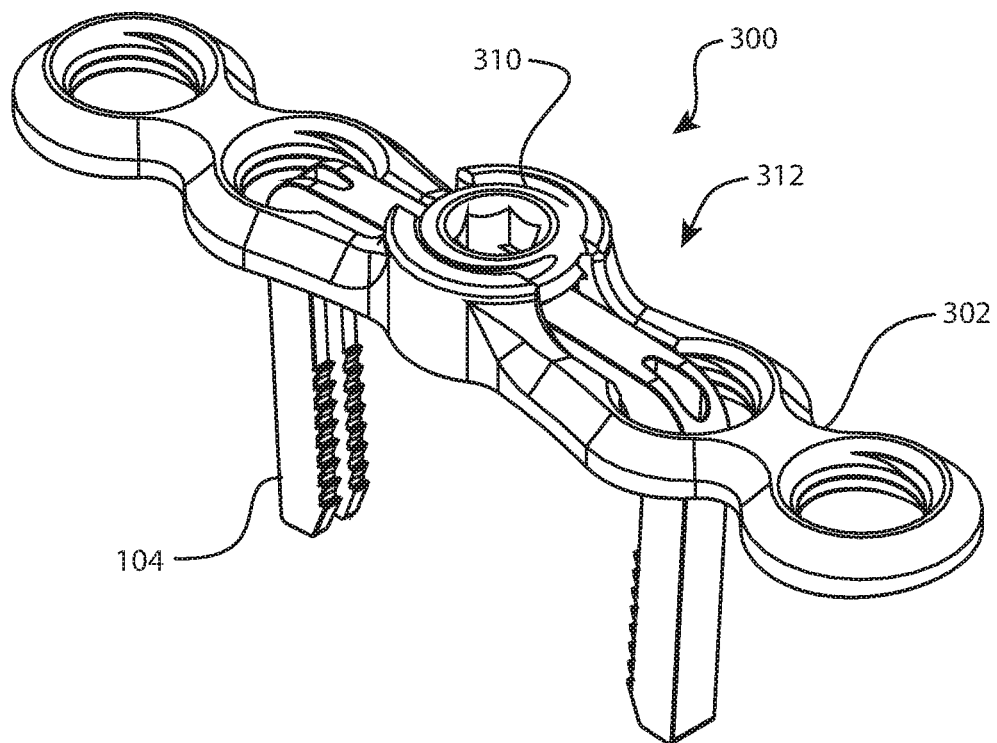
FIG. 3A is an oblique view of an assembly with a bone plate, a staple, and a set screw.
Figure 3B:
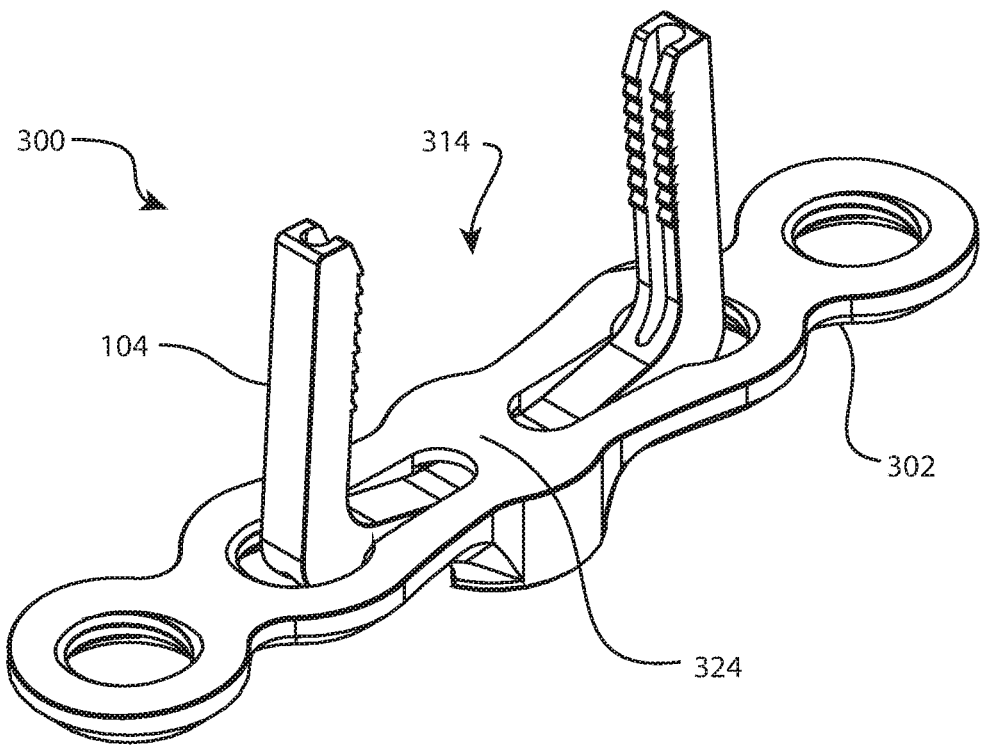
FIG. 3B is another oblique view of the assembly of FIG. 3A from a different direction.
Figure 3C:
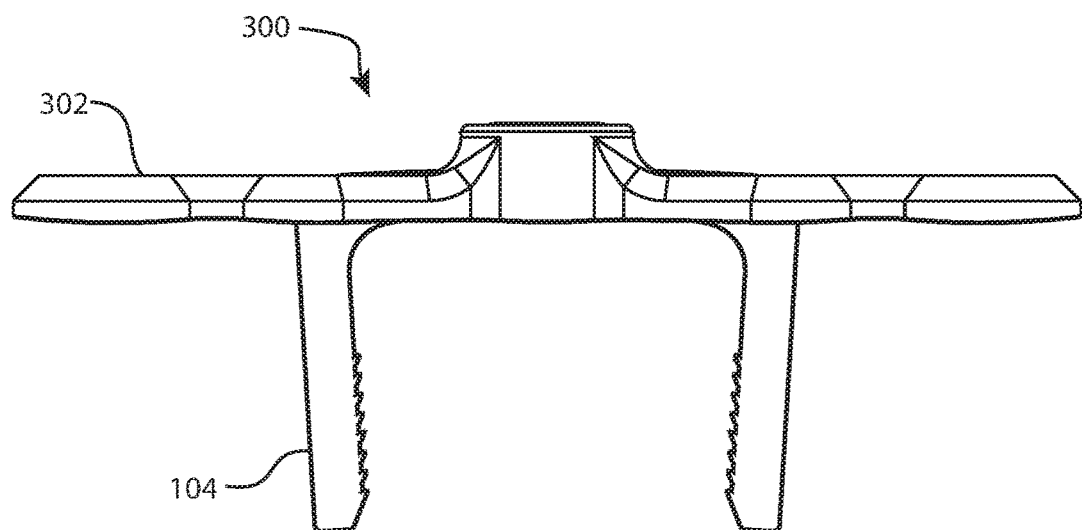
FIG. 3C is a side view of the assembly of FIG. 3A.
Figure 3D:
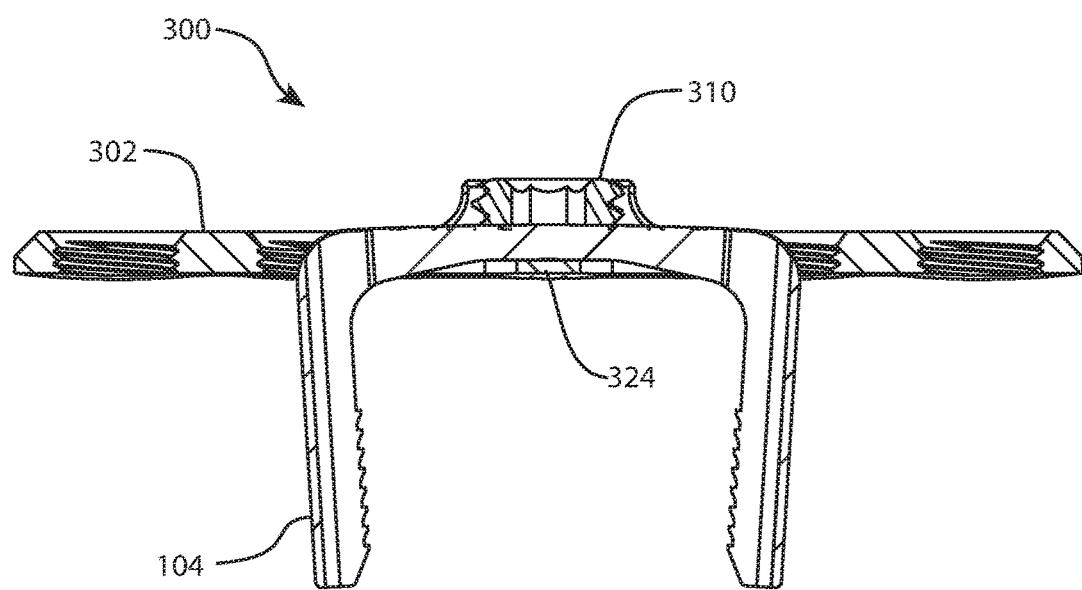
FIG. 3D is a longitudinal cross-section of the assembly of FIG. 3A along a mid-sagittal plane of the bone plate.
Figure 3E:
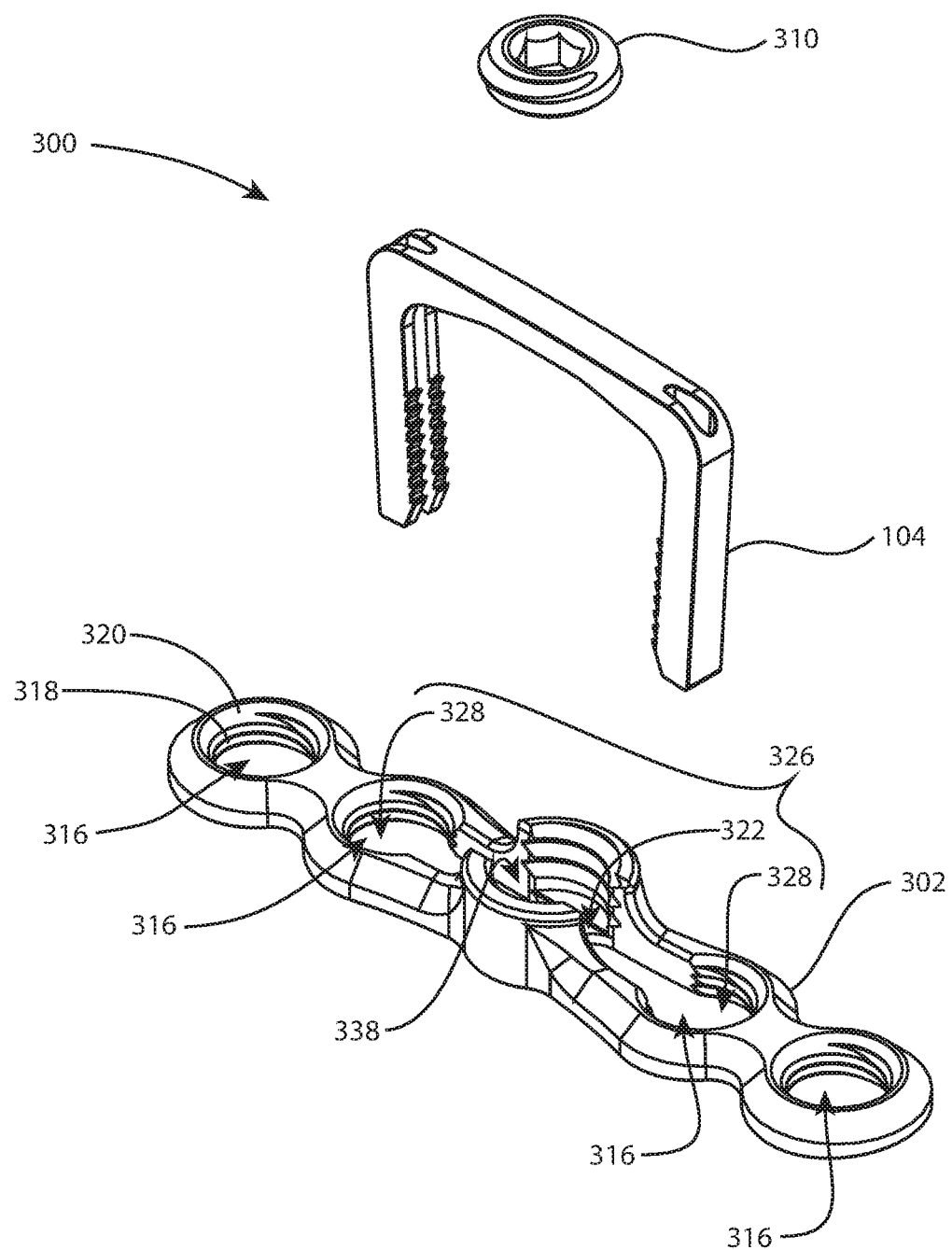
FIG. 3E is an exploded oblique view of the assembly of FIG. 3A.
Figure 3F:
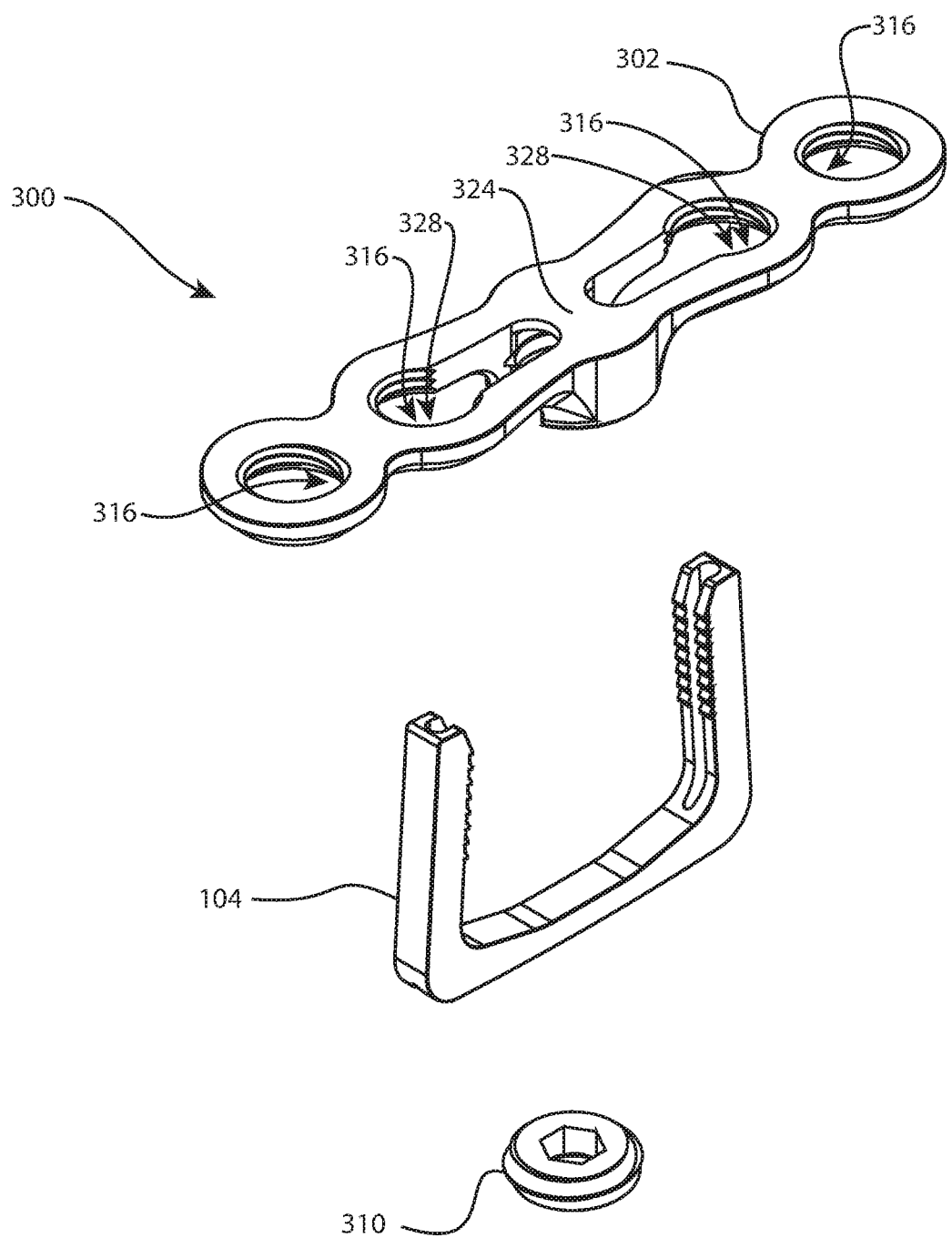
FIG. 3F is another exploded oblique view of the assembly of FIG. 3A from a different direction.

Referring to FIG. 2, an assembly 200 may include a stabilizing member and one or more fasteners. In assembly 200, the stabilizing member may be the bone plate 102 and the fasteners may include one or more of the screws 106 and/or 108. This example includes a locking screw 106 in one of the receiver holes, showing that the screws 106 or 108 can be used interchangeably in the receiver holes 128 as well as the other holes 116 of the bone plate 102.

Referring to FIGS. 3A-3F, an assembly 300 may include a stabilizing member, a dynamic element, and one or more fasteners. In assembly 300, the stabilizing member may be a bone plate 302, the dynamic element may be the staple 104, and the fasteners may include a set screw 310 and one or more of the screws 106 and/or 108, although the screws 106 and 108 are omitted from the illustration for clarity.

The bone plate 302 has an obverse side 312 and a reverse side 314. The bone plate 302 includes several holes 316, each of which may include an internally threaded portion 318 and a non-threaded portion 320, the same as hole 116. The internally threaded portion 318 may be adjacent to the reverse side 314 and the non-threaded portion 320 may be adjacent to the obverse side 312. An optional groove 322 in the obverse side 312 extends between two of the holes 316. Each of these two holes 316 is also elongated toward the other hole 316, leaving a web 324 extending between the two holes 316. The web 324 may be adjacent to the reverse side 314. The web 324 separates the two holes 316, and may be present even if the holes 316 are not elongated towards each other. The web 324 prevents the body 140 from passing through the reverse side 314. The optional groove 322 if present, the two elongated holes 316, and the web 324 are referred to collectively as a receiver 326, and the involved holes 316 are referred to as receiver holes 328. The bone plate 302 includes an internally threaded socket 338 which receives the set screw 310 in threaded engagement. The set screw 310 locks the staple 104 to the bone plate 302, and may be referred to as a locking mechanism.

Referring to FIGS. 4A-4G, an assembly 400 may include a stabilizing member, a dynamic element, and one or more fasteners. In assembly 400, the stabilizing member may be a bone plate 402, the dynamic element may be the staple 104, and the fasteners may include one or more of the screws 106 and/or 108, although the screws 106 and 108 are omitted from the illustration for clarity.

Figure 4A:
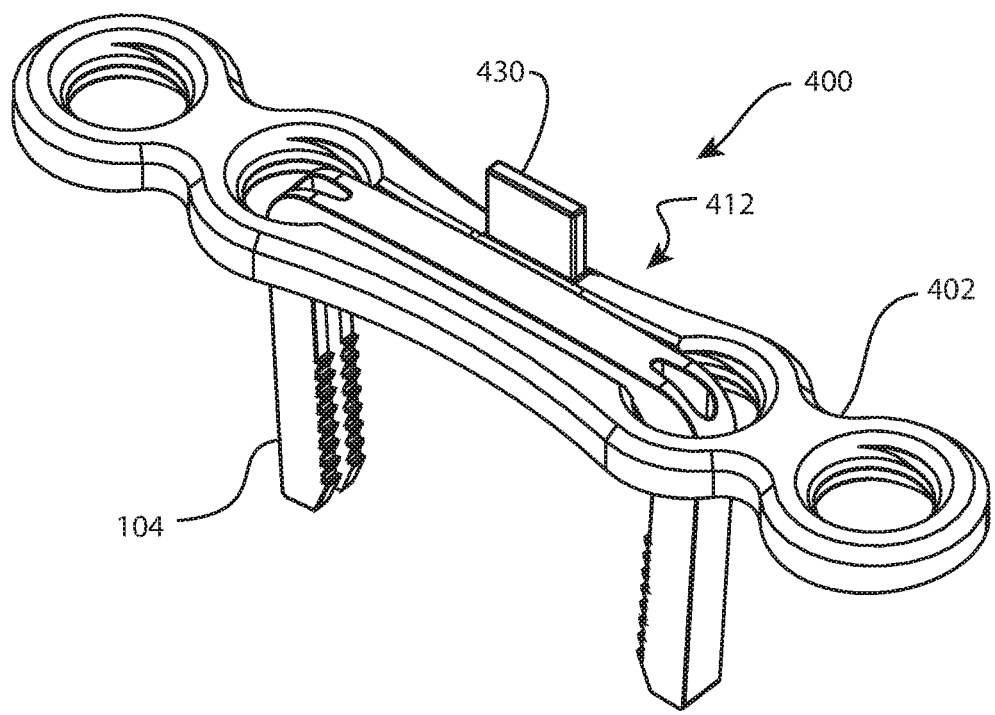
FIG. 4A is an oblique view of an assembly with a bone plate and a staple.
Figure 4B:
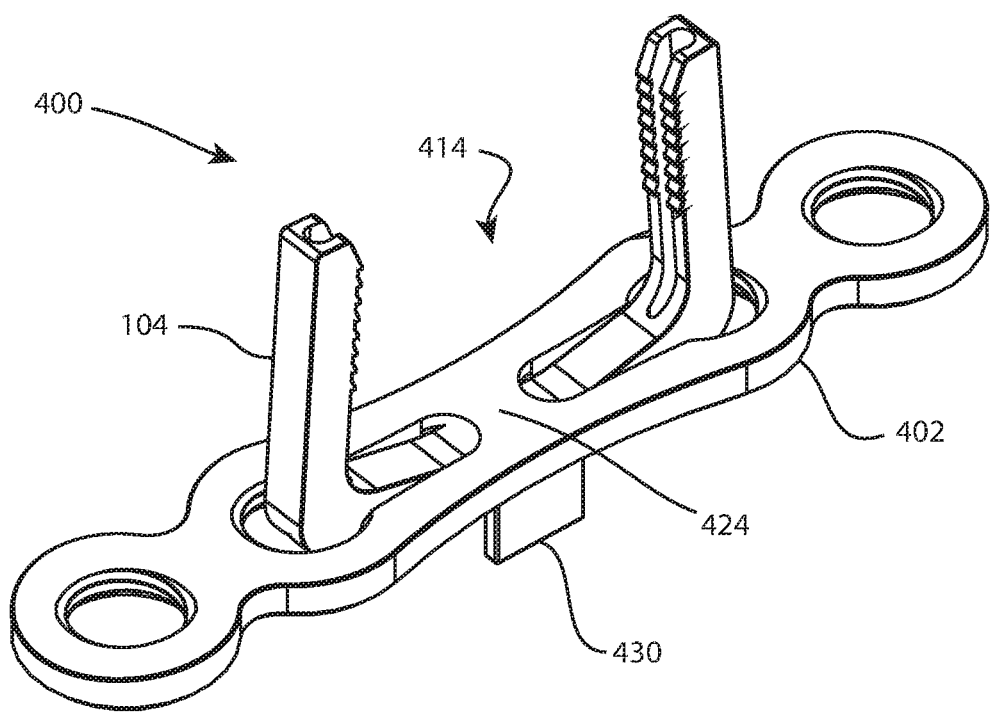
FIG. 4B is another oblique view of the assembly of FIG. 4A from a different direction.
Figure 4C:
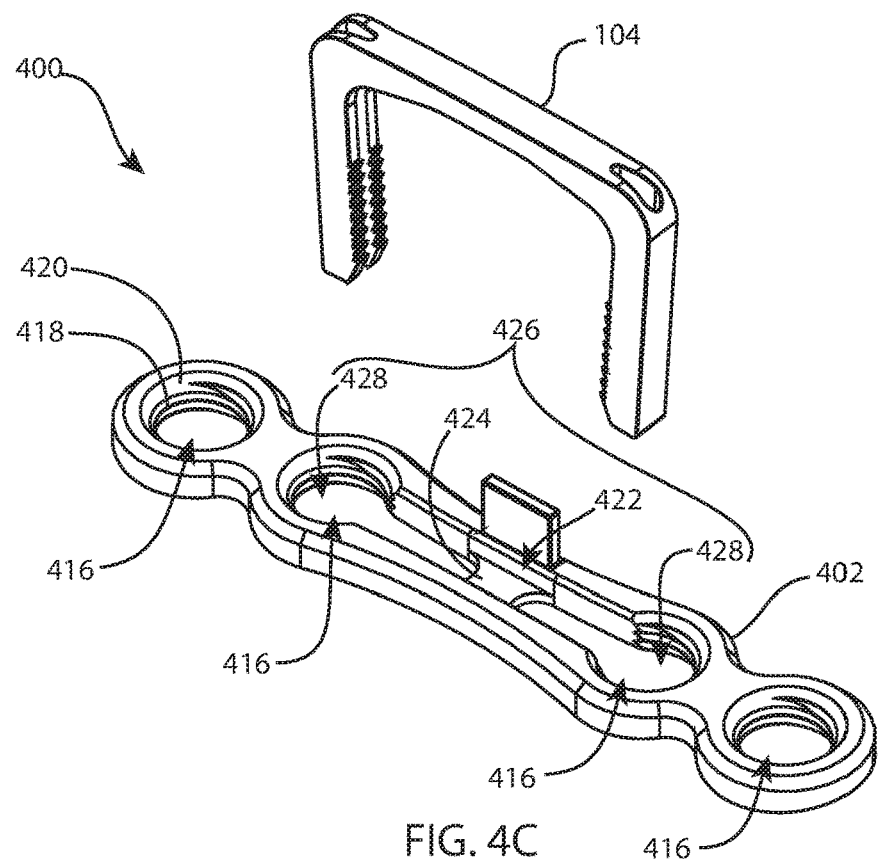
FIG. 4C is an exploded oblique view of the assembly of FIG. 4A; FIG.
Figure 4D:
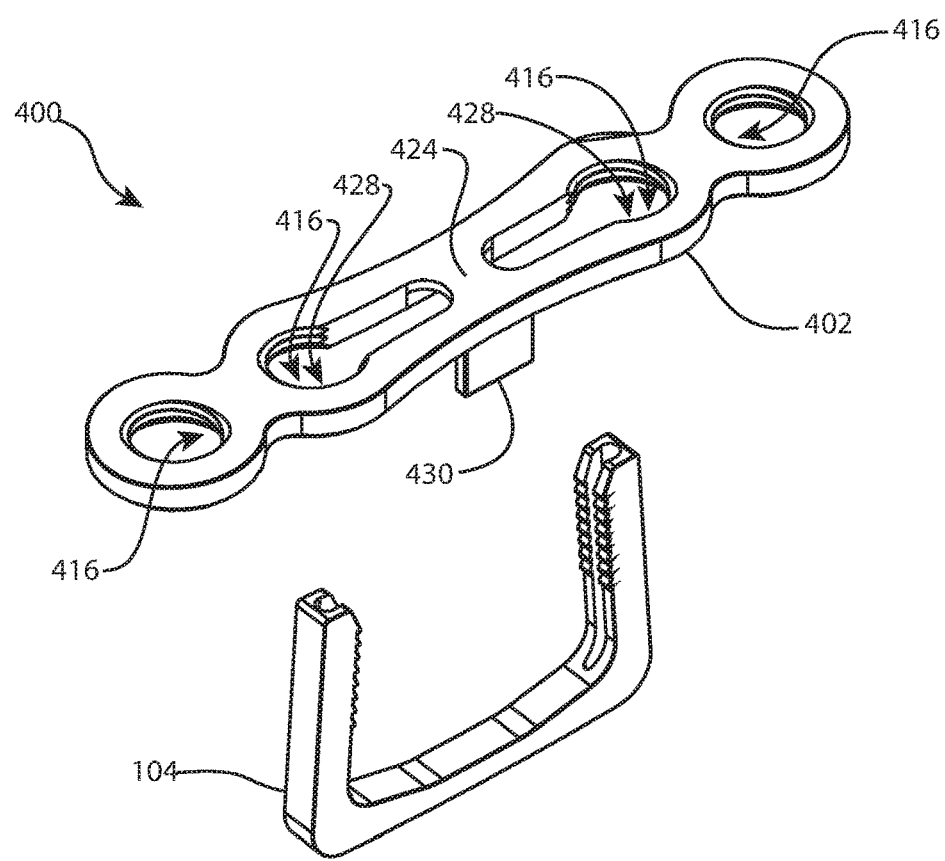
FIG. 4E is yet another oblique view of the assembly of FIG. 4A, showing a tab in a closed configuration.
FIG. 4F is a side view of the assembly of FIG. 4E.
FIG. 4G is a longitudinal cross-section of the assembly of FIG. 4E along a mid-sagittal plane of the bone plate.
Figure 4E:
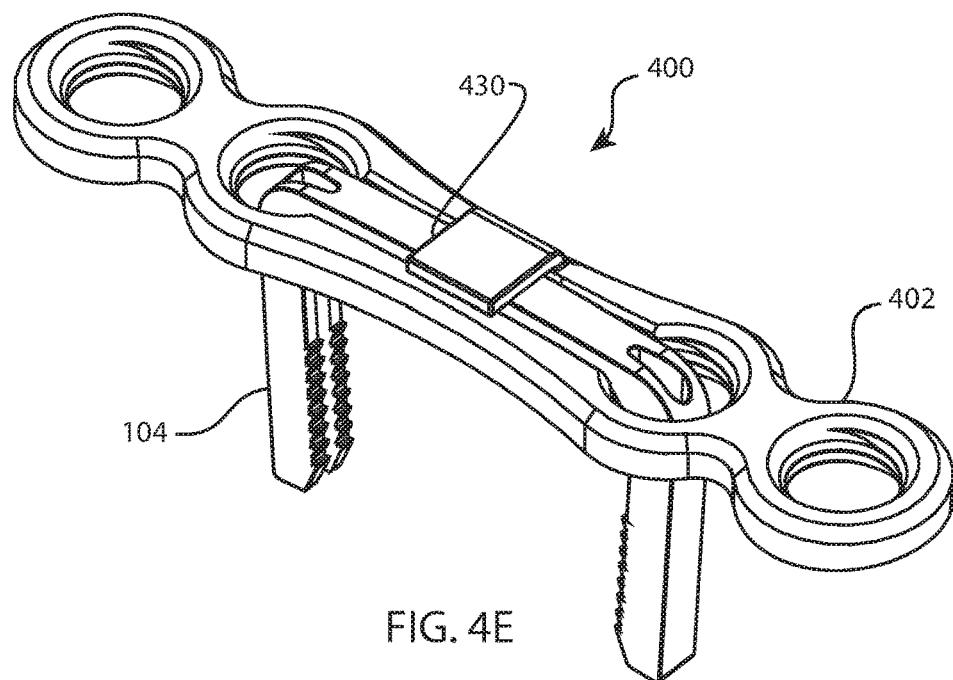
Figure 4F:
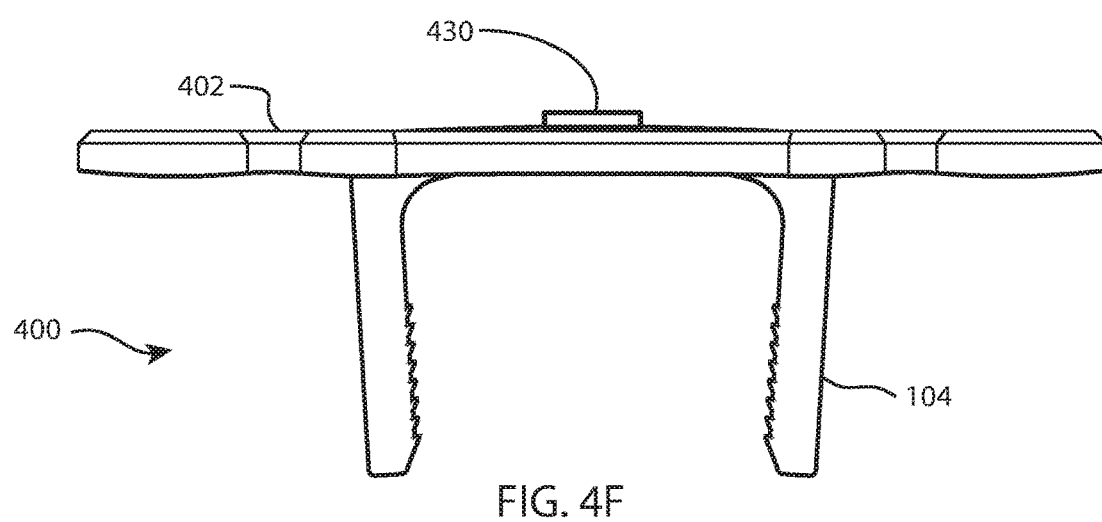
Figure 4G:
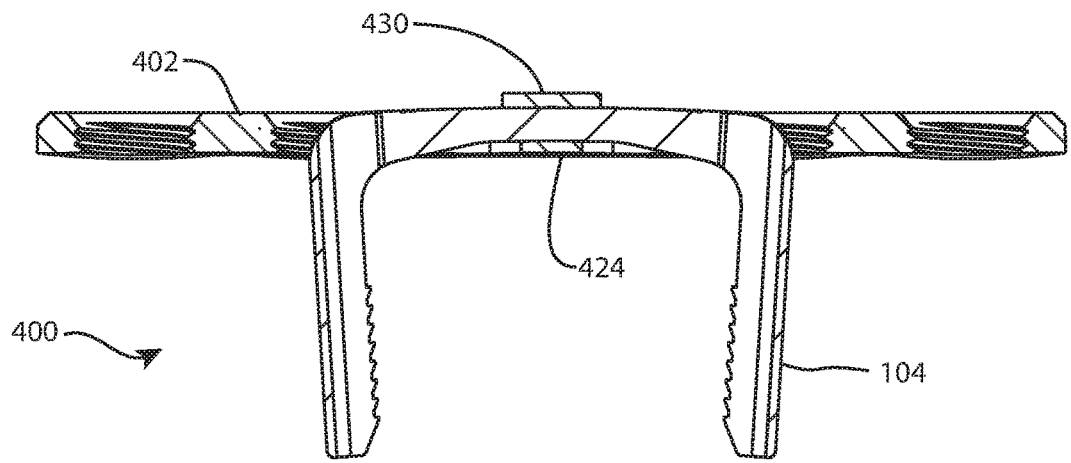
Figure 5A:
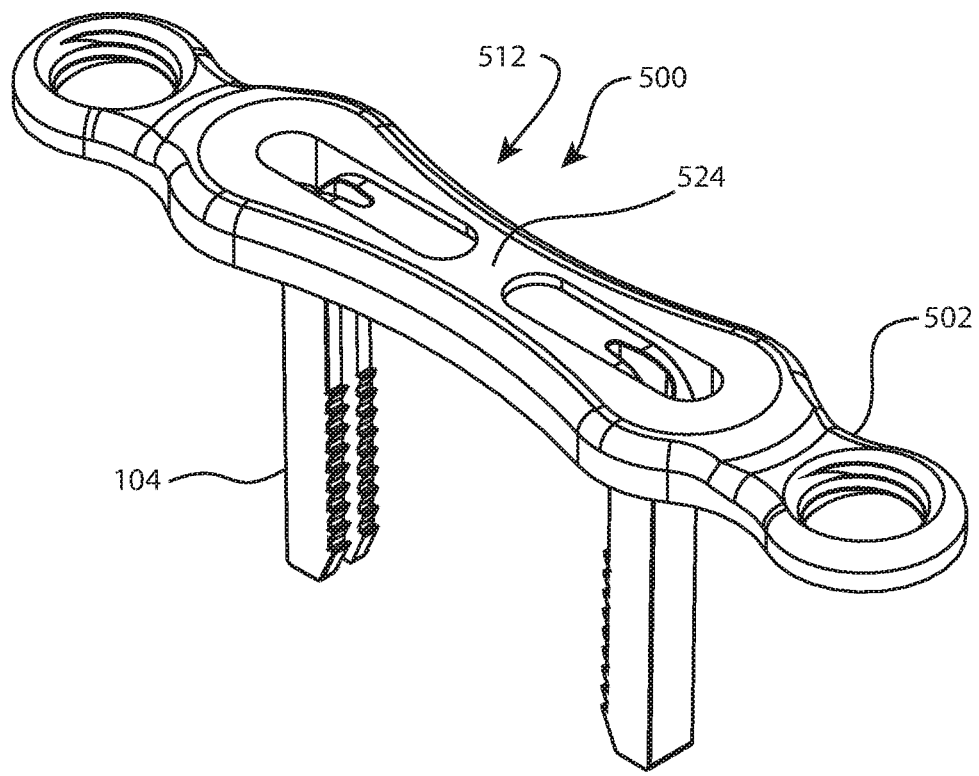
FIG. 5A is an oblique view of an assembly with a bone plate and a staple insert molded within the bone plate.
Figure 5B:
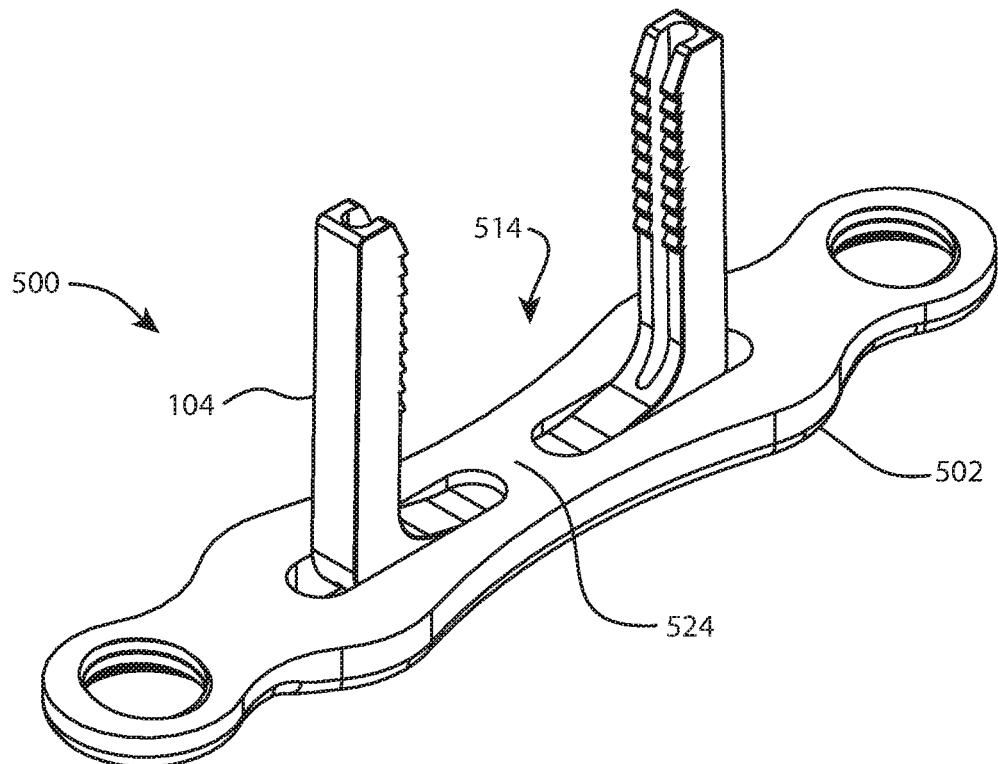
FIG. 5B is another oblique view of the assembly of FIG. 5A from a different direction.
Figure 5C:
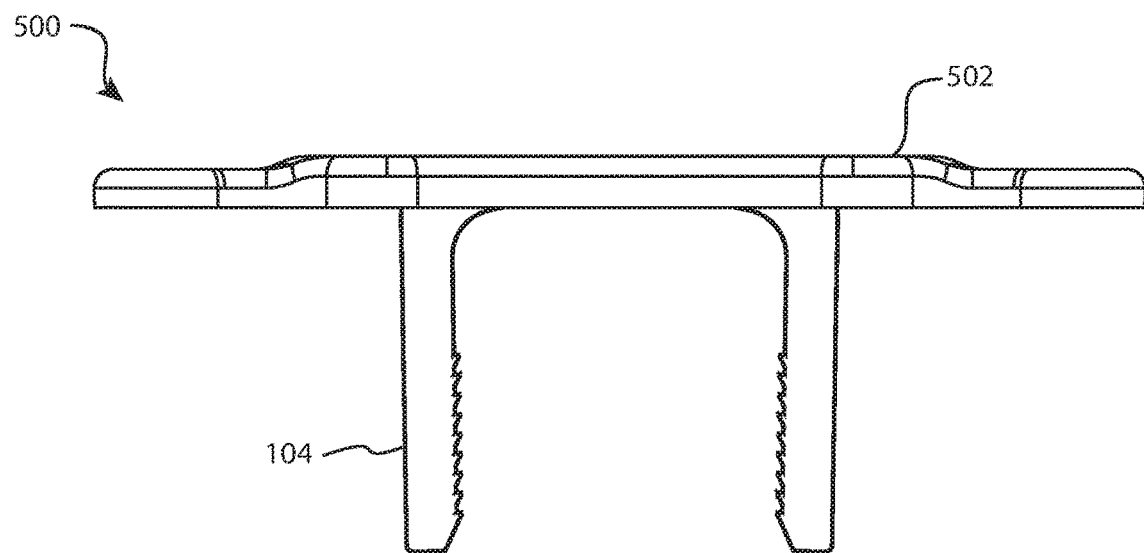
FIG. 5C is a side view of the assembly of FIG. 5A.
Figure 5D:
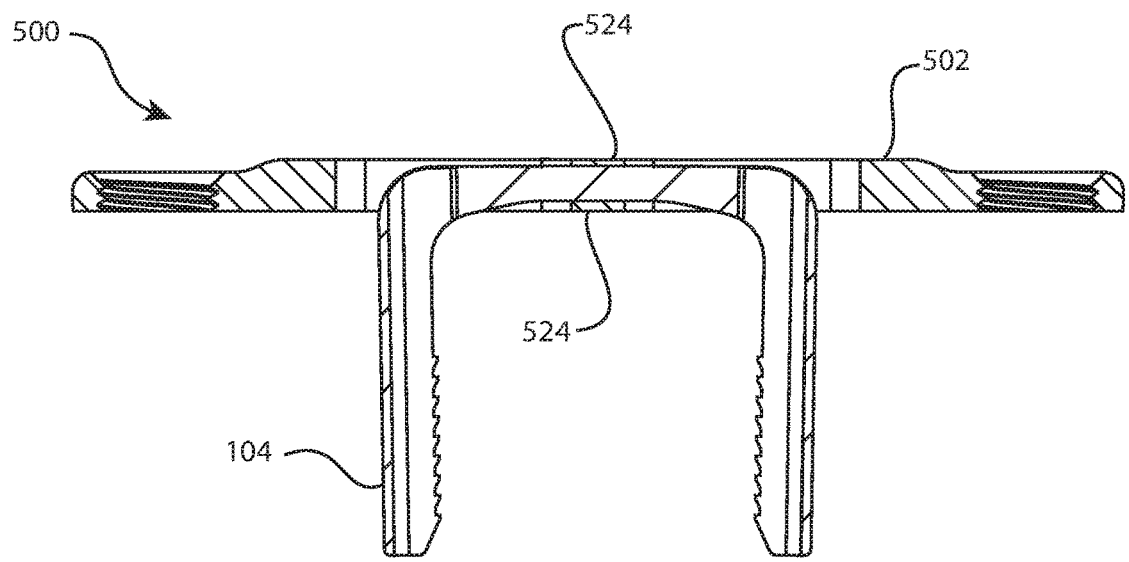
FIG. 5D is a longitudinal cross-section of the assembly of FIG. 5A along a mid-sagittal plane of the bone plate.
Figure 5E:
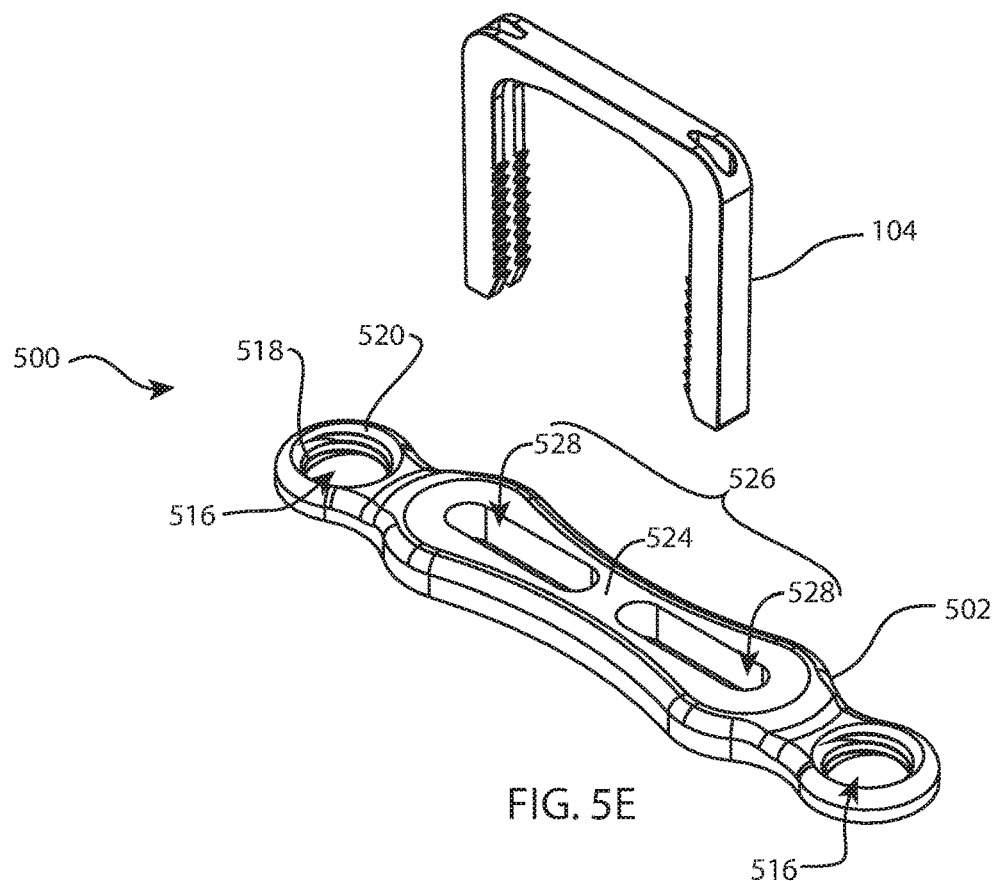
FIG. 5E is an exploded oblique view of the assembly of FIG. 5A.
Figure 5F:
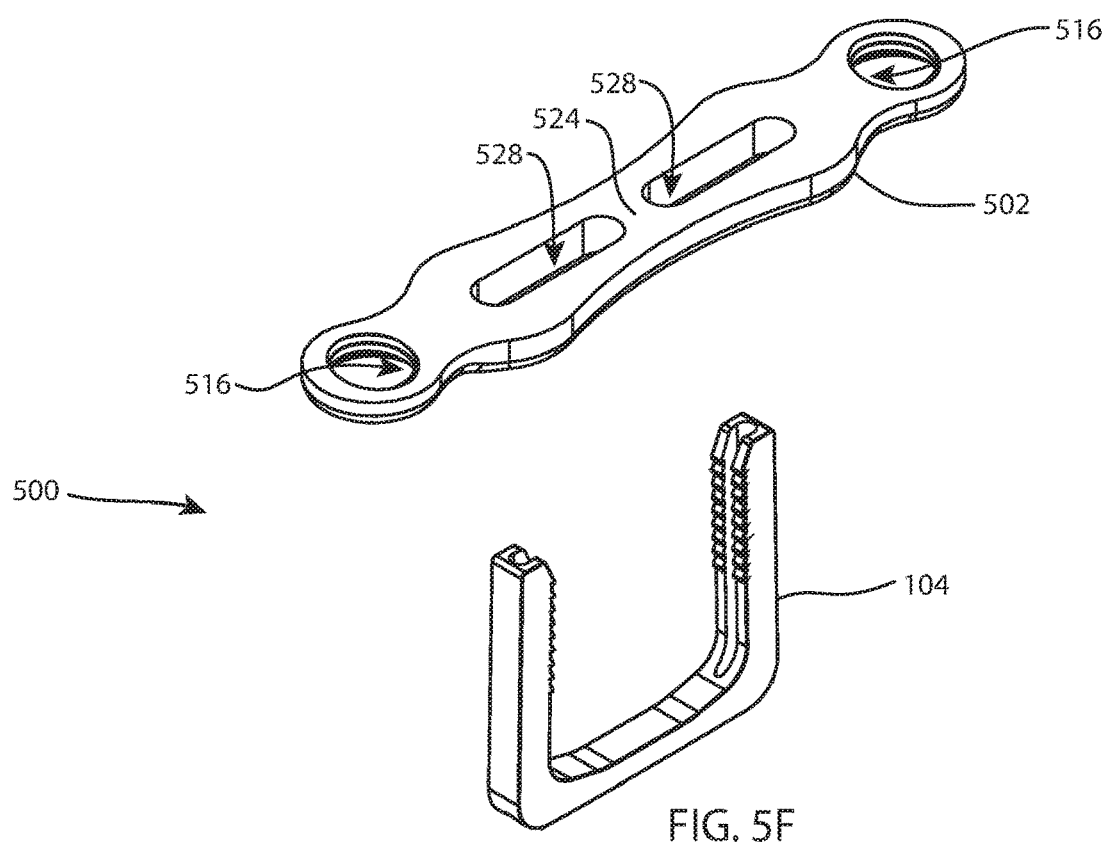
FIG. 5F is another exploded oblique view of the assembly of FIG. 5A from a different direction.
Figure 6A:
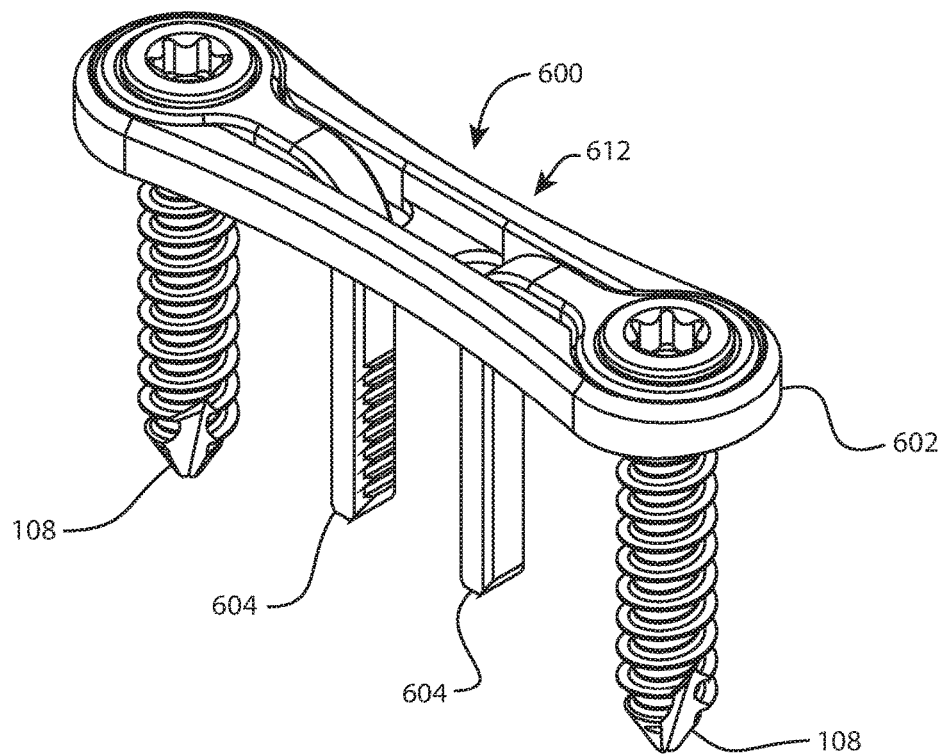
FIG. 6A is an oblique view of an assembly with a bone plate, elbow pegs, and screws.
Figure 6B:
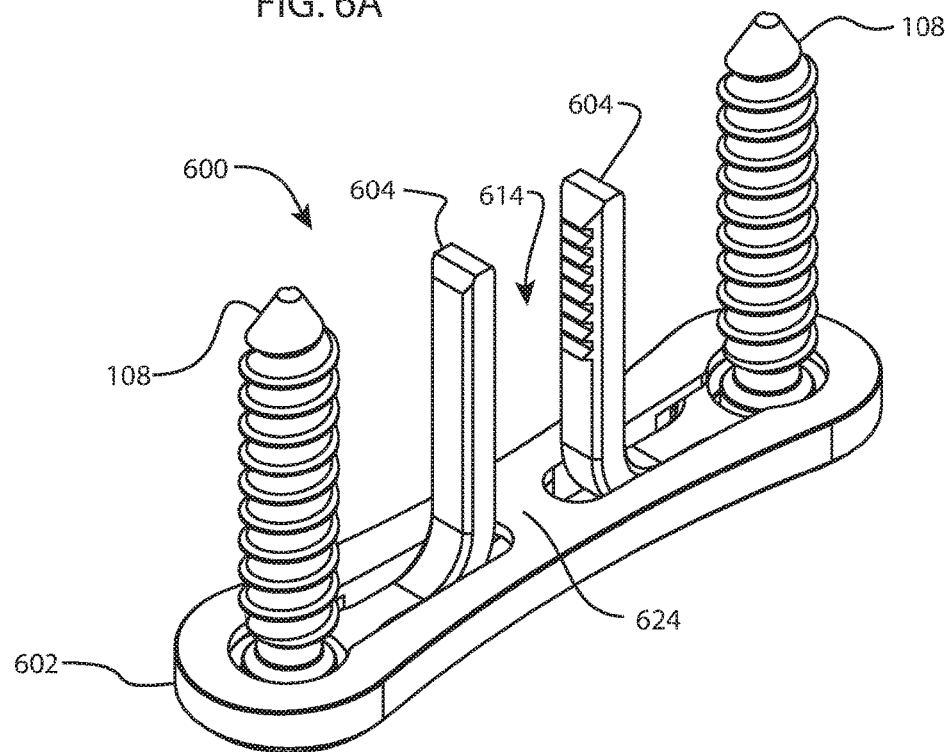
FIG. 6B is another oblique view of the assembly of FIG. 6A from a different direction.
Figure 6C:
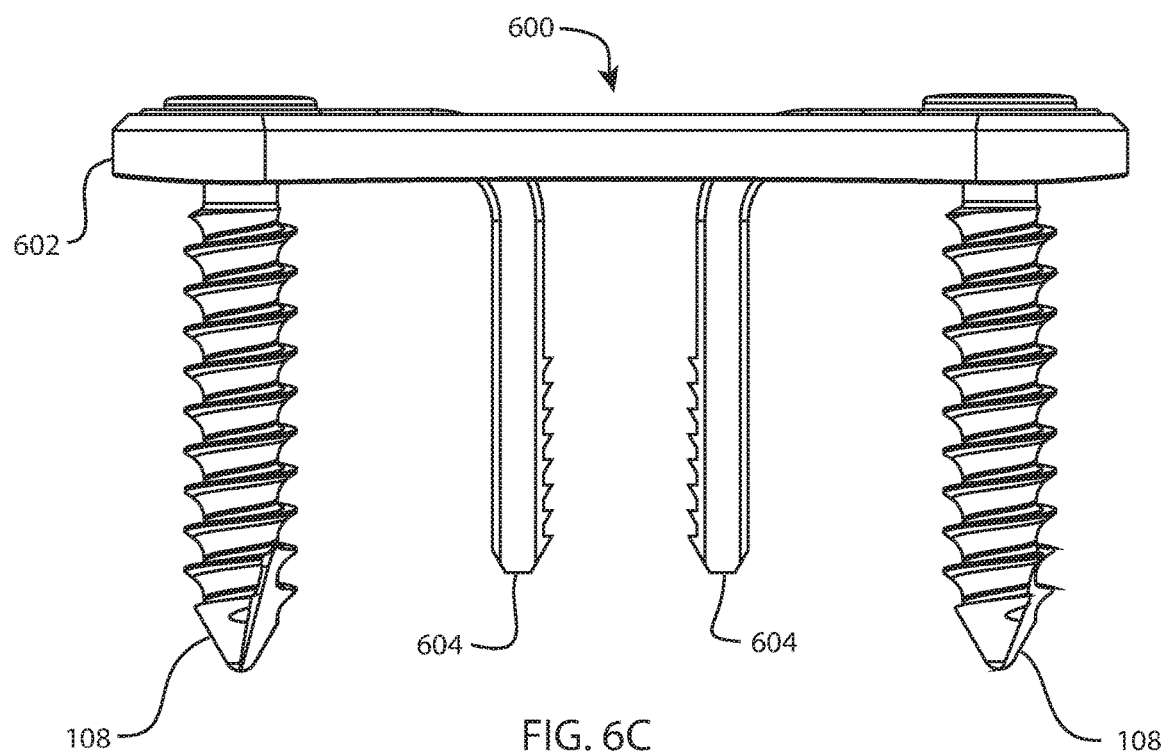
FIG. 6C is a side view of the assembly of FIG. 6A.
Figure 6D:
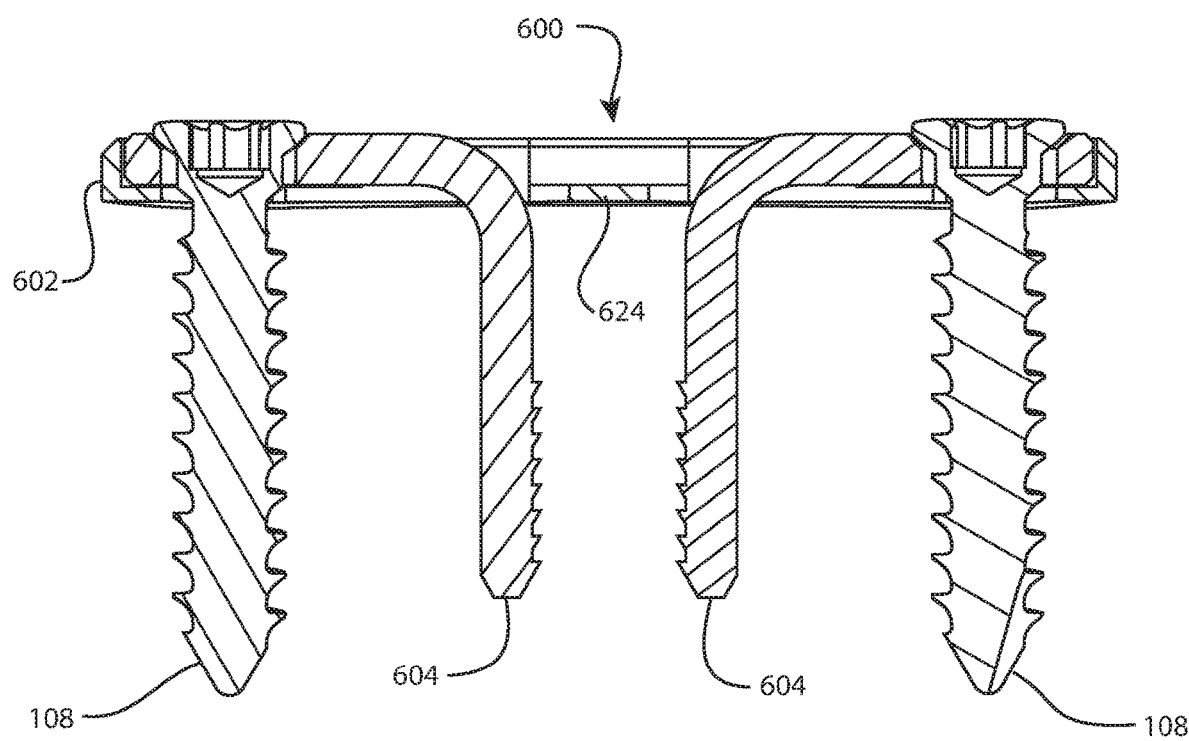
FIG. 6D is a longitudinal cross-section of the assembly of FIG. 6A along a mid-sagittal plane of the bone plate.
Figure 6E:
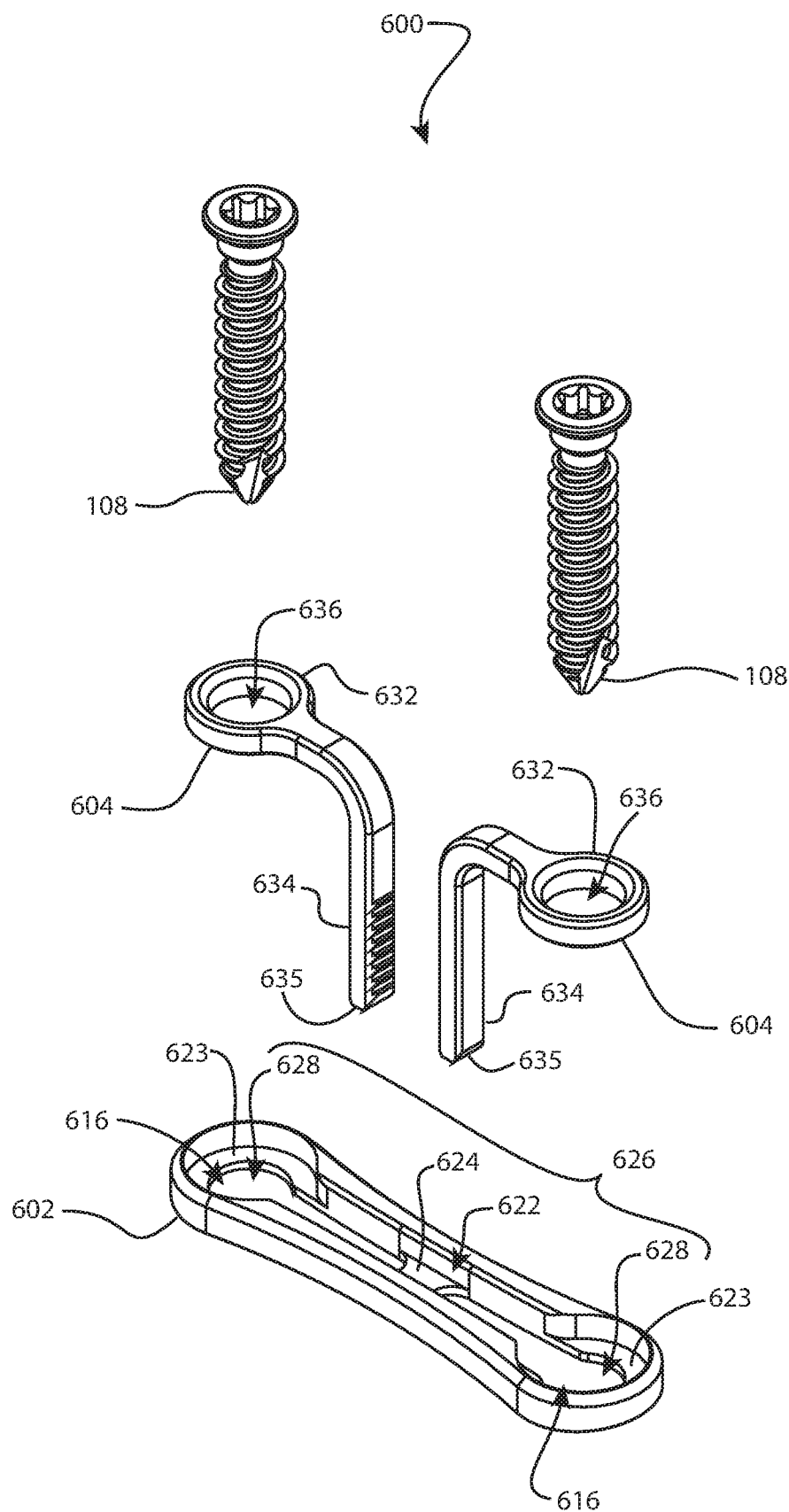
FIG. 6E is an exploded oblique view of the assembly of FIG. 6A.
Figure 6F:
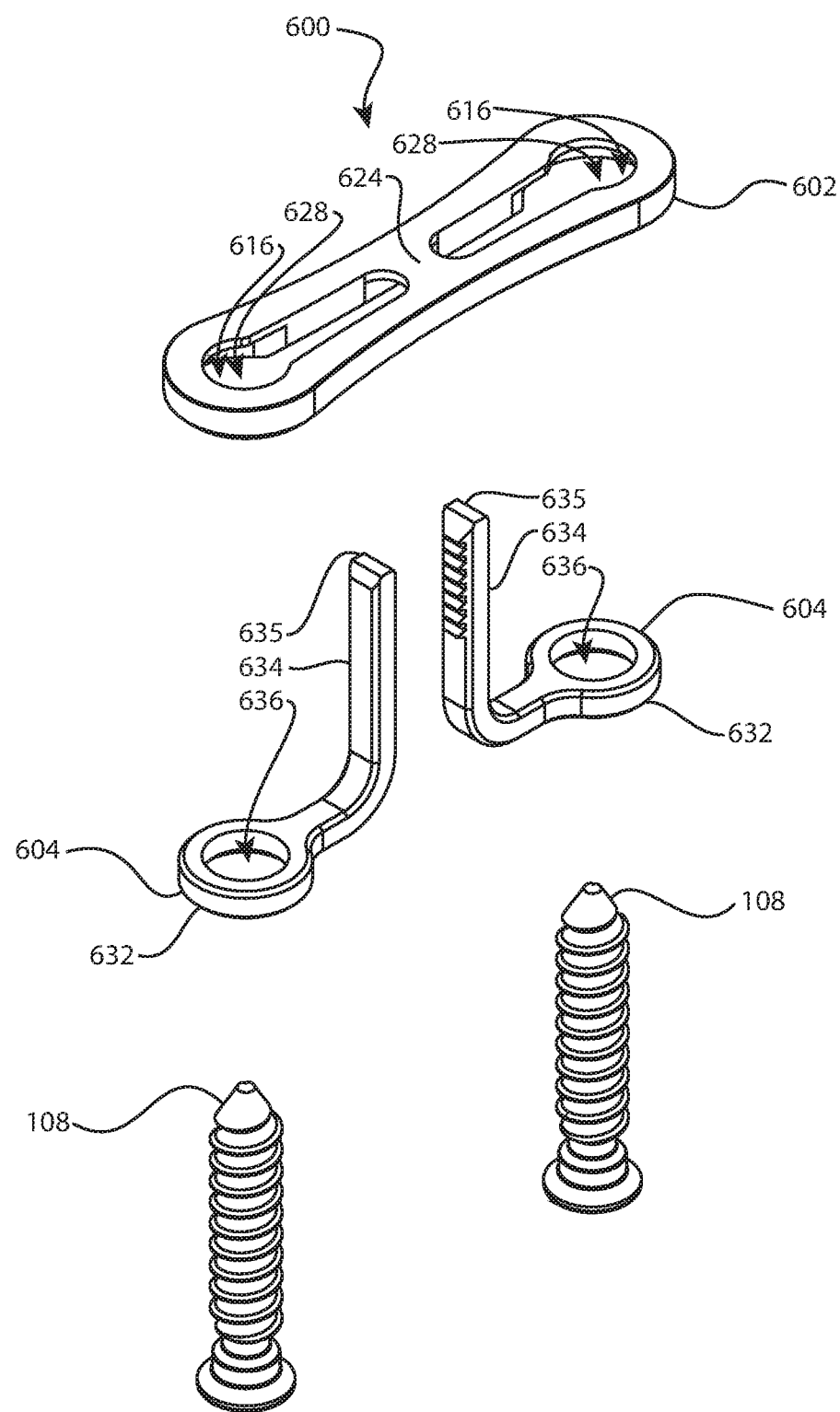
FIG. 6F is another exploded oblique view of the assembly of FIG. 6A from a different direction.

The bone plate 402 has an obverse side 412 and a reverse side 414. The bone plate 402 includes several holes 416, each of which may include an internally threaded portion 418 and a non-threaded portion 420, the same as hole 116. The internally threaded portion 418 may be adjacent to the reverse side 414 and the non-threaded portion 420 may be adjacent to the obverse side 412. An optional groove 422 in the obverse side 412 extends between two of the holes 416. Each of these two holes 416 is also elongated toward the other hole 416, leaving a web 424 extending between the two holes 416. The web 424 may be adjacent to the reverse side 414. The web 424 separates the two holes 416, and may be present even if the holes 416 are not elongated towards each other. The web 424 prevents the body 140 from passing through the reverse side 414. The optional groove 422 if present, the two elongated holes 416, and the web 424 are referred to collectively as a receiver 426, and the involved holes 416 are referred to as receiver holes 428. The bone plate 402 includes a ductile tab 430 that extends from the obverse side 412 beside the receiver 426. There may be more than one tab 430. The tab 430 couples the staple 104 to the bone plate 402. The tab 430 may therefore be considered one of the fasteners, and may be referred to as a locking mechanism. The tab 430 is illustrated in an open state in FIGS. 4A-4D, and in a closed state in FIGS. 4E-4G. In the open state, the staple 104 may be inserted into the receiver 426. In the closed state, the tab 430 prevents the staple 104 from being removed from the receiver. The tab 430 may be bent over the staple 104 in the closed state. The tab 430 may experience plastic deformation, also known as permanent deformation, so that the tab 430 remains bent over the staple 104 unless bent back towards the open state. The tab 430 may be closed intraoperatively, or the assembly 400 may be provided coupled together with the tab 430 closed as shown in FIGS. 4E-4G.

Other means for locking the staple 104 to a bone plate are contemplated, such as a snap fit between the staple 104 and the bone plate (not shown).

Referring to FIGS. 5A-5F, an assembly 500 may include a stabilizing member, a dynamic element, and one or more fasteners. In assembly 500, the stabilizing member may be a bone plate 502, the dynamic element may be the staple 104, and the fasteners may be one or more of the screws 106 and/or 108, although the screws 106 and 108 are omitted from the illustration for clarity.

The bone plate 502 has an obverse side 512 and a reverse side 514. The bone plate 502 includes several holes 516, each of which may include an internally threaded portion 518 and a non-threaded portion 520, the same as hole 116. The internally threaded portion 518 may be adjacent to the reverse side 514 and the non-threaded portion 520 may be adjacent to the obverse side 512. Two of the holes 516 are elongated toward each other, leaving a web 524 extending between the two holes 516. The two elongated holes 516 in this example lack the internally threaded portion 518. The web 524 may be adjacent to the reverse side 514. The web 524 separates the two holes 516, and may be present even if the holes 516 are not elongated towards each other. The web 524 prevents the body 140 from passing through the reverse side 514. The two elongated holes 516 and web 524 are referred to collectively as a receiver 526, and the involved holes 516 are referred to as receiver holes 528. In this example, the bone plate 502 is formed around the staple 104 at least partially so that the staple 104 is inseparable from the bone plate 502 in normal use. The web 524 encircles a middle portion of the body 140 of the staple 104, leaving lateral portions of the staple body 140 and the staple legs 142, 144 free to flex between the relaxed state and the elastically deformed state. Alternately, the staple 104 may be partially or fully encapsulated in an elastically deformable material that bends with the staple as the staple moves between the relaxed state and the elastically deformed state. The bone plate 502 may be made of polyetheretherketone (PEEK) which is overmolded around the staple 104. The staple 104 may be insert molded into the bone plate 502. The bone plate 502 and staple 104 may be integrally formed of a single material, preferably a highly elastic material such as nitinol. The staple included in assembly 500 may be a modified version of staple 104. The modifications may facilitate manufacturing the bone plate 502 and the staple as a unit.

Referring to FIGS. 6A-6F, an assembly 600 may include a stabilizing member, a dynamic element, and one or more fasteners. In assembly 600, the stabilizing member may be a bone plate 602, the dynamic element may be an elbow peg 604 also known as an L-peg, and the fasteners may be one or more of the screws 106 and/or 108.

The bone plate 602 has an obverse side 612 and a reverse side 614. The bone plate 602 includes several holes 616. The holes 616 may lack an internally threaded portion like hole 116. A groove 622 in the obverse side 612 extends between two of the holes 616 and within the holes, forming a shelf 623 within each hole 616. The shelf 623 may be adjacent to the reverse side 614. Each of these two holes 616 is also elongated toward the other hole 616, leaving a web 624 extending between the two holes 616. The web 624 may be adjacent to the reverse side 614. The web 624 separates the two holes 616, and may be present even if the holes 616 are not elongated towards each other. The groove 622, two elongated holes 616, and web 624 are referred to collectively as a receiver 626, and the holes 616 are referred to as receiver holes 628, since these features receive the elbow pegs 604.

Two elbow pegs 604 are shown facing each other in the assembly 600. In this example, the elbow pegs 604 take the place of the previous dynamic element, the staple 104. Each elbow peg 604 includes a head 632 and a bone-contacting leg 634, which terminates in a free end 635. The head 632 may be shaped like a ring, as illustrated, or it may be any shape, such as rectangular, square, oval, polygonal, etc. The head 632 may be perpendicular, or nearly perpendicular, to the leg 634. For example, the head 632 and the leg 634 may form an angle of 90 degrees±10 degrees, 90 degrees±15 degrees, or 90 degrees±20 degrees. Alternatively, the head 632 may form an acute angle or an obtuse angle with the leg 634. Each elbow peg 604 may be independently inserted into a bone hole and secured to the bone plate 602. The elbow peg 604 may be secured to the bone plate 602 by a bone screw, such as screw 106 or 108, through an aperture 636 through the head 632. The shelf 623 prevents the head 632 from passing through the reverse side 614 of the bone plate 602. The elbow peg 604 may develop some spring force as the bone screw is fully seated, as explained more fully below with regard to assembly 700. The spring force may be linear or nonlinear. The elbow peg 604 may exert force due to simple leverage without substantive spring force.

While two elbow pegs 604 are shown, a single elbow peg 604 may be used opposite a locking screw 106. This arrangement is not shown. In this case, the bone plate 602 would have an internally threaded hole 616 at one end (like hole 116 of bone plate 102) and at the other end, a receiver hole 628. The assembly would include a locking screw 106 in the internally threaded hole 616 and an elbow peg 604 plus a screw in the receiver hole 628.

In a further modification of assembly 600, a screw 108 and an elbow peg 604 may be used together with no other apparatus. In this case, the screw 108 and the leg 634 of the elbow peg 604 may lie on opposite sides of the discontinuity between tissue portions. A screw 106 may also be used in this fashion, in which case the aperture 636 through the head 632 of the elbow peg 604 preferably includes an internally threaded portion to engage the external threads 119 on the head 107 of the screw 106.

Referring to FIGS. 7A-7F, an assembly 700 may include a stabilizing member, a dynamic element, and one or more fasteners. In assembly 700, the stabilizing member may be a bone plate 702, the dynamic element may be an elbow peg 704 also known as an L-peg, and the fasteners may be one or more of the set screws 310.

The bone plate 702 has an obverse side 712 and a reverse side 714. The bone plate 702 includes several holes 716, each of which may include an internally threaded portion 718. The internally threaded portion 718 may be adjacent to the obverse side 712. Each hole 716 may include an interior shelf 723. The shelf 723 may be adjacent to the reverse side 714. Two of the holes 716 are elongated toward each other, leaving a web 724 extending between the two holes 716. The web 724 may be adjacent to the reverse side 714. The web 724 separates the two holes 716, and may be present even if the holes 716 are not elongated towards each other. The two elongated holes 716 and web 724 are referred to collectively as a receiver 726, and the involved holes 716 are referred to as receiver holes 728, since these features receive the elbow pegs 704.

Figure 7A:
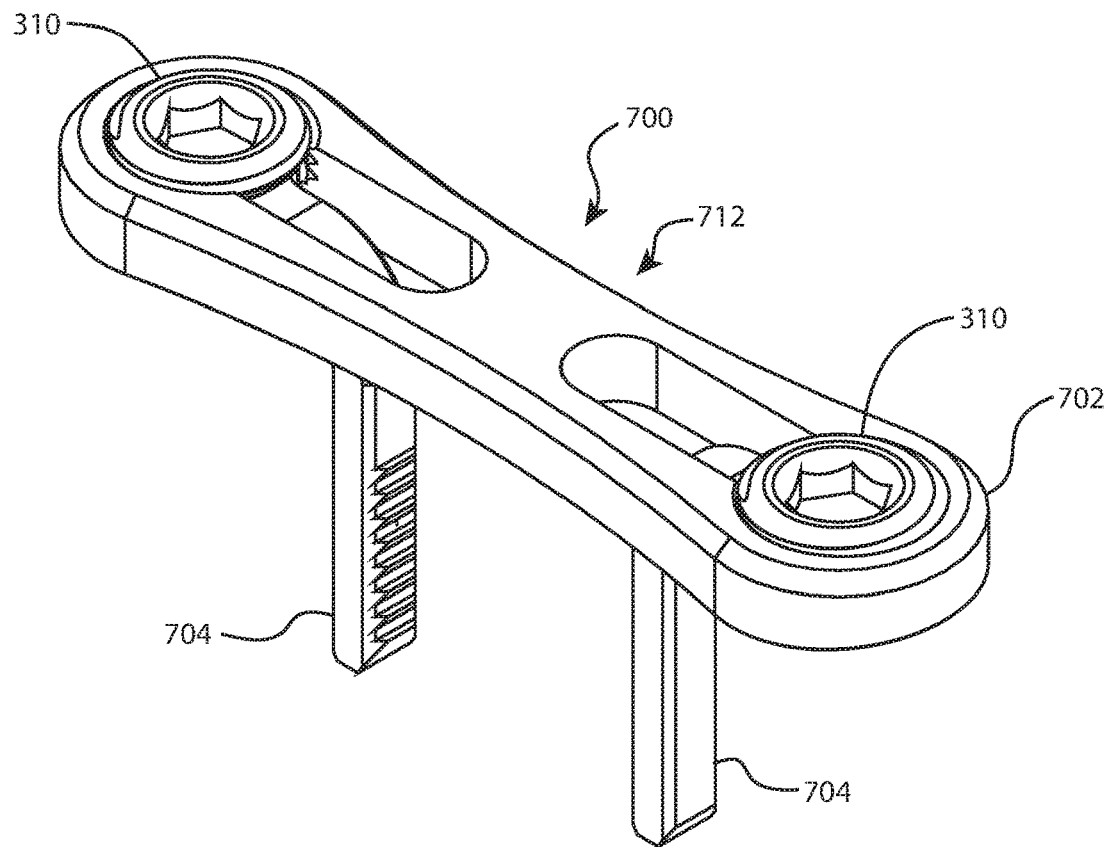
FIG. 7A is an oblique view of an assembly with a bone plate, elbow pegs, and set screws.
Figure 7B:
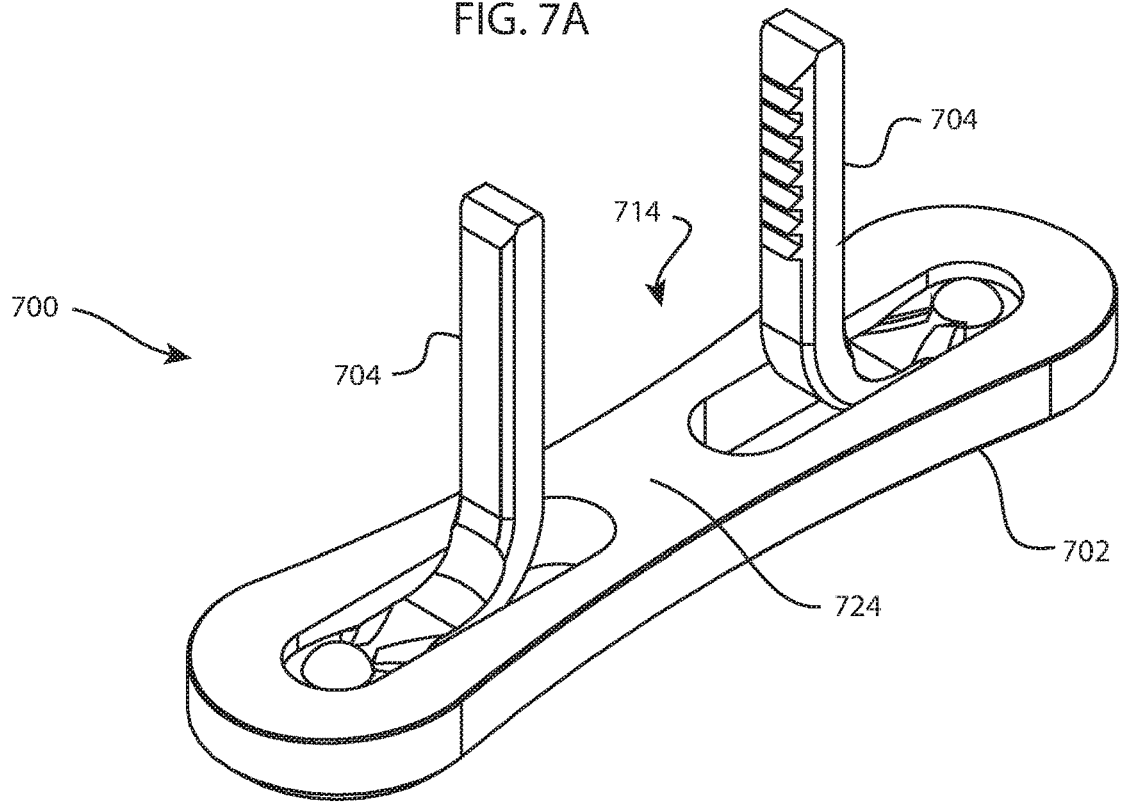
FIG. 7B is another oblique view of the assembly of FIG. 7A from a different direction.
Figure 7C:
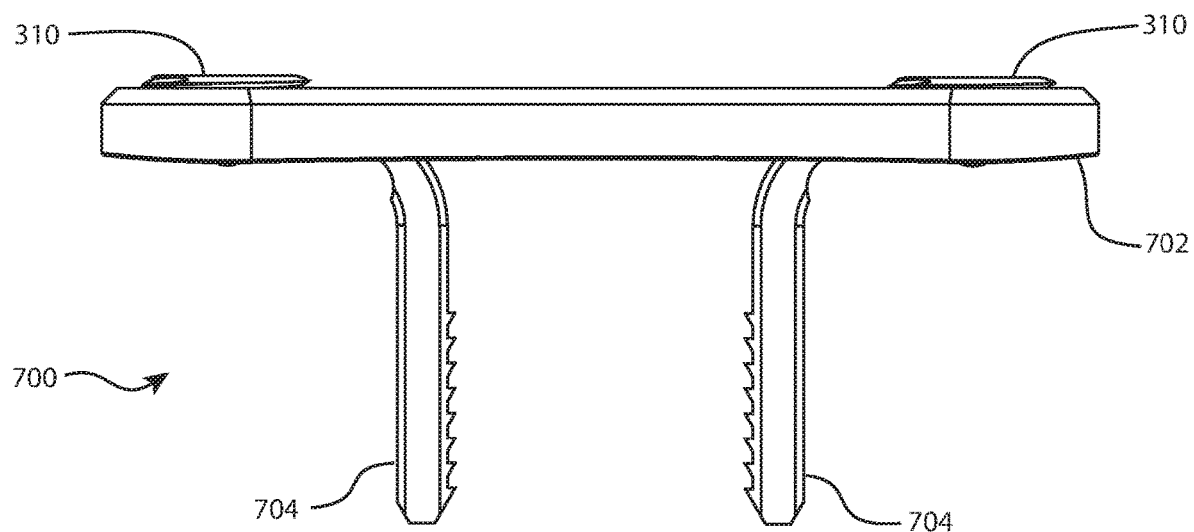
FIG. 7C is a side view of the assembly of FIG. 7A.
Figure 7D:
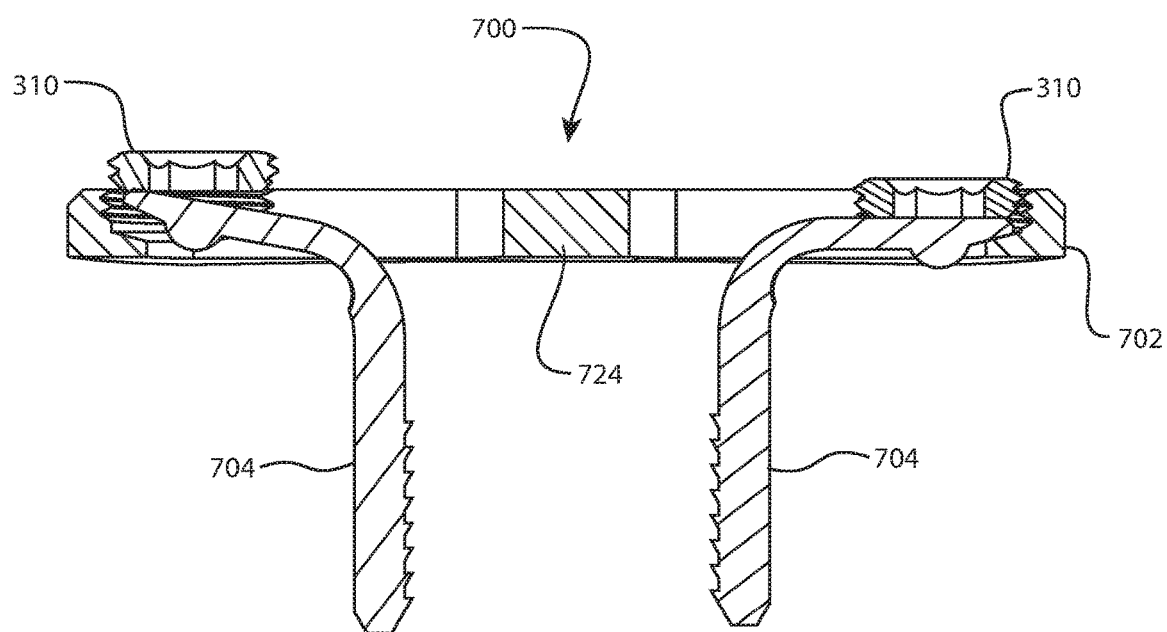
FIG. 7D is a longitudinal cross-section of the assembly of FIG. 7A along a mid-sagittal plane of the bone plate, showing one of the elbow pegs in an insertion configuration and another one of the elbow pegs in a final configuration.
Figure 7E:
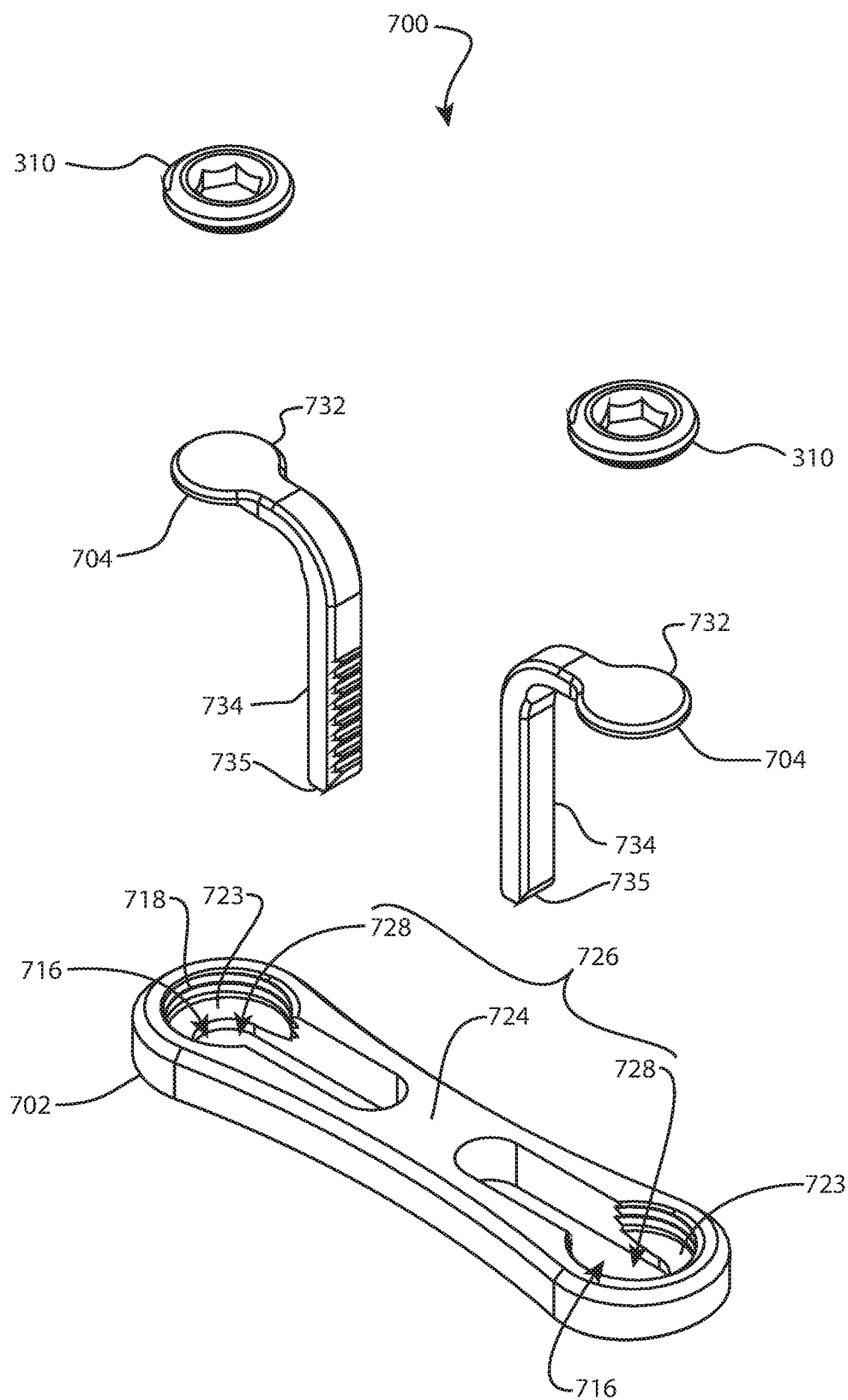
FIG. 7E is an exploded oblique view of the assembly of FIG. 7A.
Figure 7F:
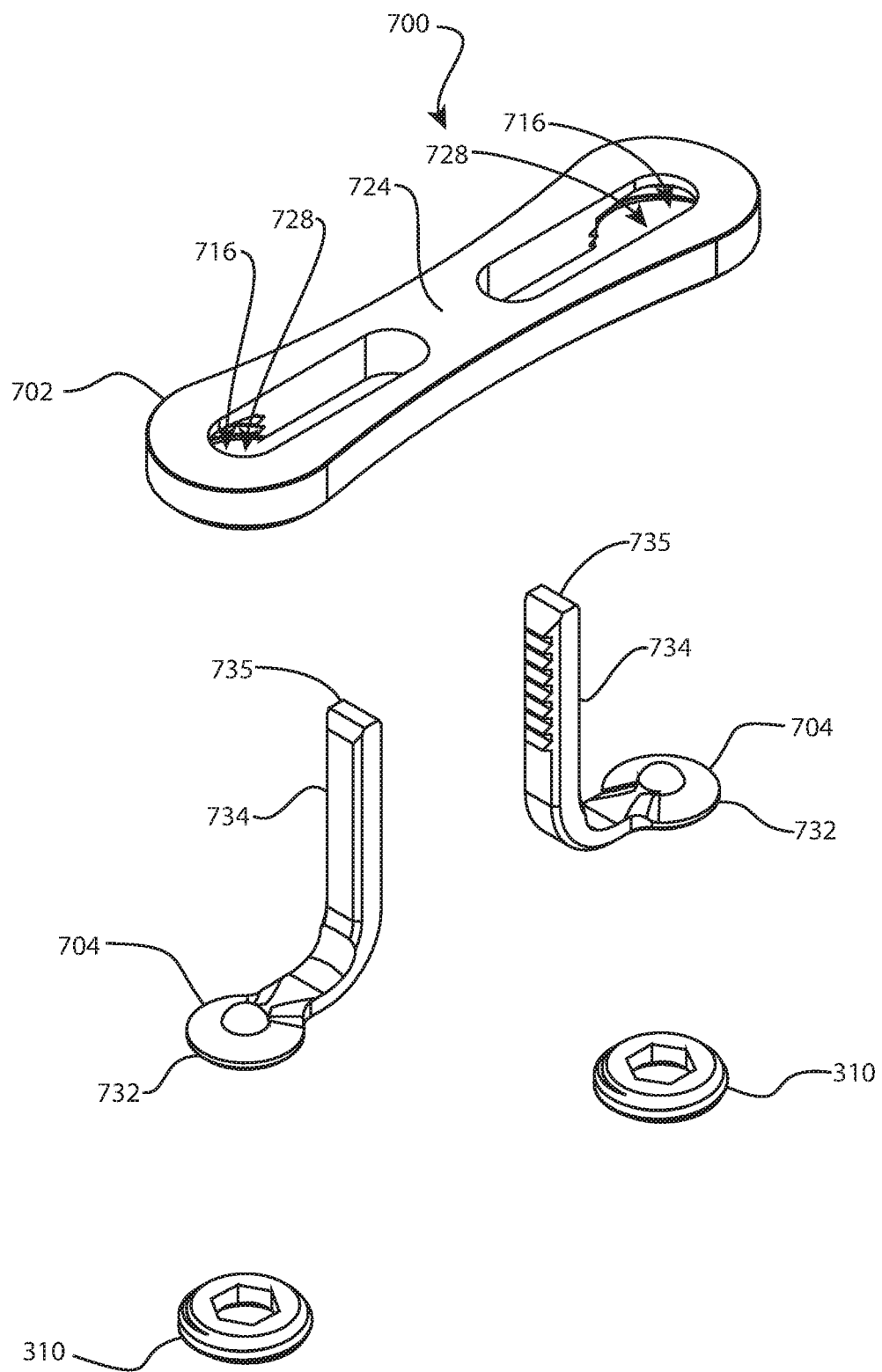
FIG. 7F is another exploded oblique view of the assembly of FIG. 7A from a different direction.

Two elbow pegs 704 are shown facing each other in the assembly 700. In this example, the elbow pegs 704 take the place of the previous dynamic element, the staple 104. Each elbow peg 704 includes a head 732 and a bone-contacting leg 734, which terminates in a free end 735. The head 732 may be rounded, as illustrated, or it may be any shape. The head 732 may be perpendicular, or nearly perpendicular, to the leg 734. For example, the head 732 and the leg 734 may form an angle of 90 degrees±10 degrees, 90 degrees±15 degrees, or 90 degrees±20 degrees. Alternatively, the head 732 may form an acute angle or an obtuse angle with the leg 734. Each elbow peg 704 may be independently inserted into a bone hole and secured to the bone plate 702. The elbow peg 704 may be secured to the bone plate 702 by the set screw 310 against the head 734. The shelf 723 prevents the head 732 from passing through the reverse side 714 of the bone plate 702. The elbow peg 704 may develop some spring force as the set screw 310 is fully seated. FIG. 7D shows a free state elbow peg 704 in the left hole. The head 732 and the leg 734 form an obtuse angle in the free state. A compressed elbow peg 704 is shown in the right hole. As a result of driving the set screw 310 tightly against the head 732, the elbow peg 704 is elastically bent to a 90 degree state, which is an elastically deformed state. The leg 734 exerts a force against the bone, acting toward the left-hand elbow peg 704. The force may be linear or nonlinear. A similar principle may apply to the elbow pegs 604 described for assembly 600. The elbow peg 704 may exert force due to simple leverage without substantive spring force.

While two elbow pegs 704 are shown, a single elbow peg 704 may be used opposite a locking screw 106. This arrangement is not shown. In this case, the bone plate would have an internally threaded hole 716 at one end (like hole 116 of bone plate 102) and at the other end, a receiver hole 728. The assembly would include a locking screw 106 in the internally threaded hole 716 and an elbow peg 704 plus a set screw 310 in the receiver hole 728.

Referring to FIGS. 8A-8G, an assembly 800 may include a stabilizing member, a dynamic element, and one or more fasteners. In assembly 800, the stabilizing member may be a bone plate 802, the dynamic element may be a straight peg 804, and the fasteners may be one or more of the set screws 310.

The bone plate 802 has an obverse side 812 and a reverse side 814. The bone plate 802 includes several holes 816, each of which may include an internally threaded portion 818. The internally threaded portion 818 may be adjacent to the obverse side 812. Each hole 816 may include an interior shelf 823. The shelf 823 may be adjacent to the reverse side 814. A web 824 extends between two of the holes 816. The web 824 may be adjacent to the reverse side 814. The web 824 separates the two holes 816, and may be present even if the holes 816 are elongated towards each other. The two holes 816 are referred to as receiver holes 828, since these features receive the straight pegs 804.

Figure 8A:
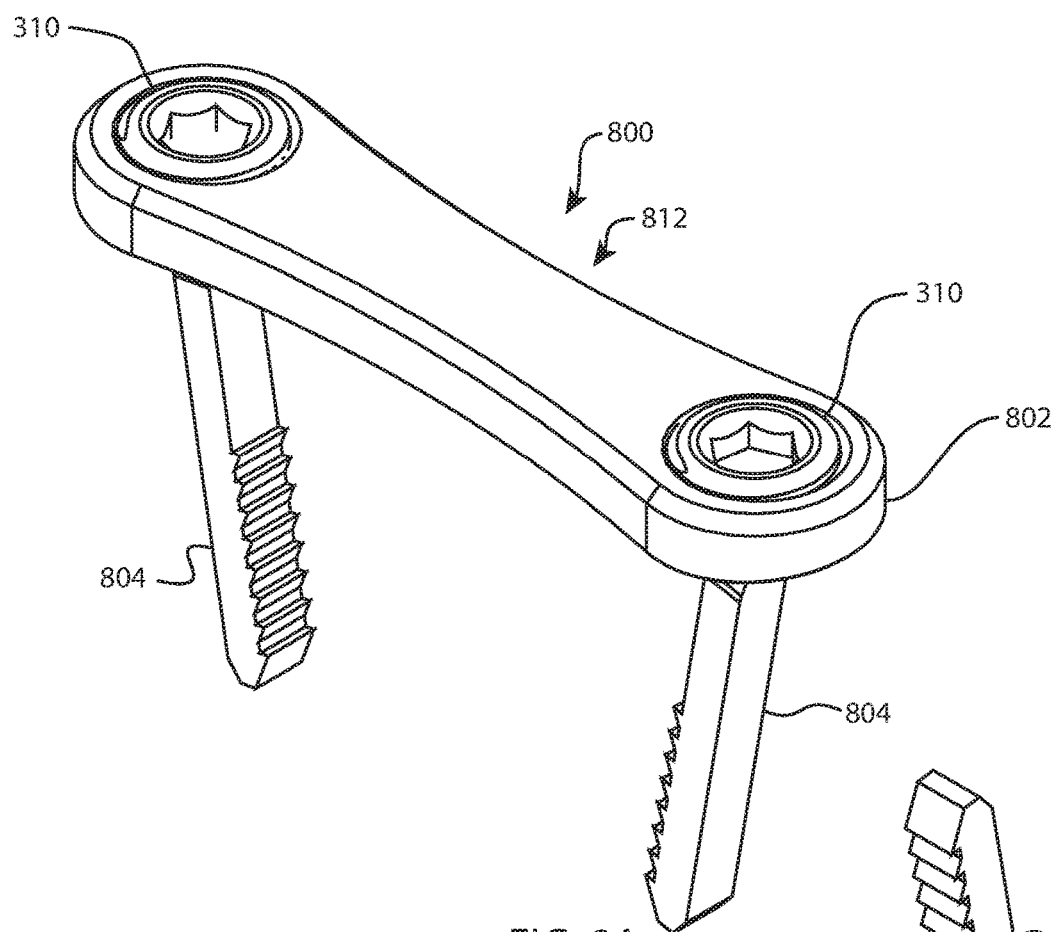
FIG. 8A is an oblique view of an assembly with a bone plate, straight pegs, and set screws.
Figure 8B:
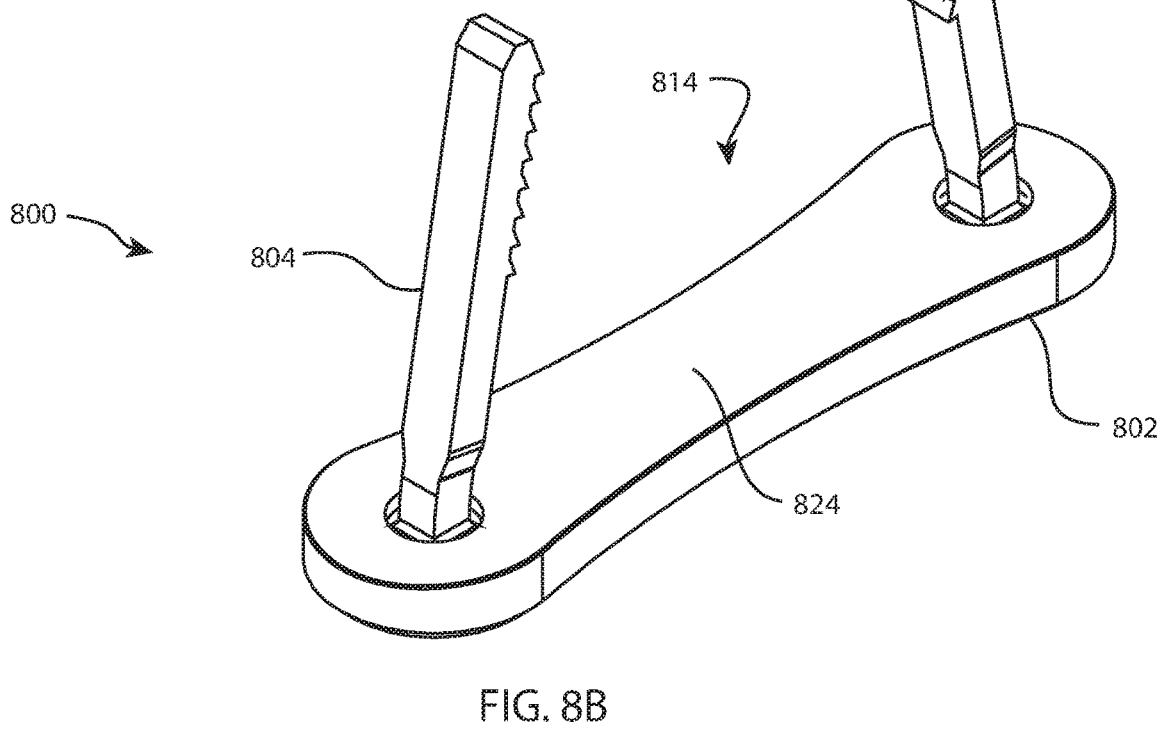
FIG. 8B is another oblique view of the assembly of FIG. 8A from a different direction.
Figure 8C:
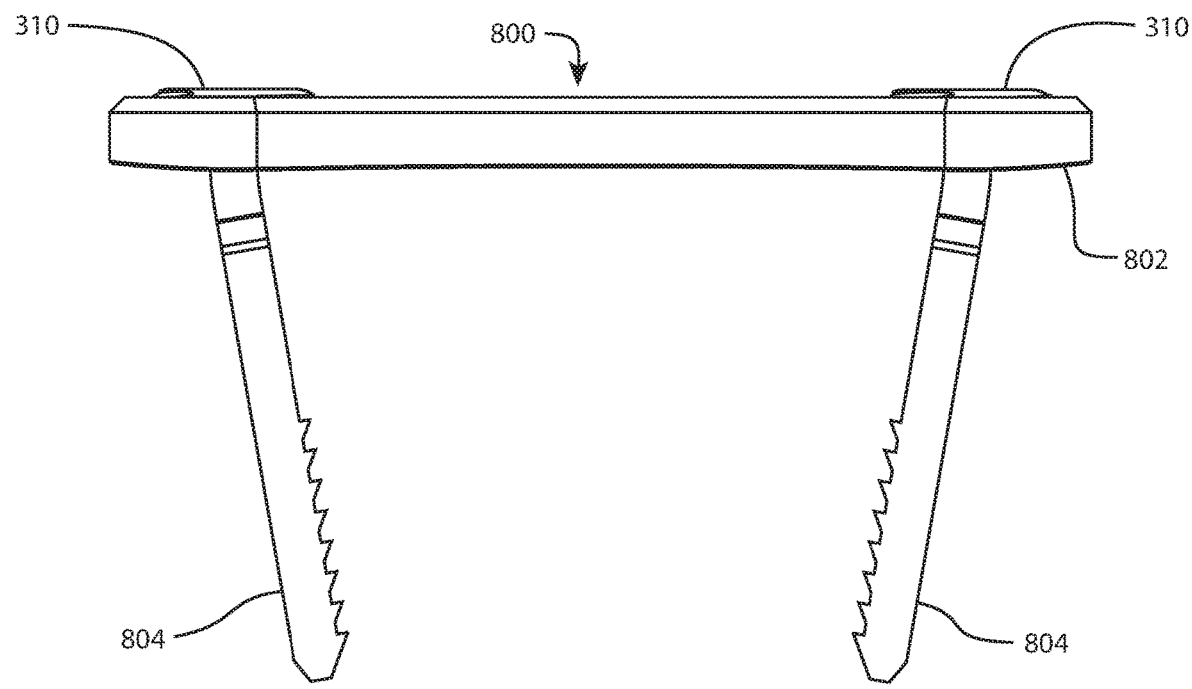
FIG. 8C is a side view of the assembly of FIG. 8A.
Figure 8D:
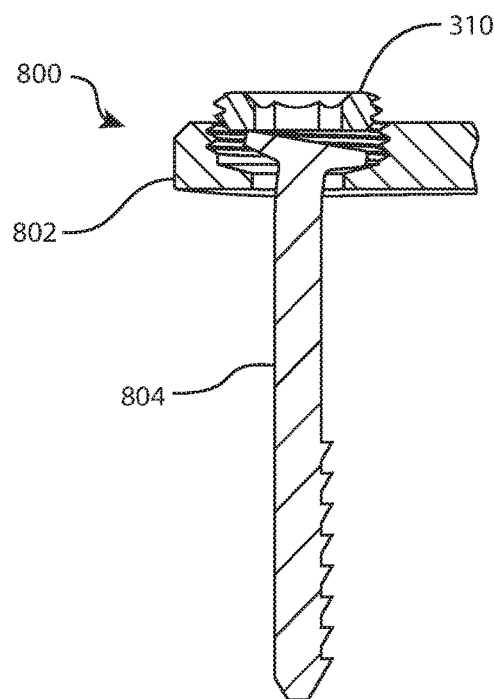
FIG. 8D is a longitudinal cross-section of a portion of the assembly of FIG. 8A along a mid-sagittal plane of the bone plate, showing one of the straight pegs in an insertion configuration.
Figure 8E:
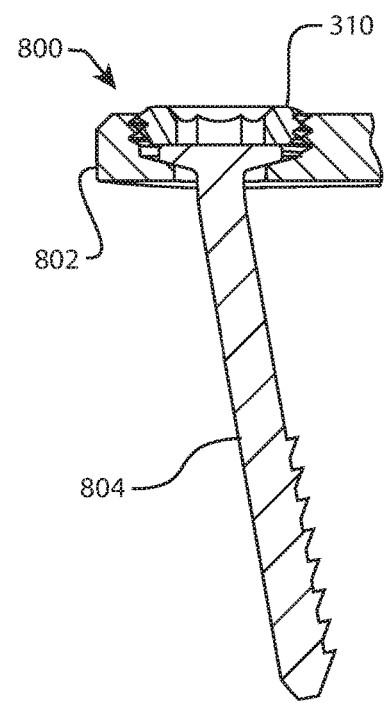
FIG. 8E is a longitudinal cross-section of a portion of the assembly of FIG. 8A along a mid-sagittal plane of the bone plate, showing another one of the straight pegs in a final configuration.
Figure 8F:
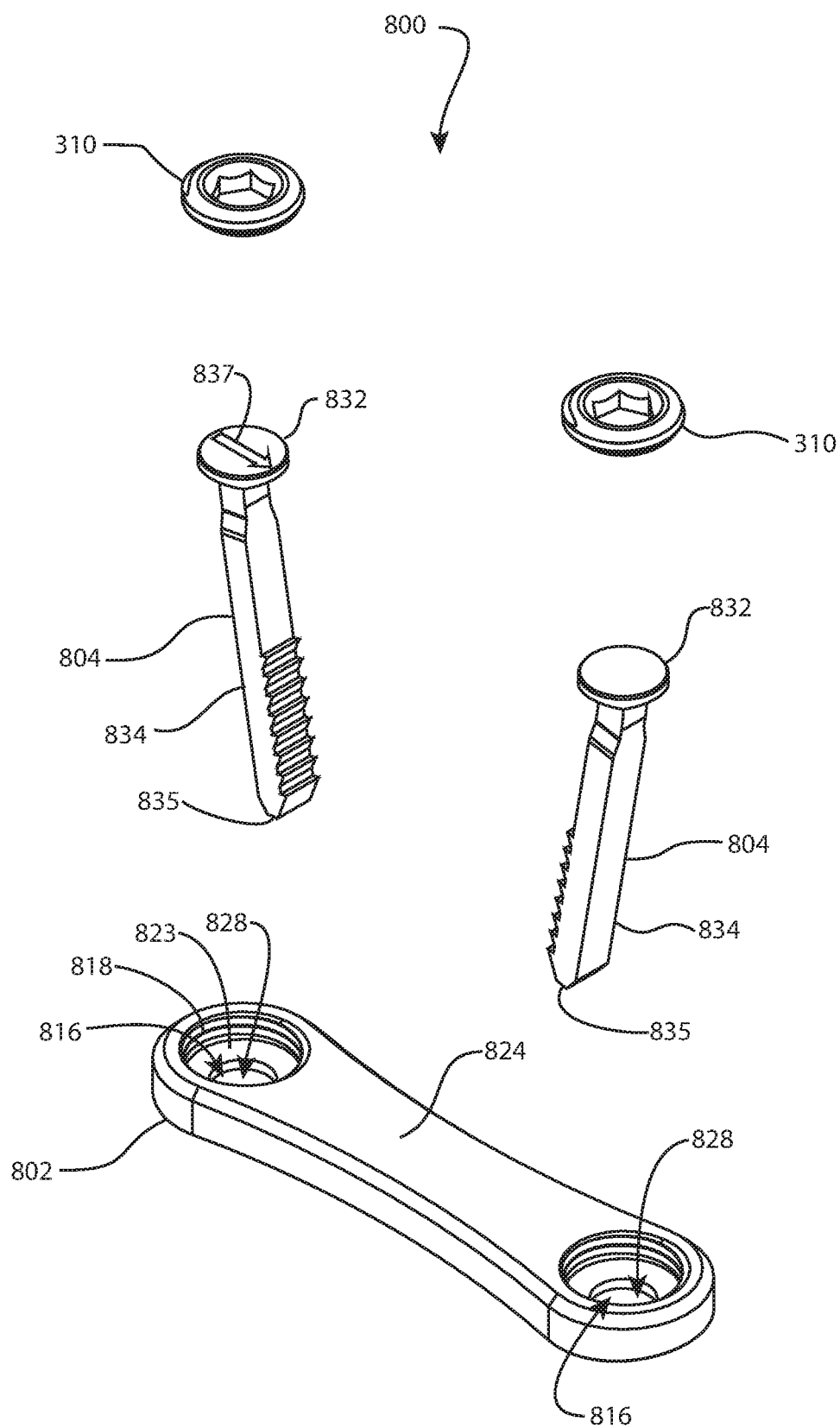
FIG. 8F is an exploded oblique view of the assembly of FIG. 8A.
Figure 8G:
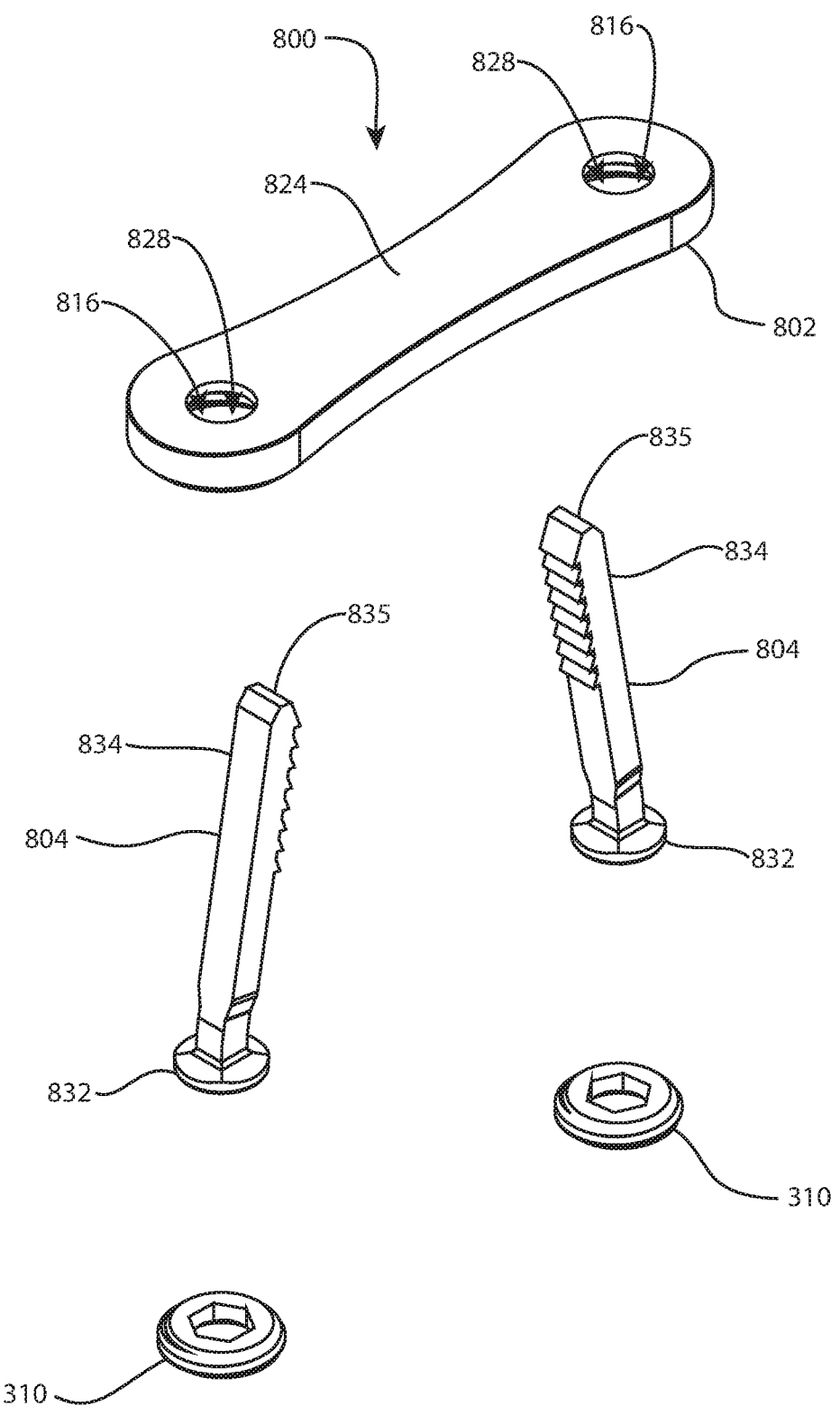
FIG. 8G is another exploded oblique view of the assembly of FIG. 8A from a different direction.

Two straight pegs 804 are shown facing each other in the assembly 800. In this example, the straight pegs 804 take the place of the previous dynamic elements, the staple 104 or the elbow pegs 604, 704. Each straight peg 804 includes a head 832 and a bone-contacting leg 834, which terminates in a free end 835. The head 832 may be rounded, as illustrated, or it may be any shape. The head 832 may include a mark 837, such as an arrowhead pointing toward the free end 835 of the leg 834 (FIG. 8F). The head 832 may form an obtuse angle, a right angle, or an acute angle with the leg 834 (FIG. 8E). Each straight peg 804 may be independently inserted into a bone hole and secured to the bone plate 802. The straight peg 804 may be secured to the bone plate 802 by the set screw 310 against the head 832. The shelf 823 prevents the head 832 from passing through the reverse side 814 of the bone plate 802. The straight peg 804 is free to rotate about its head 832 within the receiver hole 828, at least until secured by the set screw 310. Alternatively, the straight peg 804 may be rotationally constrained relative to the receiver hole 828 to a set of discrete rotational positions. The head 832 and/or the leg 834 of the straight peg 804 may be non-circular, and may engage a complementary non-circular portion of the receiver hole 828. A similar arrangement is illustrated in FIGS. 25A-H. Whether the straight pegs 804 are free to rotate or constrained to discrete rotational positions, the assembly 800 can deliver dynamic load in multiple directions relative to the bone plate 802 and/or other straight pegs 804. The mark 837 (arrowhead) may assist in orienting each leg 834 in the desired direction. FIGS. 8D and 8E illustrate that the straight peg 804 may develop spring force as the set screw 310 is fully seated, according to the same principles described for assembly 700 above. However, in FIG. 8E, the straight peg 804 is illustrated in its free state, having rotated counterclockwise due to the action of the set screw 310. If the leg 834 were constrained to the position shown in FIG. 8D, perpendicular to the bone plate 802, then the straight peg 804 would develop spring force as the set screw 310 is tightened.

While two straight pegs 804 are shown, a single straight peg 804 may be used opposite a locking screw 106. This arrangement is not shown. In this case, the bone plate would have an internally threaded hole 816 at one end (like hole 116 of bone plate 102) and at the other end, a receiver hole 828. The assembly would include a locking screw 106 in the internally threaded hole 816 and a straight peg 804 plus a set screw 310 in the receiver hole 828.

Referring to FIGS. 24A-24J, an assembly 1000 may include a stabilizing member and a dynamic element. In assembly 1000, the stabilizing member may be the bone plate 602 and the dynamic element may be a straight peg 1004.

Figure 24A:
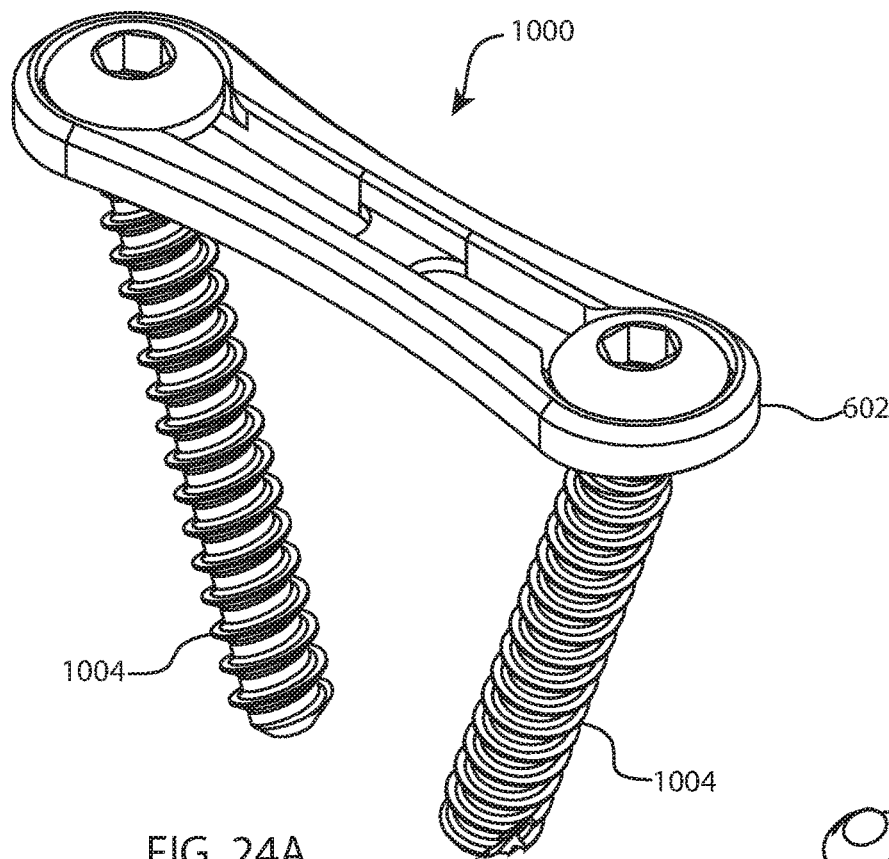
FIG. 24A is an oblique view of an assembly with a bone plate and straight threaded pegs.
Figure 24B:
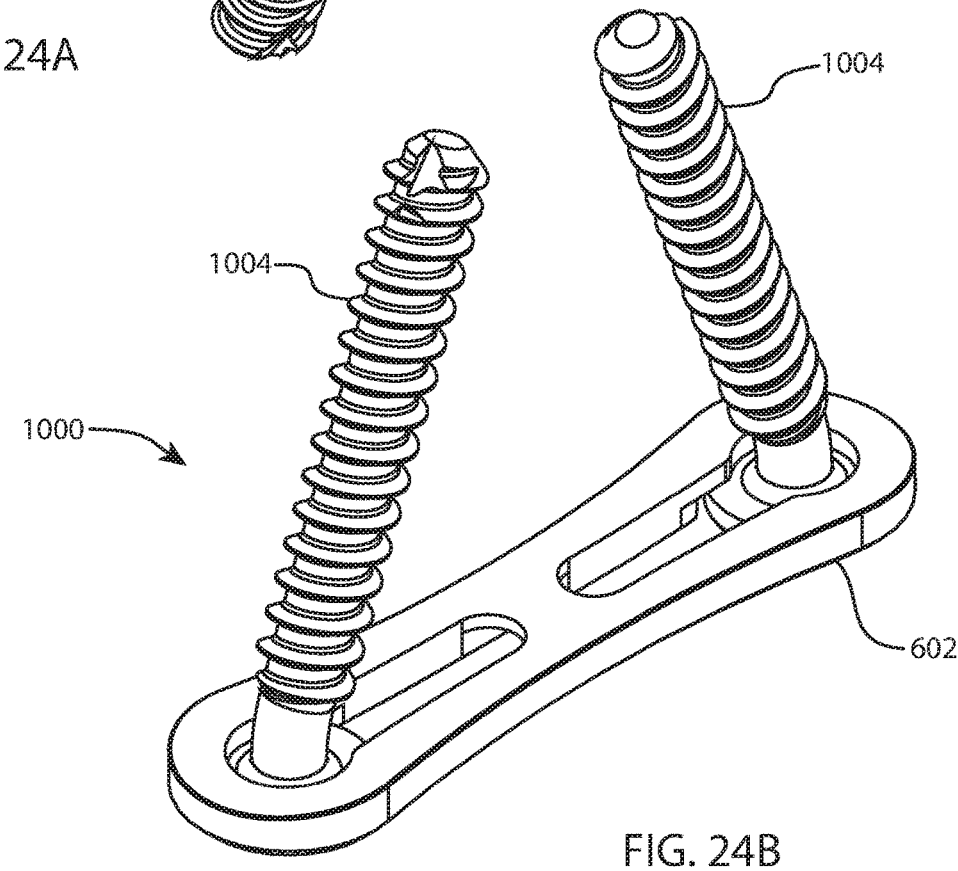
FIG. 24B is another oblique view of the assembly of FIG. 24A from a different direction.
Figure 24C:
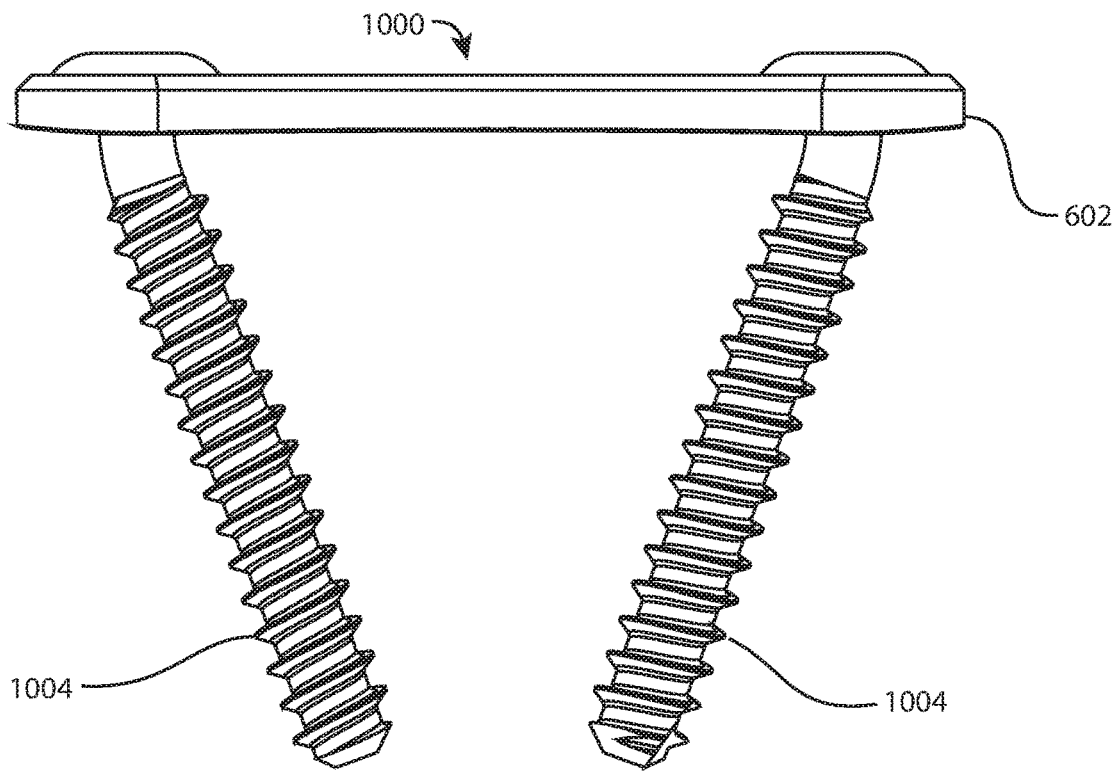
FIG. 24C is a side view of the assembly of FIG. 24A.
Figure 24D:
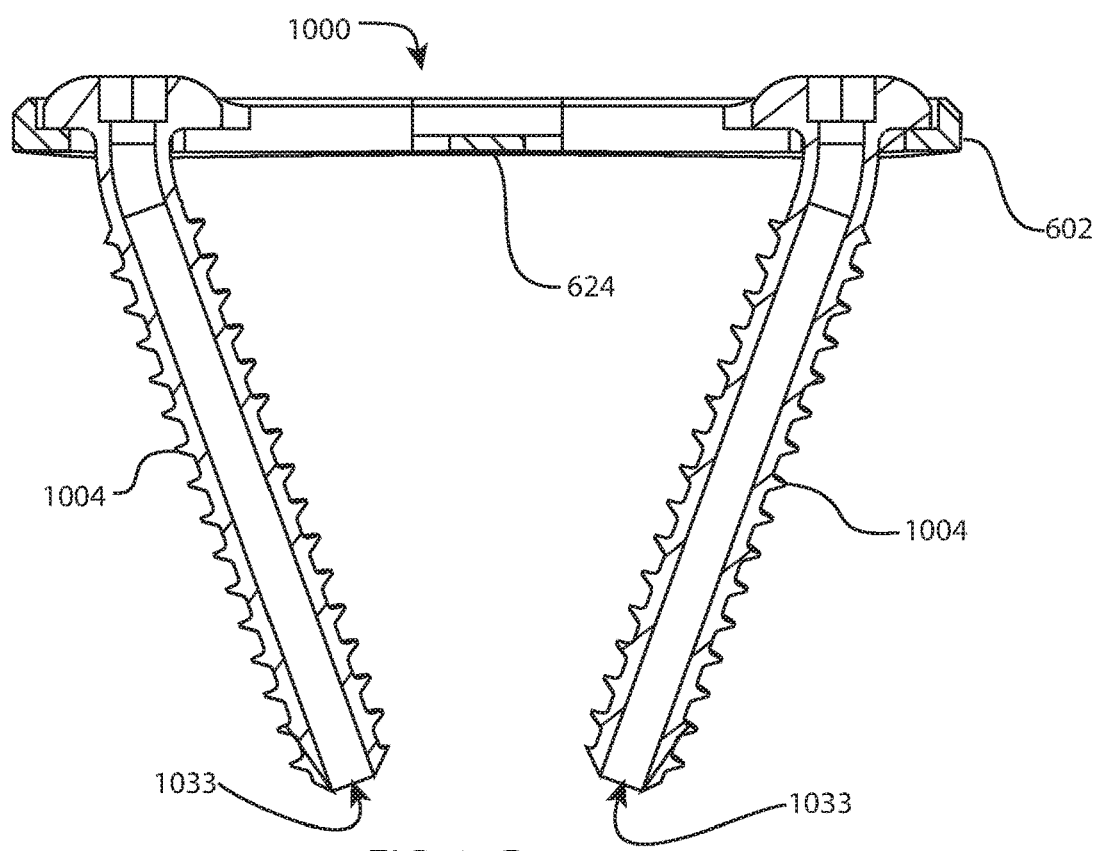
FIG. 24D is a longitudinal cross-section of a portion of the assembly of FIG. 24A along a mid-sagittal plane of the bone plate.
Figure 24E:
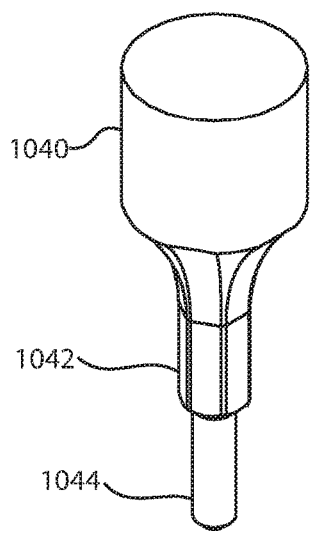
FIG. 24E is an oblique view of a portion of a straight peg inserter instrument.
Figure 24F:
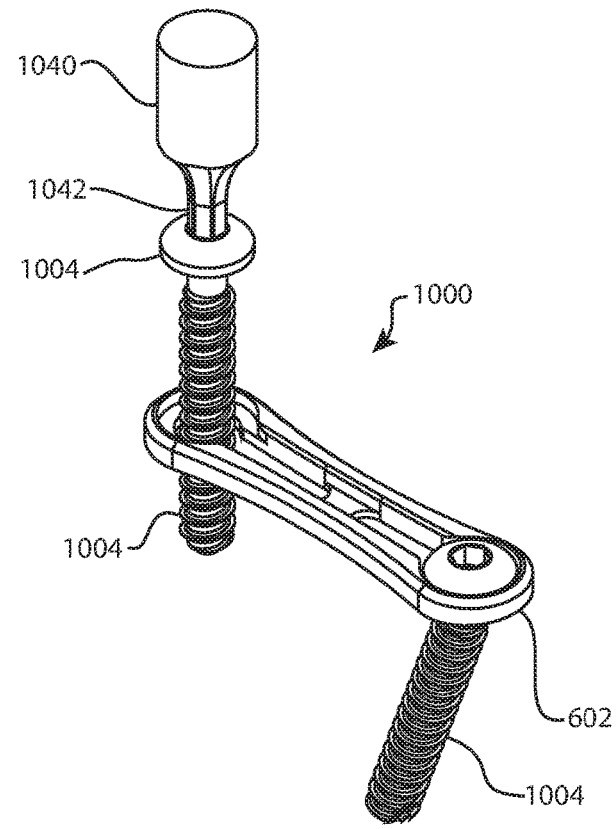
FIG. 24F is an oblique view of the assembly of FIG. 24A with the inserter instrument of FIG. 24E, with one straight peg partially inserted.
Figure 24G:
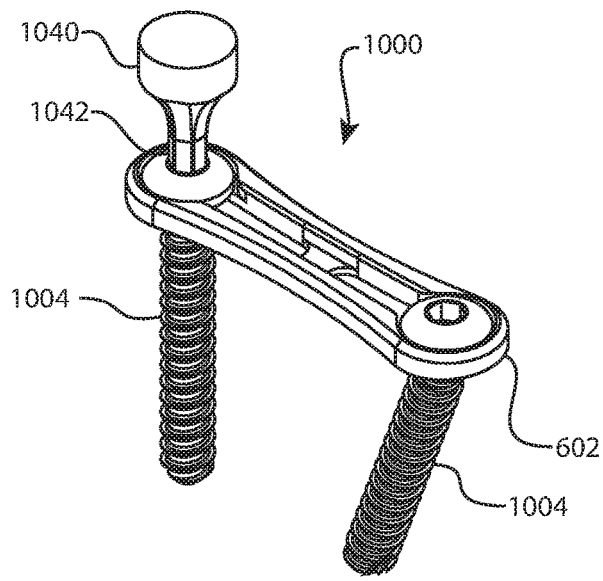
FIG. 24G is another oblique view of the assembly of FIG. 24A with the inserter instrument of FIG. 24E, with both straight pegs fully inserted.
Figure 24H:
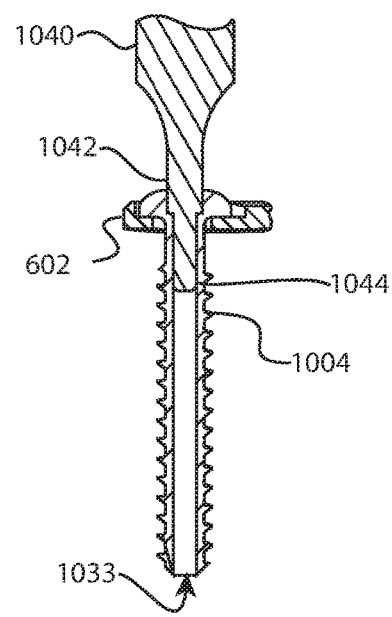
FIG. 24H is a cross sectional view of a portion of the components of FIG. 24G.
Figure 24I:
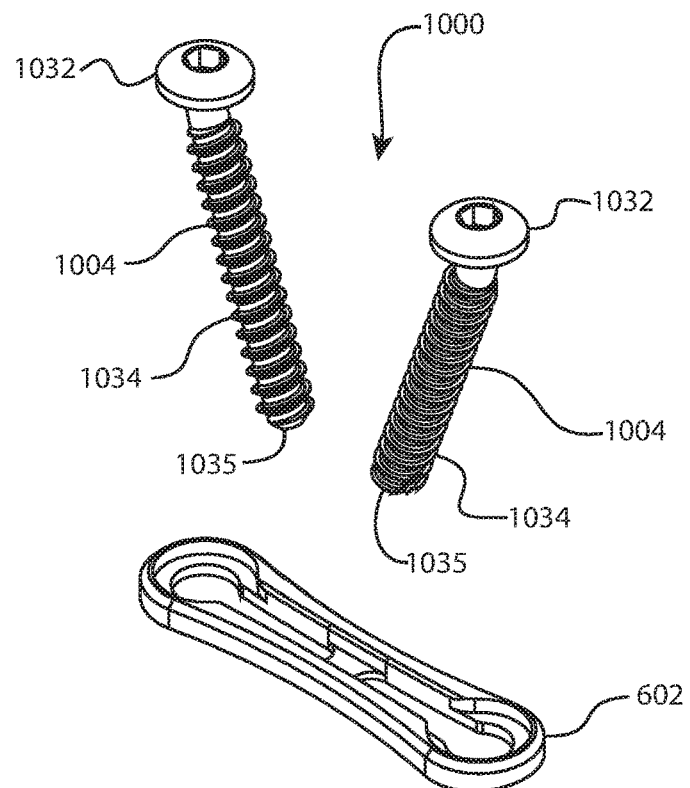
FIG. 24I is an exploded oblique view of the assembly of FIG. 24A.
Figure 24J:
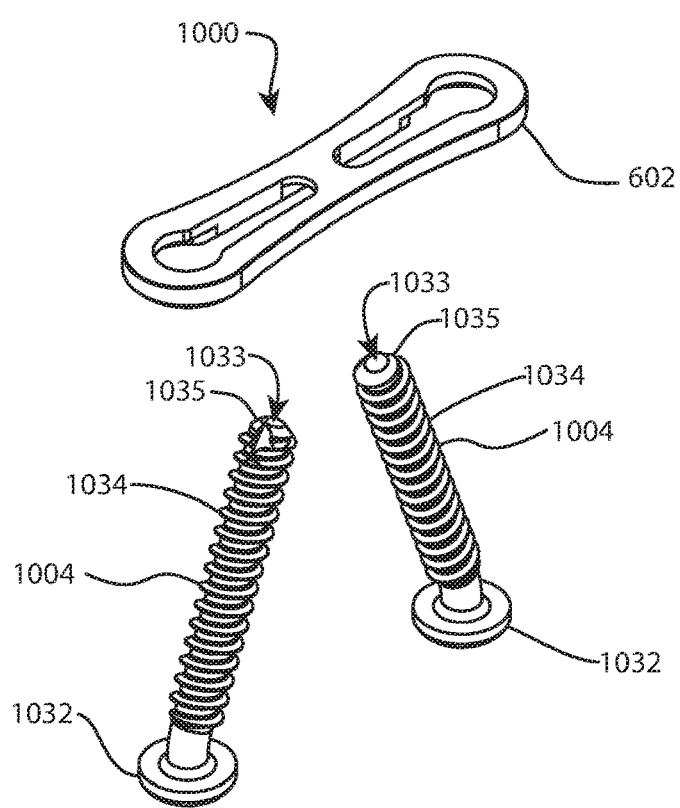
FIG. 24J is another exploded oblique view of the assembly of FIG. 24A from a different direction.

Two straight pegs 1004 are shown facing each other in the assembly 1000. In this example, the straight pegs 1004 take the place of the previous dynamic elements, the staple 104 or the elbow pegs 604, 704 or the straight peg 804. Each straight peg 1004 includes a rounded head 1032 and a bone-contacting leg 1034, which terminates in a free end 1035. The head 1032 may form an obtuse angle, a right angle, or an acute angle with the leg 1034 (FIG. 24O). The head 1032 may include a mark pointing toward the free end 1035 of the leg 1034, similar to mark 837 of straight peg 804. The leg 1034 may include external threads as shown, or the leg 1034 may be smooth. Each straight peg 1004 may be independently inserted into a bone hole and secured to the bone plate 602. The straight peg 1004 may be secured to the bone plate 602 by threading the leg 1034 into bone, or with a set screw 310 as explained previously. The shelf 623 prevents the head 1032 from passing through the reverse side 614 of the bone plate 602. The straight peg 1004 may develop spring force, according to similar principles to those described above. FIG. 24E illustrates an inserter tool 1040 for temporarily straightening the angle between the head 1032 and the leg 1034, and for threading the leg 1034 into a bone hole. The inserter tool 1040 includes a torque drive feature 1042 (a hex) with a distal shaft 1044 that extends within a cannulation 1033 in the straight peg 1004.

While two straight pegs 1004 are shown, a single straight peg 1004 may be used opposite a locking screw 106. This arrangement is not shown. In this case, the bone plate 602 would have an internally threaded hole 616 at one end (like hole 116 of bone plate 102) and at the other end, a receiver hole 628. The assembly would include a locking screw 106 in the internally threaded hole 616 and a straight peg 1004 in the receiver hole 628.

Referring to FIGS. 25A-25H, an assembly 1100 may include a stabilizing member, a dynamic element, and one or more fasteners. In assembly 1100, the stabilizing member may be a bone plate 1102, the dynamic element may be a wire peg 1104, and the fastener may include a set screw 310.

The bone plate 1102 has an obverse side 1112 and a reverse side 1114. The bone plate 1102 includes several holes 1116, each of which may include an internally threaded portion 1118. The internally threaded portion 1118 may be adjacent to the obverse side 1112. Each hole 1116 may include an interior shelf 1123. The shelf 1123 may be adjacent to the reverse side 1114. A web 1124 extends between two of the holes 1116. The web 1124 may be adjacent to the reverse side 1114. The web 1124 separates the two holes 1116, and may be present even if the holes 1116 are elongated towards each other. The two holes 1116 are referred to as receiver holes 1128, since these features receive the wire pegs 1104. Each receiver hole 1128 includes a noncircular through hole 1129. The illustrated holes 1129 are rectangular, and may be square.

Figure 25A:
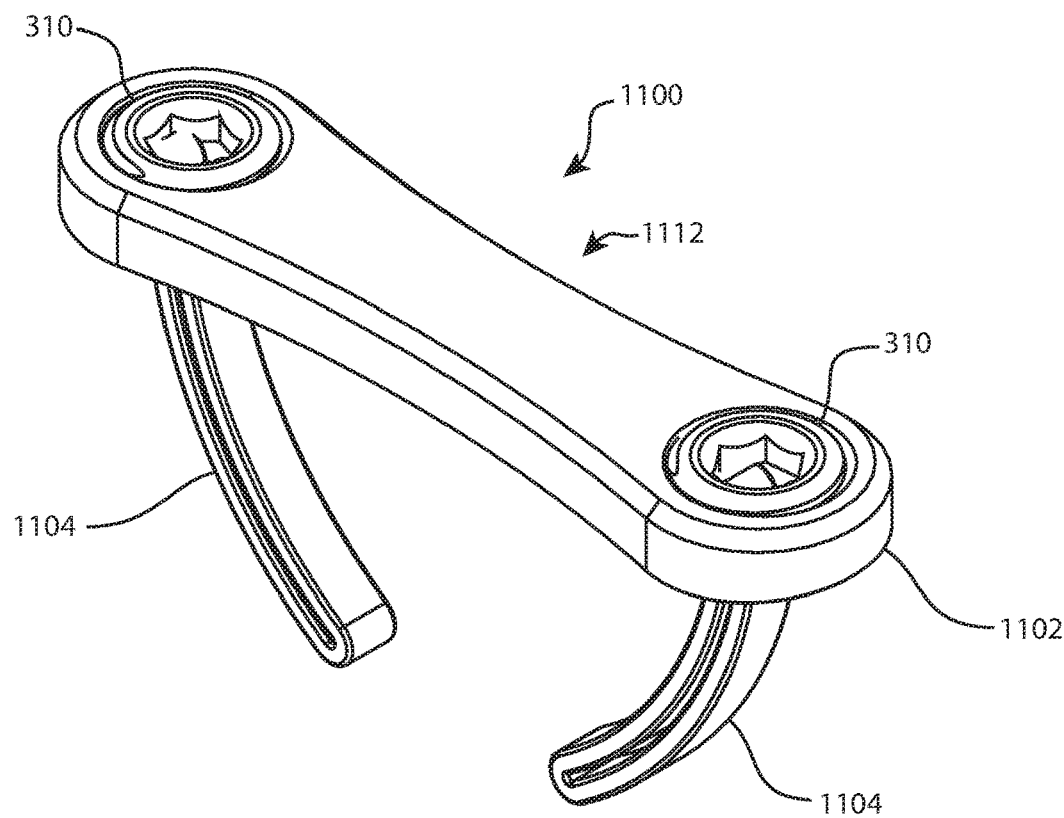
FIG. 25A is an oblique view of an assembly with a bone plate, wire pegs, and set screws.
Figure 25B:
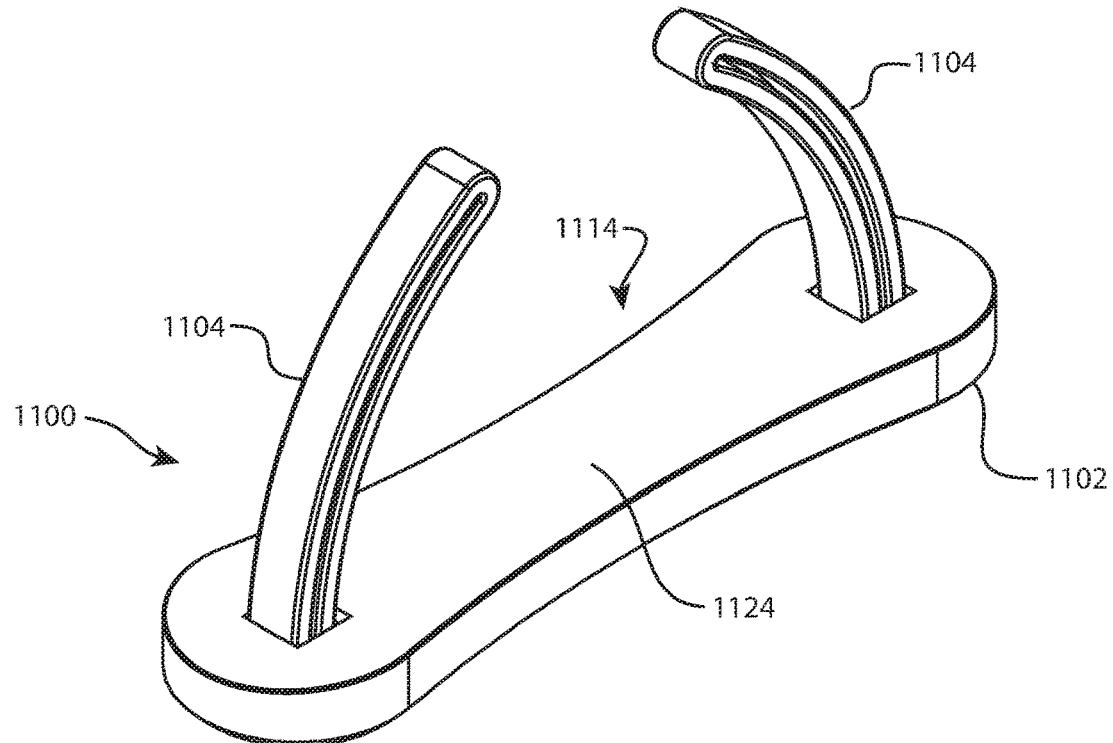
FIG. 25B is another oblique view of the assembly of FIG. 25A from a different direction.
Figure 25G:
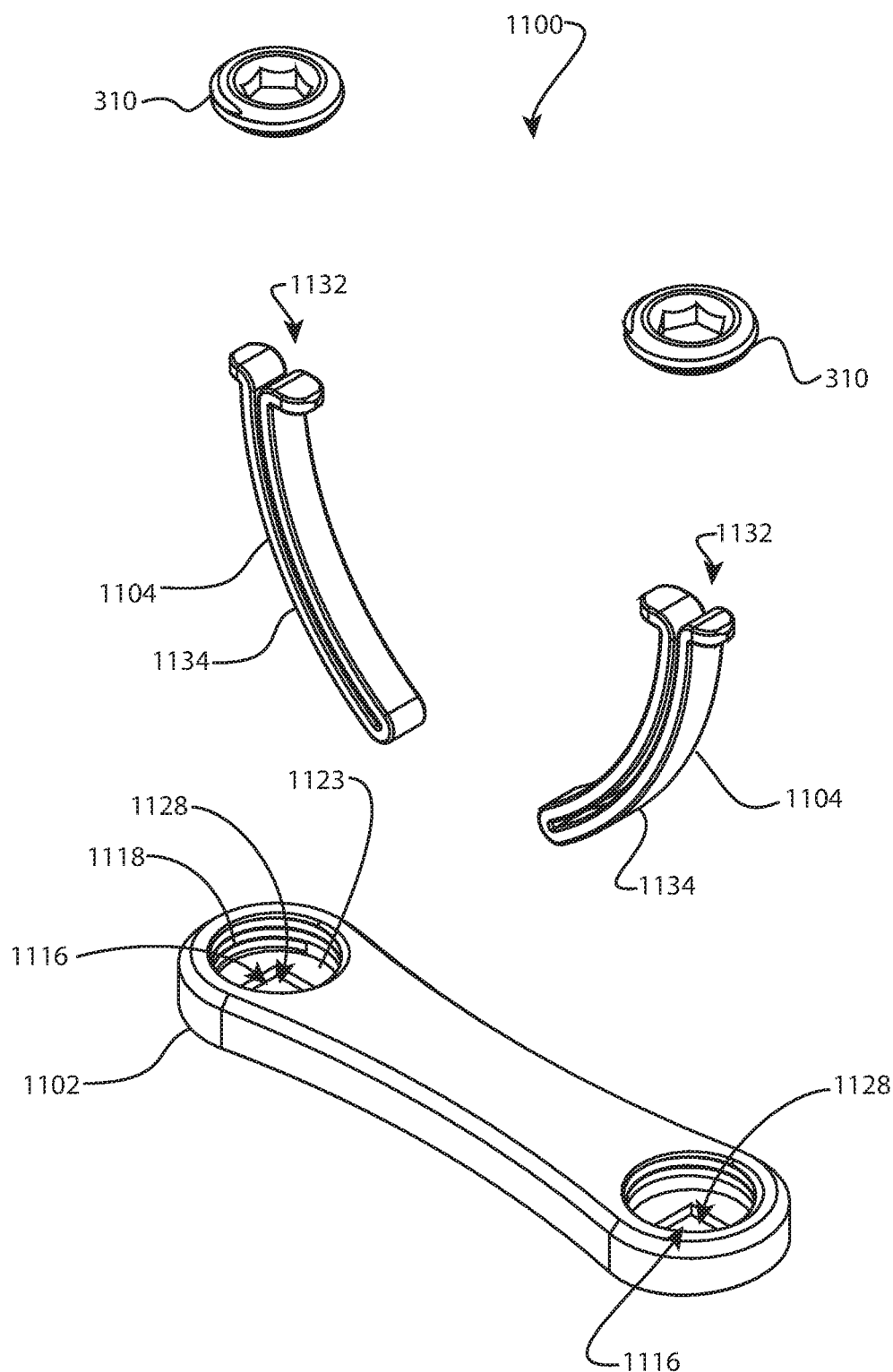
FIG. 25G is an exploded oblique view of the assembly of FIG. 25A.
Figure 25H:
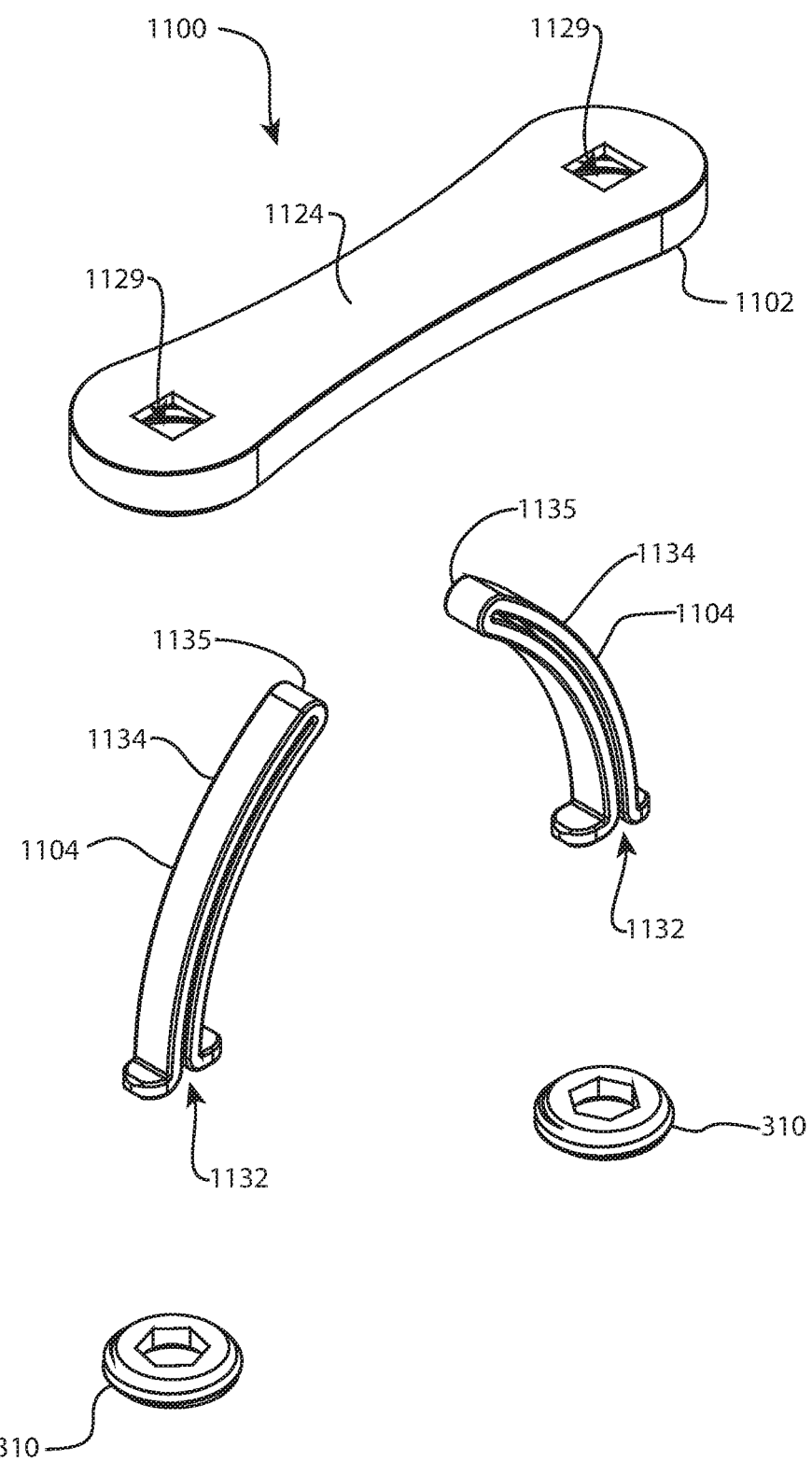
FIG. 25H is another exploded oblique view of the assembly of FIG. 25A from a different direction.

Two wire pegs 1104 are shown facing each other in the assembly 1100. In this example, the wire pegs 1104 take the place of the previous dynamic elements, the staple 114, the elbow pegs 604, 704, the straight pegs 804, 1004. Each wire peg 1104 is formed from a sharply bent, or folded, piece of wire having a rectangular cross section. Each wire peg 1104 includes a head 1132 and a bone-contacting leg 1134, which terminates in a free end 1135 where the wire is sharply bent or folded. The head 1132 in this example is formed by outwardly bent ends, or terminal portions, of the wire. The head 1132 may form an obtuse angle, a right angle, or an acute angle with the leg 1134. In FIG. 25E-F, the outwardly bent wire ends of the head 1132 form right angles with the leg 1134 when the wire peg 1104 is in the free state. The outwardly bent wire ends of the head 1132 are uneven when the wire peg 1104 is in the free state. Each wire peg 1104 may be independently inserted into a bone hole and secured to the bone plate 1102. The wire peg 1104 may be secured to the bone plate 1102 with a set screw 310. The shelf 1123 prevents the head 1132 from passing through the reverse side 1114 of the bone plate 1102. The wire peg 1104 may develop spring force and may bow sideways as the set screw 310 is tightened, due to the uneven height of the outwardly bent wire ends of the head 1132. The stressed or bowed state of the wire peg 1104 is illustrated in FIGS. 25A-25D, 25G, and 25H.

While two wire pegs 1104 are shown, a single wire peg 1104 may be used opposite a locking screw 116. This arrangement is not shown. In this case, the bone plate would have an internally threaded hole 1116 at one end (like hole 116 of bone plate 102) and at the other end, a receiver hole 1128. The assembly would include a locking screw 116 in the internally threaded hole 1116 and a wire peg 1104 with a set screw 310 in the receiver hole 1128.

Referring to FIGS. 26A-26H, an assembly 1200 may include a stabilizing member, a dynamic element, and one or more fasteners. In assembly 1200, the stabilizing member may be a bone plate 1202, the dynamic element may be a wire peg 1204, and the fastener may include a set screw 310.

The bone plate 1202 has an obverse side 1212 and a reverse side 1214. The bone plate 1202 includes several holes 1216, each of which may include an internally threaded portion 1218. The internally threaded portion 1218 may be adjacent to the obverse side 1212. Each hole 1216 may include an interior shelf 1223. The shelf 1223 may be adjacent to the reverse side 1214. The shelf 1223 may include a medial alcove 1221. A web 1224 extends between two of the holes 1216. The web 1224 may be adjacent to the reverse side 1214. The web 1224 separates the two holes 1216, and may be present even if the holes 1216 are elongated towards each other. The two involved holes 1216 are referred to as receiver holes 1228, since these features receive the wire pegs 1204. Each receiver hole 1228 includes a noncircular through hole 1229. The illustrated holes 1229 are elongated, and may be oval, round, or another shape such as rectangular or square.

Figure 26A:
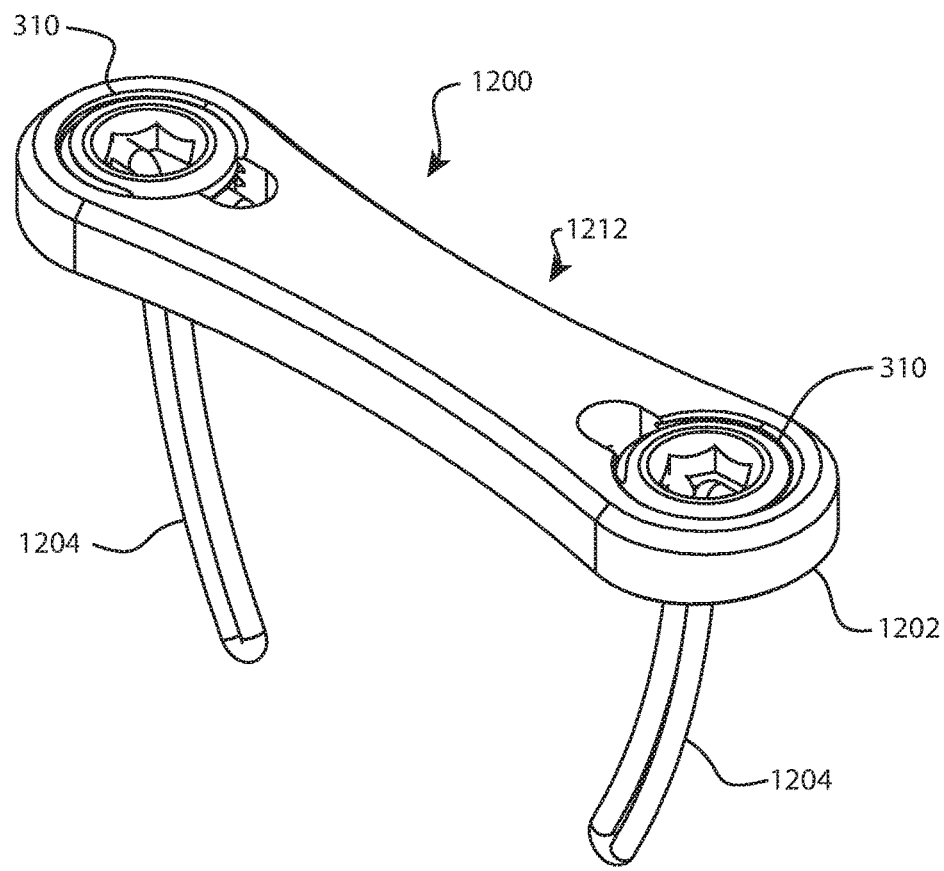
FIG. 26A is an oblique view of an assembly with a bone plate, wire pegs, and set screws.
Figure 26B:
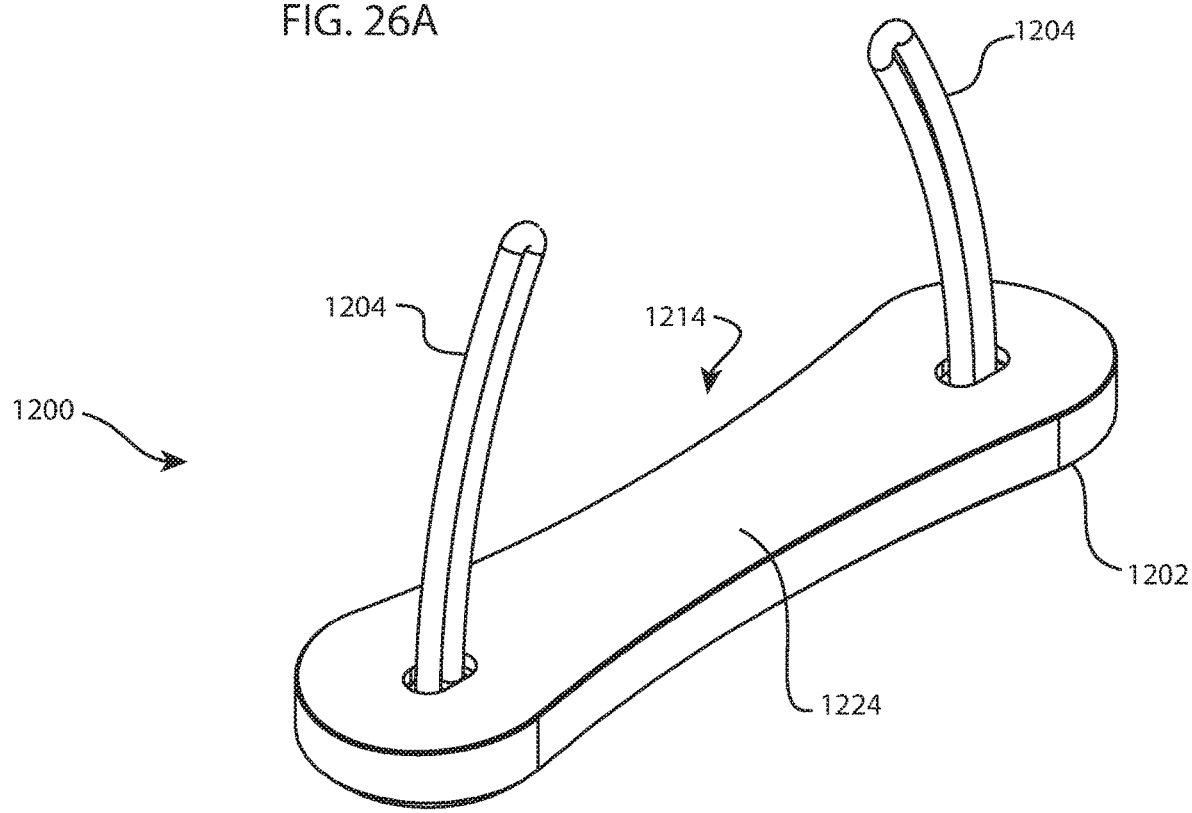
FIG. 26B is another oblique view of the assembly of FIG. 26A from a different direction.
Figure 26C:
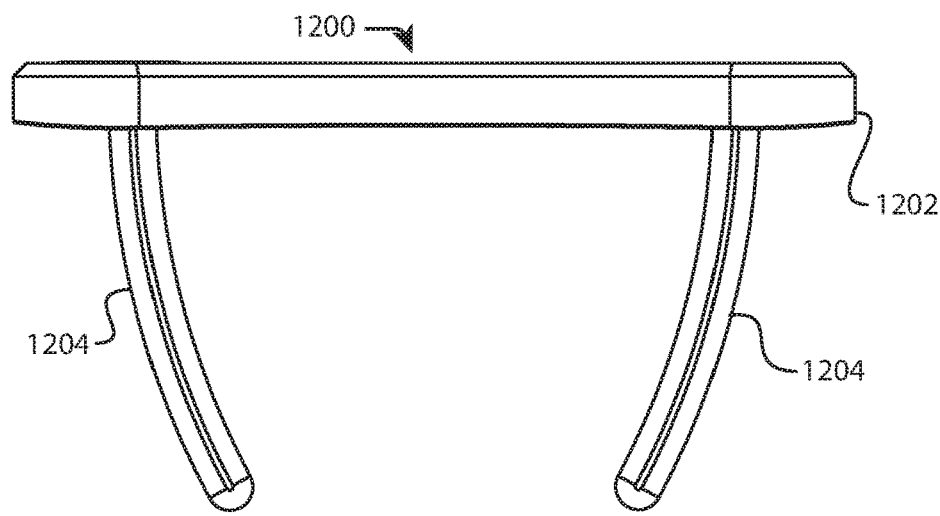
FIG. 26C is a side view of the assembly of FIG. 26A.
Figure 26D:
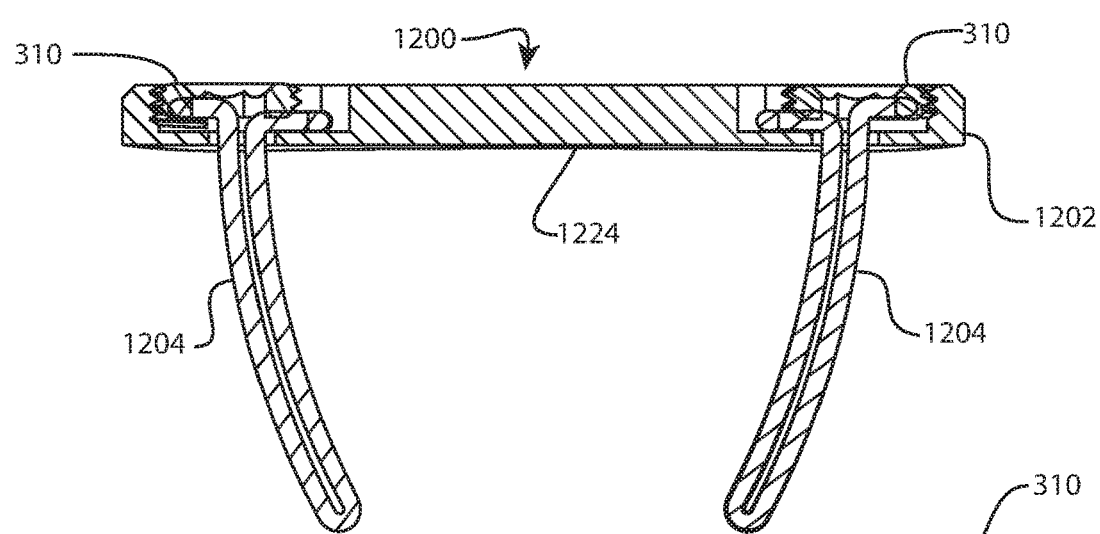
FIG. 26D is a longitudinal cross-section of a portion of the assembly of FIG. 26A along a mid-sagittal plane of the bone plate.
Figure 26E:
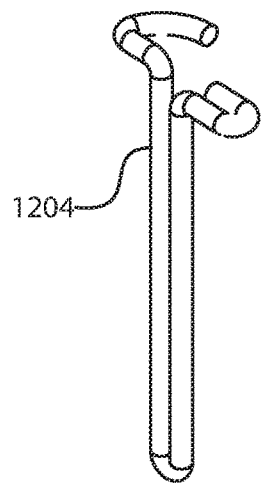
FIG. 26E is an oblique view of the wire peg of FIG. 26A in a free state.
Figure 26F:
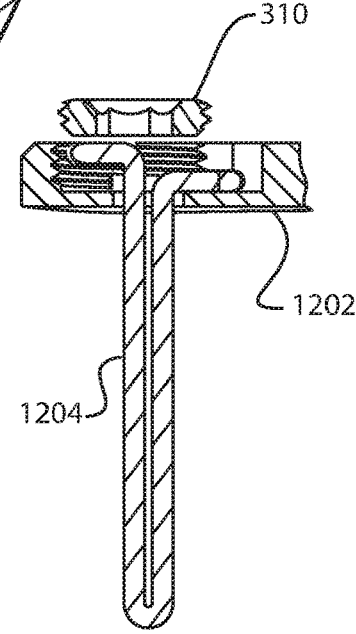
FIG. 26F is a cross sectional view of a portion of the assembly of FIG. 26A, with a wire peg in a free state.
Figure 26G:
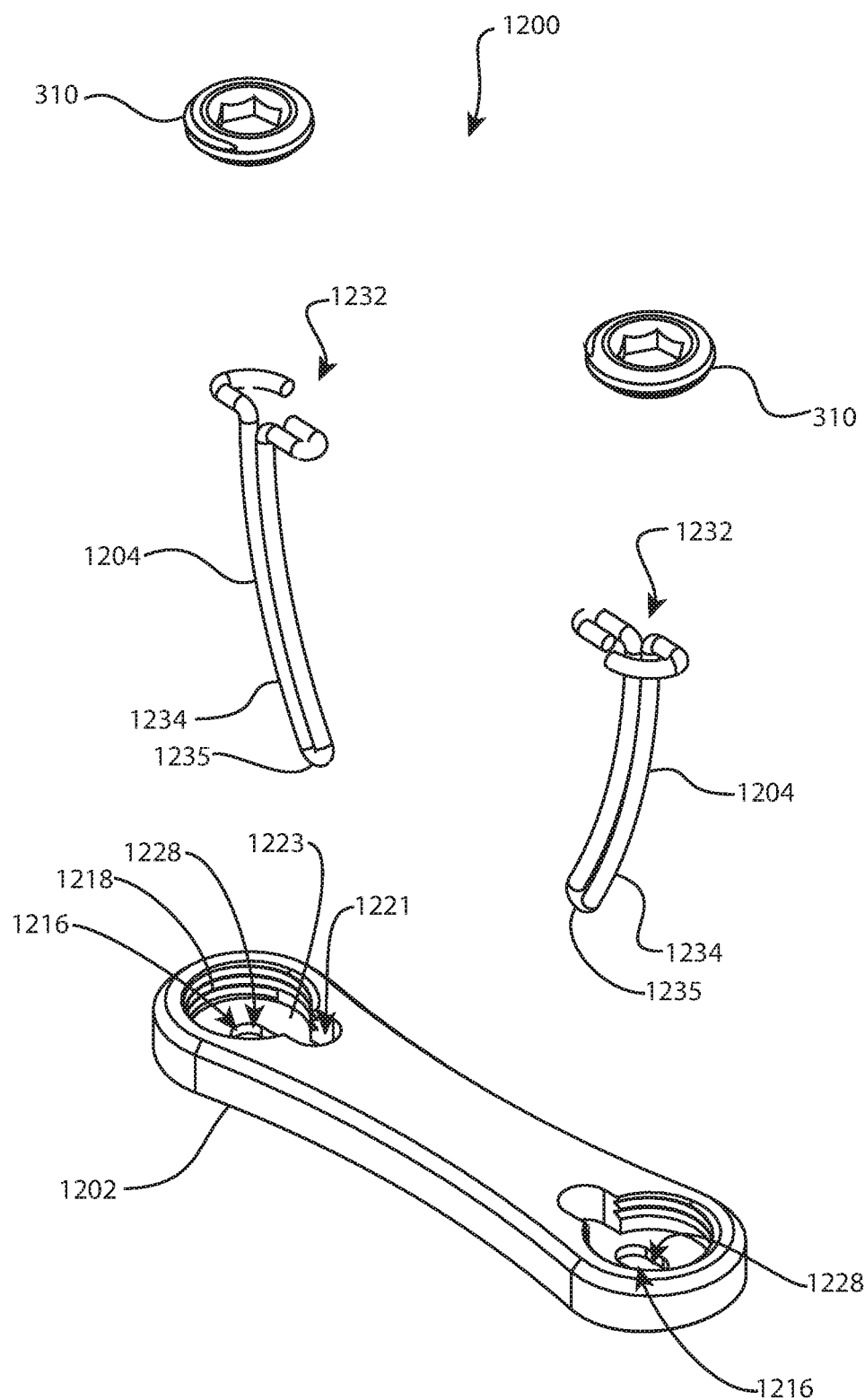
FIG. 26G is an exploded oblique view of the assembly of FIG. 26A.
Figure 26H:
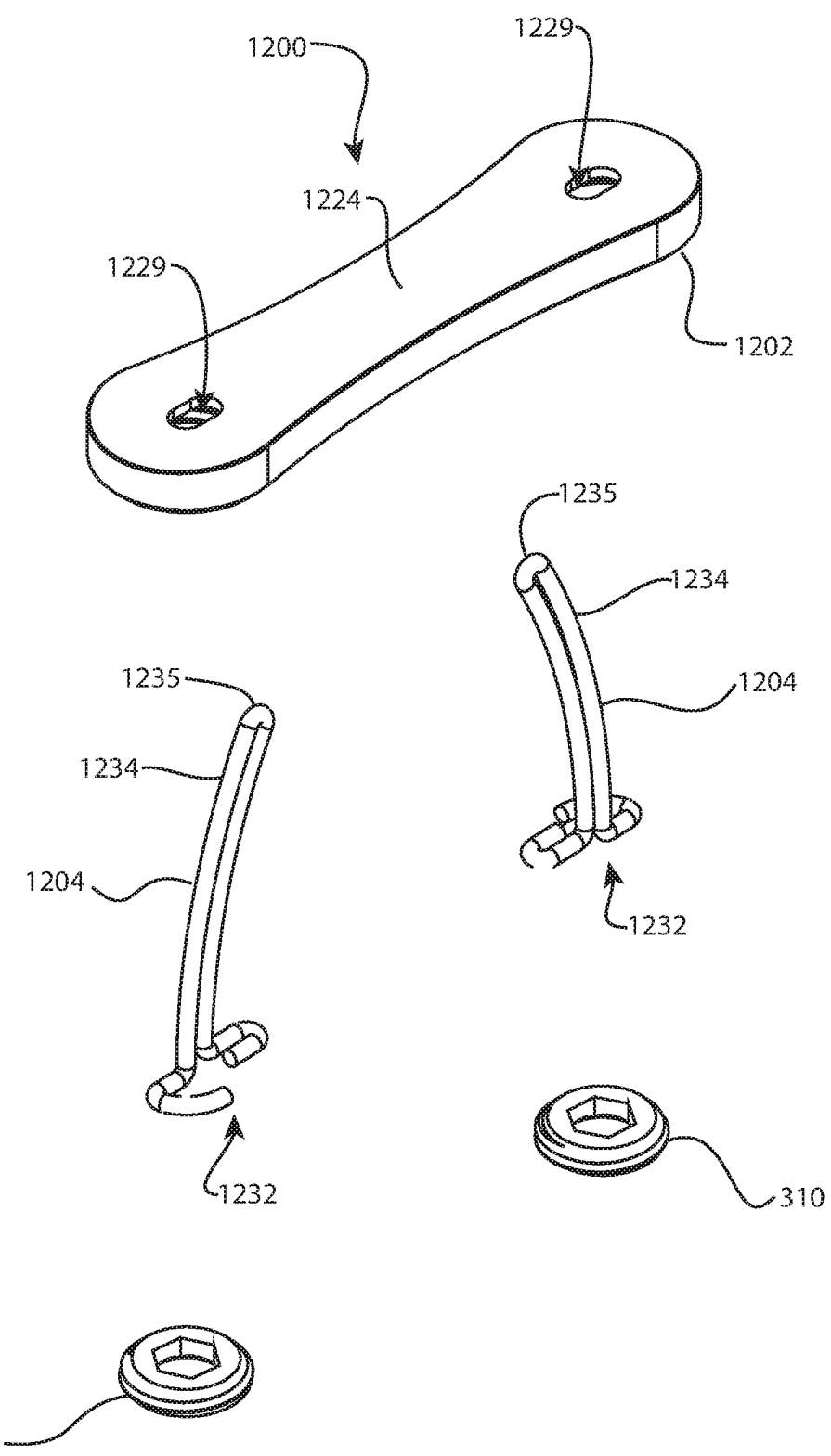
FIG. 26H is another exploded oblique view of the assembly of FIG. 26A from a different direction.

Two wire pegs 1204 are shown facing each other in the assembly 1200. In this example, the wire pegs 1204 take the place of the previous dynamic elements, the staple 104, the elbow pegs 604, 704, the straight pegs 804, 1004, or the wire peg 1104. Each wire peg 1204 is formed from a sharply bent, or folded, piece of wire having a round cross section. Each wire peg 1204 includes a head 1232 and a bone-contacting leg 1234, which terminates in a free end 1235 where the wire is sharply bent or folded. The head 1232 in this example is formed by outwardly bent ends, or terminal portions, of the wire. The head 1232 may form an obtuse angle, a right angle, or an acute angle with the leg 1234. In FIG. 26E-F, the outwardly bent wire ends of the head 1232 form right angles with the leg 1234 when the wire peg is in the free state. The outwardly bent wire ends of the head 1232 are uneven when the wire peg is in the free state. Each wire peg 1204 may be independently inserted into a bone hole and secured to the bone plate 1202. The wire peg 1204 may be secured to the bone plate 1202 with a set screw 310. The wire peg 1204 may develop spring force and may bow sideways as the set screw is tightened, due to the uneven height of the outwardly bent wire ends of the head 1232. The stressed or bowed state of the wire peg 1204 is illustrated in FIGS. 26A-26D, 26G, and 26H.

While two wire pegs 1204 are shown, a single wire peg 1204 may be used opposite a locking screw 126. This arrangement is not shown. In this case, the bone plate would have an internally threaded hole 1216 at one end (like hole 116 of bone plate 102) and at the other end, a receiver hole 1228. The assembly would include a locking screw 126 in the internally threaded hole 1216 and a wire peg 1204 with a set screw 310 in the receiver hole 1228.

Figure 27A:
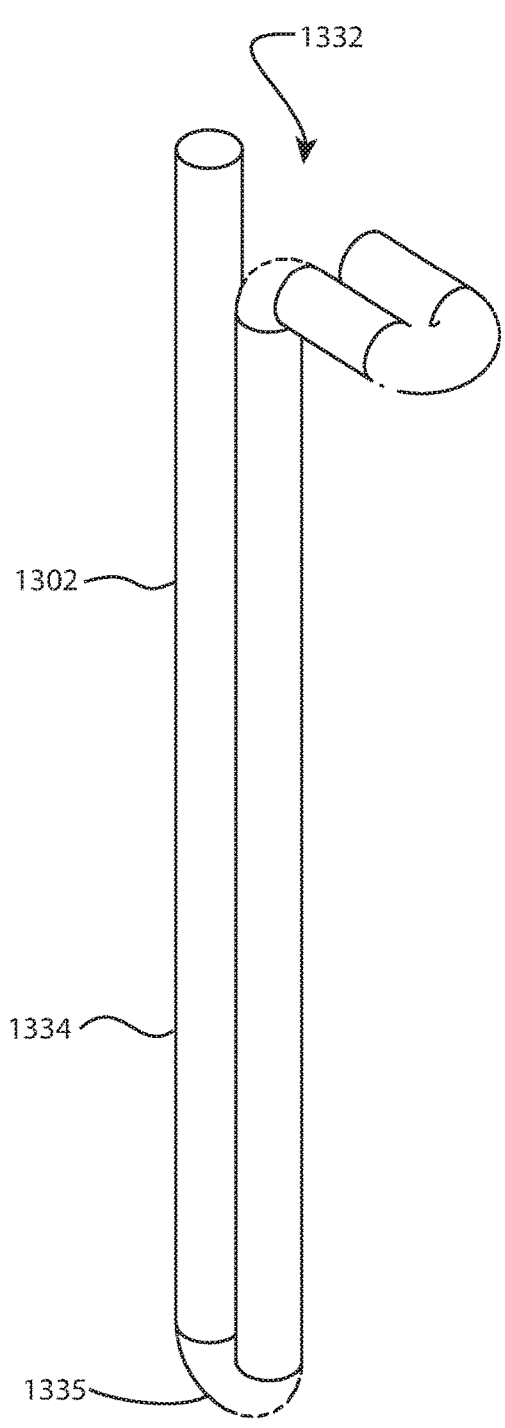
FIG. 27A is an oblique view of a wire peg in a free state.
Figure 27B:
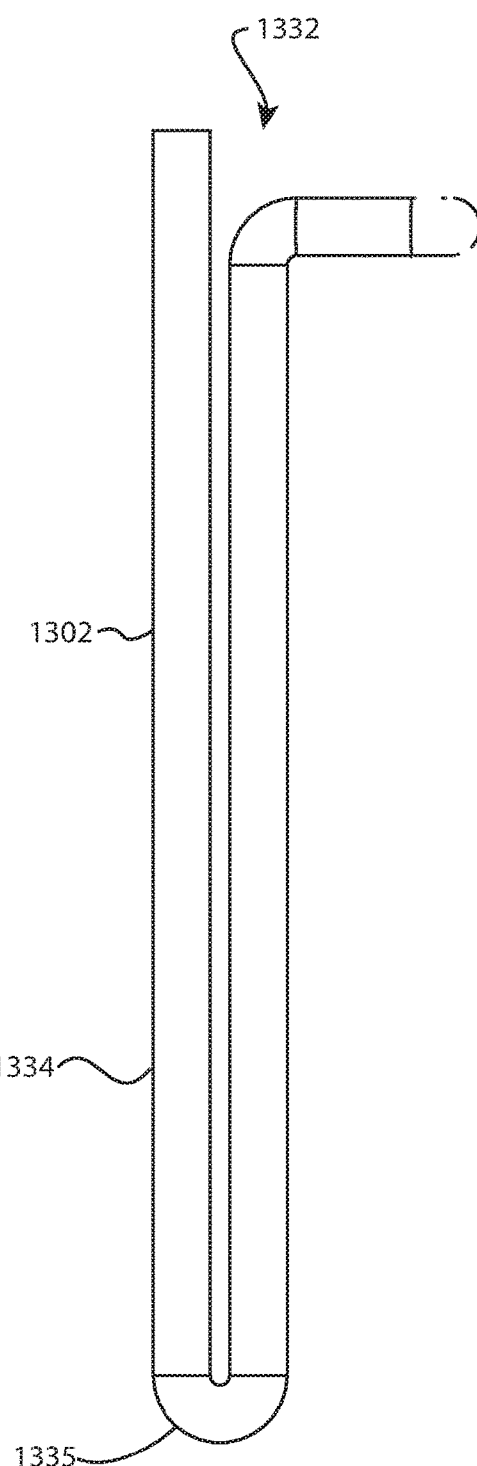
FIG. 27B is a side view of the wire peg of FIG. 27A.
Figure 28A:
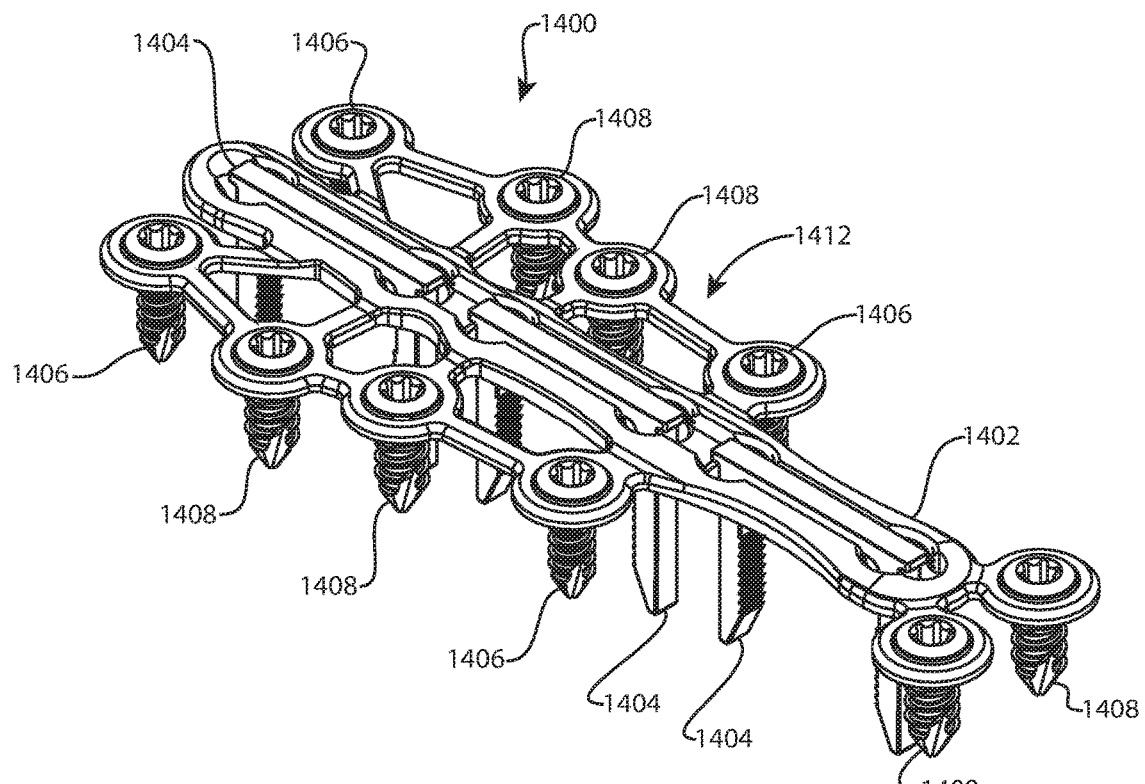
FIG. 28A is an oblique view of an assembly with a bone plate, staples, and screws.
Figure 28B:
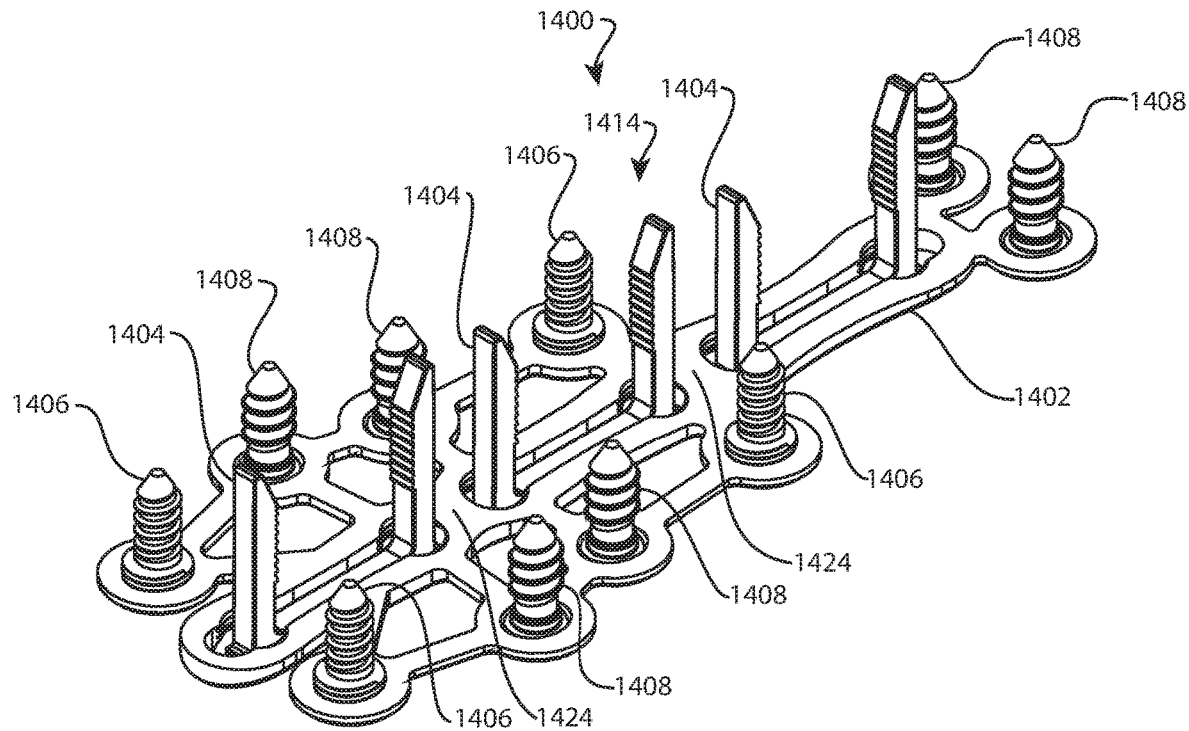
FIG. 28B is another oblique view of the assembly of FIG. 28A from a different direction.
Figure 28C:
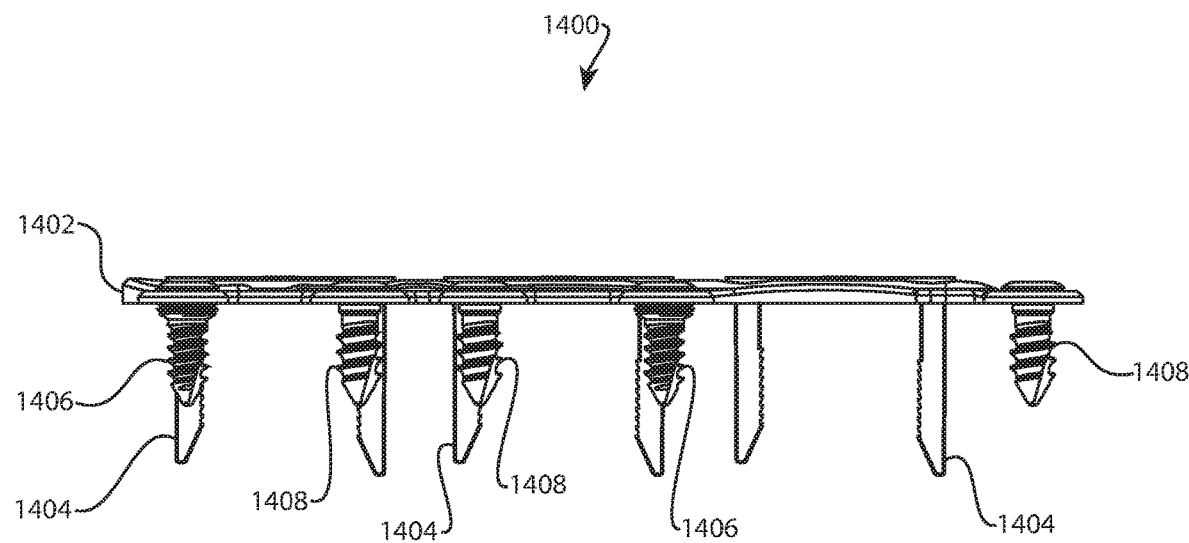
FIG. 28C is a side view of the assembly of FIG. 28A.
Figure 28D:
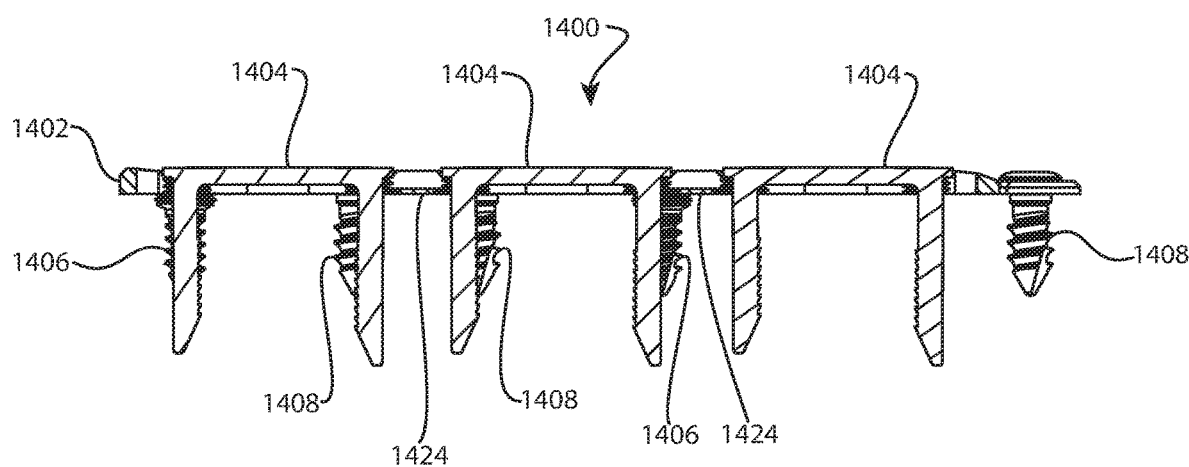
FIG. 28D is a longitudinal cross-section of the assembly of FIG. 28A along a mid-sagittal plane of the bone plate.
Figure 28E:
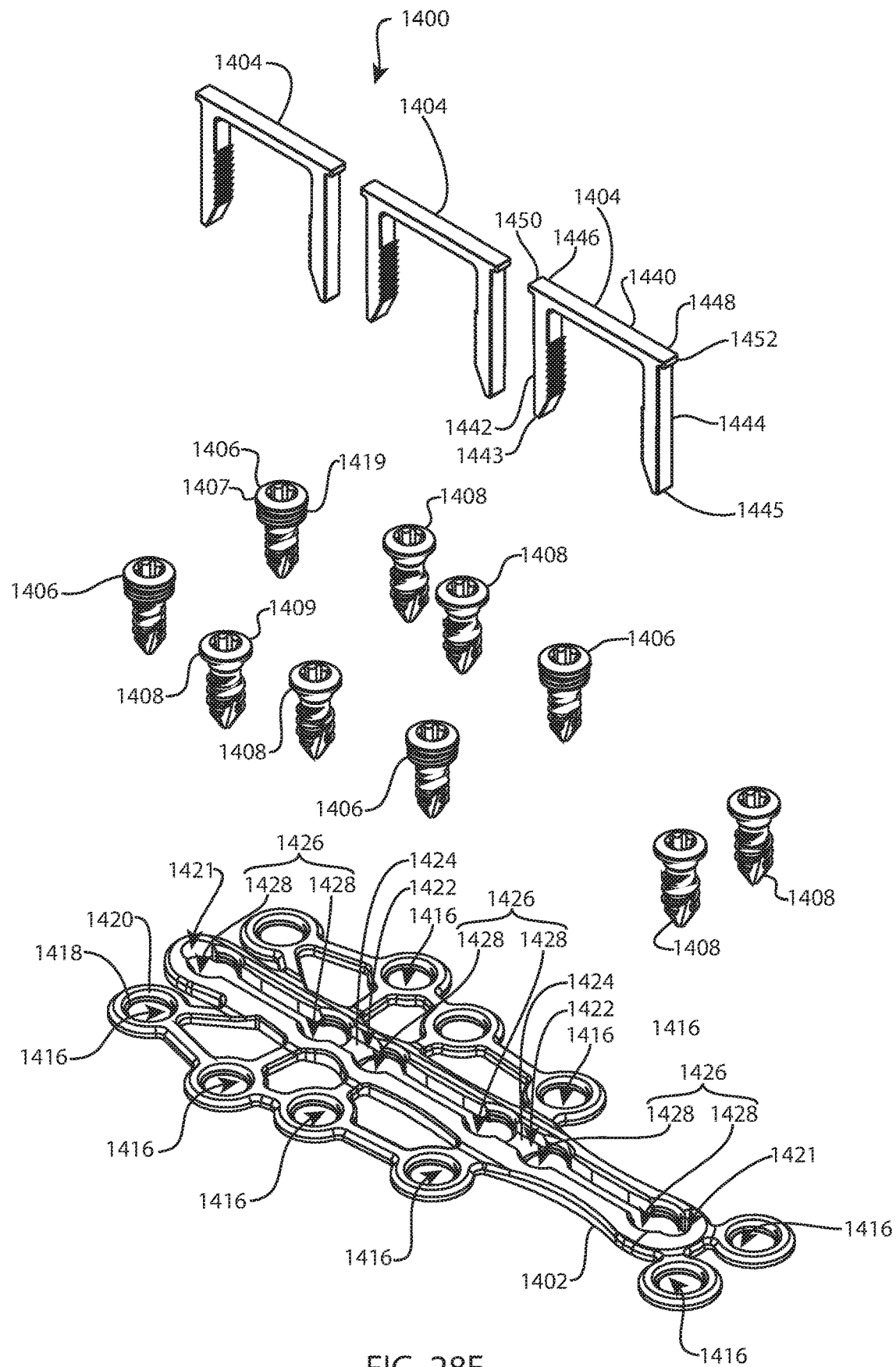
FIG. 28E is an exploded oblique view of the assembly of FIG. 28A.
Figure 28F:
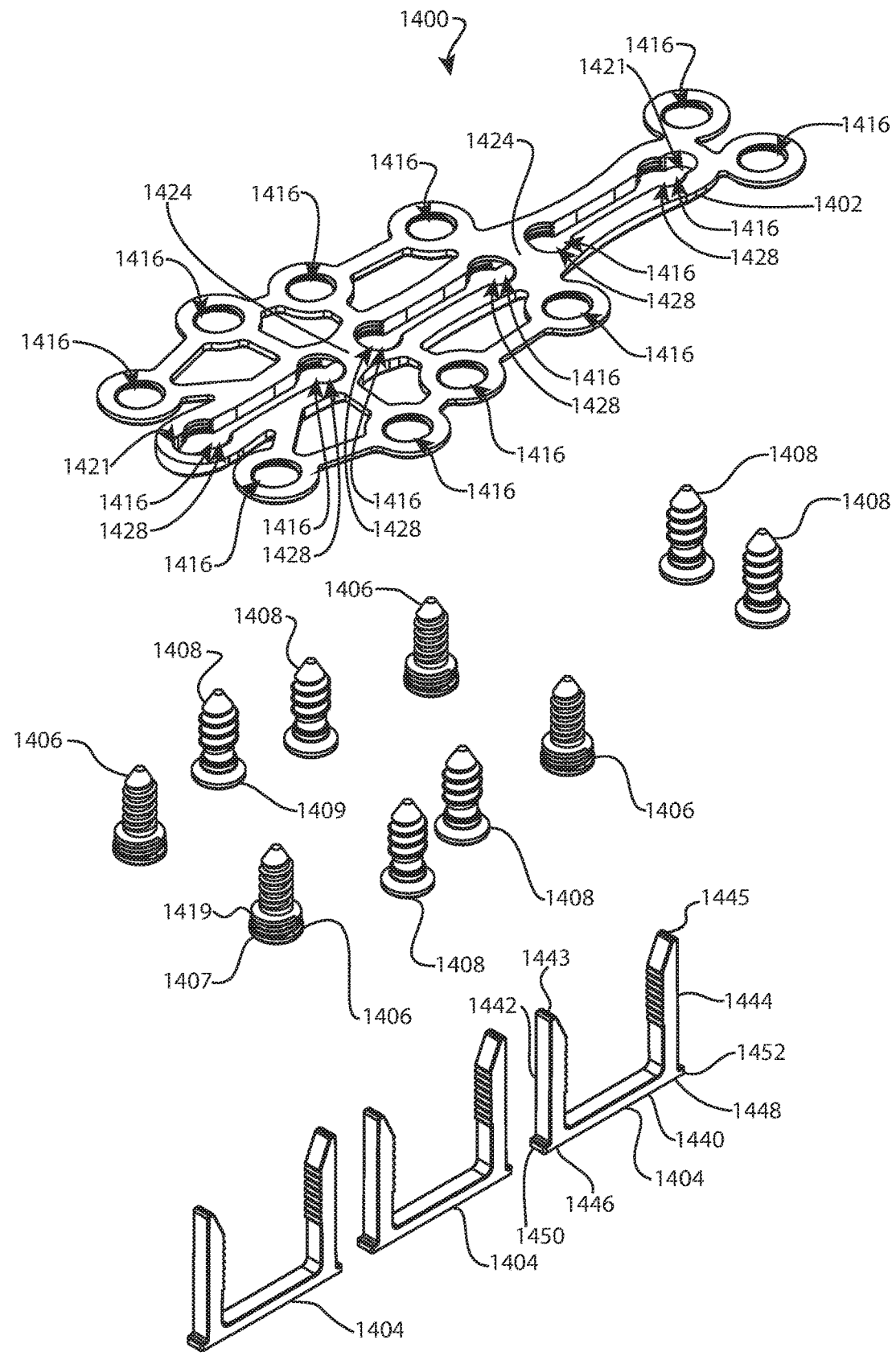
FIG. 28F is another exploded oblique view of the assembly of FIG. 28A from a different direction.

Referring to FIGS. 27A and 27B, an alternative wire peg 1302 is formed from a sharply bent, or folded, piece of wire having a round cross section. Each wire peg 1304 includes a head 1332 and a bone-contacting leg 1334, which terminates in a free end 1335 where the wire is sharply bent or folded. The head 1332 in this example is formed by an outwardly bent end, or terminal portion, of the wire and a straight end of the wire. The head 1332 may form an obtuse angle, a right angle, or an acute angle with the leg 1334. In FIG. 26E-F, the outwardly bent wire end of the head 1332 forms a right angle with the leg 1334 when the wire peg is in the free state. The outwardly bent wire end of the head 1332 is uneven with the straight end of the head 1332 when the wire peg is in the free state. This wire peg 1302 may be used interchangeably with the wire pegs 1102 and 1202.

Referring to FIGS. 28A-28F, an assembly 1400 may include a stabilizing member, a dynamic element, and one or more fasteners. In assembly 1400, the stabilizing member may be a bone plate 1402, the dynamic element may be a staple 1404, and the fasteners may be screws. Assembly 1400 is illustrated with locking screws 1406 on the left and non-locking screws 1408 on the right.

The bone plate 1402 has an obverse side 1412 and a reverse side 1414. The bone plate 1402 includes several holes 1416 which extend through the obverse and reverse sides 1412, 1414. Sixteen holes 1416 are illustrated, although any number of holes may be present. Each hole 1416 includes an internally threaded portion 1418 and a non-threaded portion 1420 so that each hole 1416 accepts either the locking screw 1406 or the non-locking screw 1408. The internally threaded portion 1418 engages external threads 1419 on the head 1407 of the locking screw 1406. The internally threaded portion 1418 may be adjacent to the reverse side 1414. The non-threaded portion 1420 engages the head 1409 of the non-locking screw 1408. The non-threaded portion 1420 may be adjacent to the obverse side 1412. The non-threaded portion 1420 may be concave and/or elongated. An optional groove 1422 in the obverse side 1412 extends along a line of six holes 1416 that extend along the midline of the plate 1402. Each of these six holes 1416 is also elongated, leaving webs 1424 extending between the second and third holes 1416 and the fourth and fifth holes 1416. No webs are shown between the first and second holes 1416, the third and fourth holes 1416, or the fifth and sixth holes 1416, although these webs may be present. The webs 1424 may be adjacent to the reverse side 1414. The webs 1424 separate the second and third holes 1416 and the fourth and fifth holes 1416, respectively, and may be present even if the holes 14416 are not elongated. The first and second holes 1416 are referred to collectively as a receiver 1426, and the involved holes 1416 are referred to as receiver holes 1428. A second receiver 1426 includes the third and fourth holes 1416, and a third receiver 1426 includes the fifth and sixth holes 1416.

The staple 1404 is described in at least one of the patent applications identified in this application. The staple 1404 may be the implant 200 of FIGS. 11 and 12, implant 300 of FIGS. 15A-16B, implant 600 of FIGS. 21 and 22, implant 800 of FIGS. 23A-24, or implant 2200 of FIGS. 78 and 79 of International Patent Application Serial No. PCT/US2015/039551; or implant 100 of FIGS. 1-3, staple 300 of FIGS. 4 and 5, staple 400 of FIG. 7, staple 480 of FIG. 8, or implant 2100 of FIGS. 10A and 10B of International Patent Application Serial No. PCT/US2015/039556. The illustrated staple 1404 is the implant 2200 of FIGS. 78 and 79 of International Patent Application Serial No. PCT/US2015/039551.

The staple 1404 includes a body 1440 or bridge, a first leg 1442, and a second leg 1444. The bridge extends between a first end 1446 and a second end 1448. The first leg 1442 is coupled to the first end 1446 and terminates in a first free end 1443. The second leg 1444 extends from the second end 1448 and terminates in a second free end 1445. A first projection 1450 extends from the first end 1446 and a second projection 1452 extends from the second end 1448.

The staple 1404 has an insertion state, or elastically deformed state, which is its shape under the influence of an external force, for example, an external force applied by a staple inserter tool. A first distance separates the free ends 1443, 1445 in the elastically deformed state. The staple 1404 also has a free state, or relaxed state, which is its shape when no external forces are acting upon the staple, other than gravity. A second distance separates the free ends 1443, 1445 in the relaxed state. The second distance is different from the first distance. In the example shown, the legs 1442, 1444 of the staple 1404 are parallel to one another in the elastically deformed state. However, the legs 1442, 1444 may converge or diverge in the elastically deformed state. In the example shown, the legs 1442, 1444 of the staple converge at their free ends 1443, 1445, or tips, in the relaxed state, so that the second distance is less than the first distance. However, the legs 1442, 1444 may diverge at their free ends 1443, 1445, or the legs 1442, 1444 may be parallel in the relaxed state. The staple 1404 assumes the elastically deformed state under the influence of an external force. The staple 1404 may resume the free state as soon as the external force is removed. If the legs 1442, 1444 of the staple 1404 are engaged in bone holes, then the staple may only be able to partially relax toward the free state due to the resistance of the bone. In this situation, the staple 1404 may be in a loaded state in between the elastically deformed state and the relaxed state. In this example, the staple 1404 is not locked to the bone plate 1402, although in other examples the staple is locked to the bone plate. In this example, the body 1440 of the staple 1404 rests within the receiver 1426, and the staple legs 1442, 1444 extend through the receiver holes 1428 and protrude from the reverse side 1414 of the bone plate 1402. The receiver 1426 holds the staple 1404 in a predetermined orientation and relative position with respect to the bone plate 1402. The receiver 1426 is one example of a group of features that function together to hold a staple a in a predetermined orientation and relative position with respect to a bone plate. Different features, or groups of features, may provide the same function. For example, the body 1440 of the staple 1404 may rest atop the obverse side 1412 of the bone plate 1402, or on a web, or the web 1424 may be replaced by ledges or other supports to serve as a stop or a docking point to prevent the body 1440 from passing through the reverse side 1414. Furthermore, the web 1424 may be replaced by one or more stop feature(s) or docking feature(s) on the staple 1404 instead of on the bone plate 1402. For example, the projections 1450, 1452 may serve as stop features or docking features.

The locking screw 1406 locks securely to any hole 1416 in the bone plate 1402. The locking screw 1406 may include an externally threaded head 1407 which locks to the hole 1416 in the bone plate 1402 when threaded tightly into the internally threaded portion 1418 of the hole 1416. The locking screw 1406 may be the design disclosed in at least one of the patent applications identified in this application. The locking screw 1406 may be the bone fixation device 390 of FIG. 11, bone fixation device 500 of FIGS. 24-26, bone fixation device 600 of FIGS. 27-30 of International Patent Application Serial No. PCT/US2014/070495.

The non-locking screw 1408 does not lock to the holes 1416 in the bone plate 1402. Instead, it remains free to rotate and translate within the confines of the screw hole 1416 after implantation. The non-locking screw 1408 may be polyaxially positionable relative to the screw hole 1416. The non-locking screw 1408 may include a head 1409 with an exterior surface that forms a ball-and-socket joint with the non-threaded portion 1420 of the hole 1416. The exterior surface may be convex, spherical, or conical.

The screws 1406 and 1408 are interchangeable in the screw holes 1416 of the bone plate 1402.

Figure 9A:
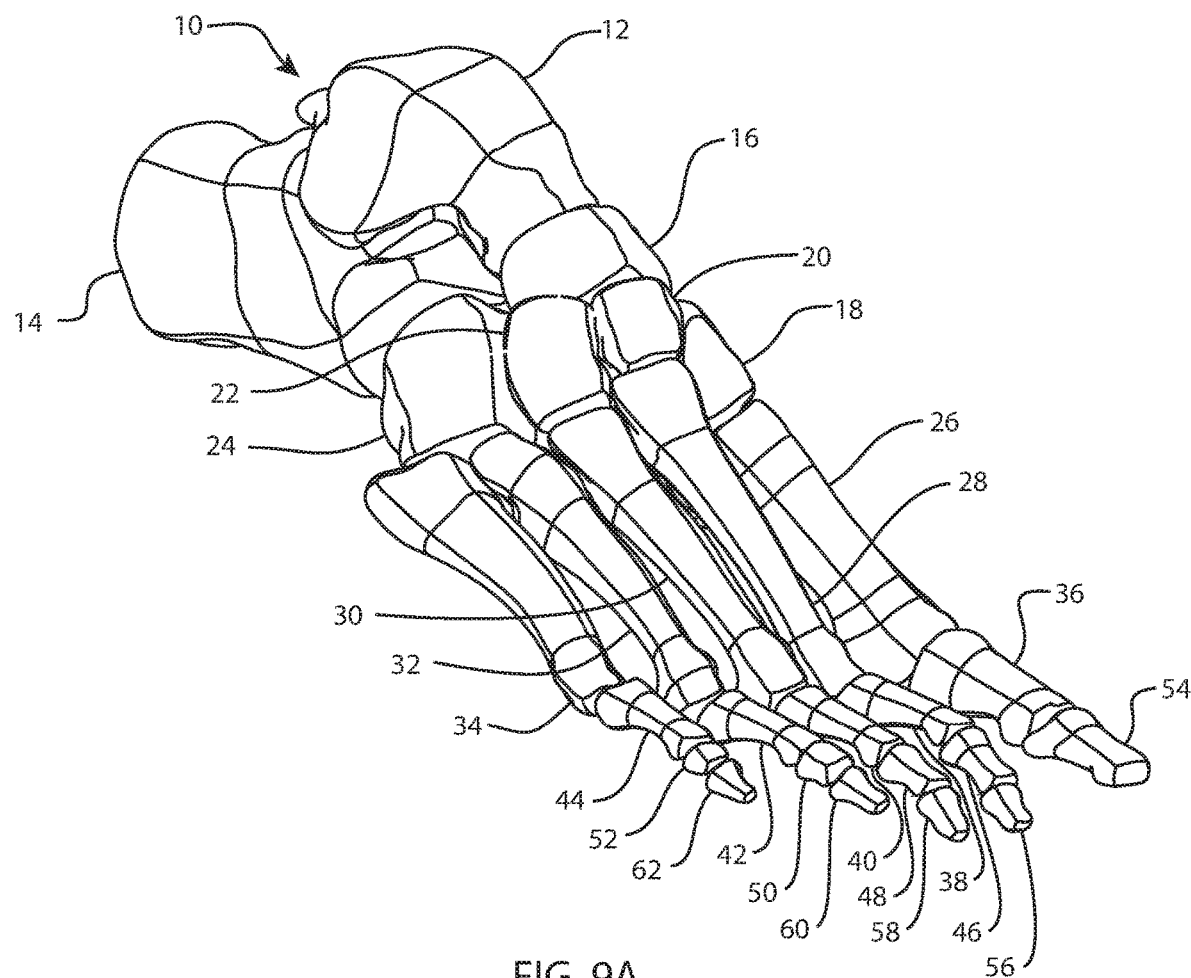
FIG. 9A is a lateral oblique view of the bones of a human right foot.
Figure 9B:
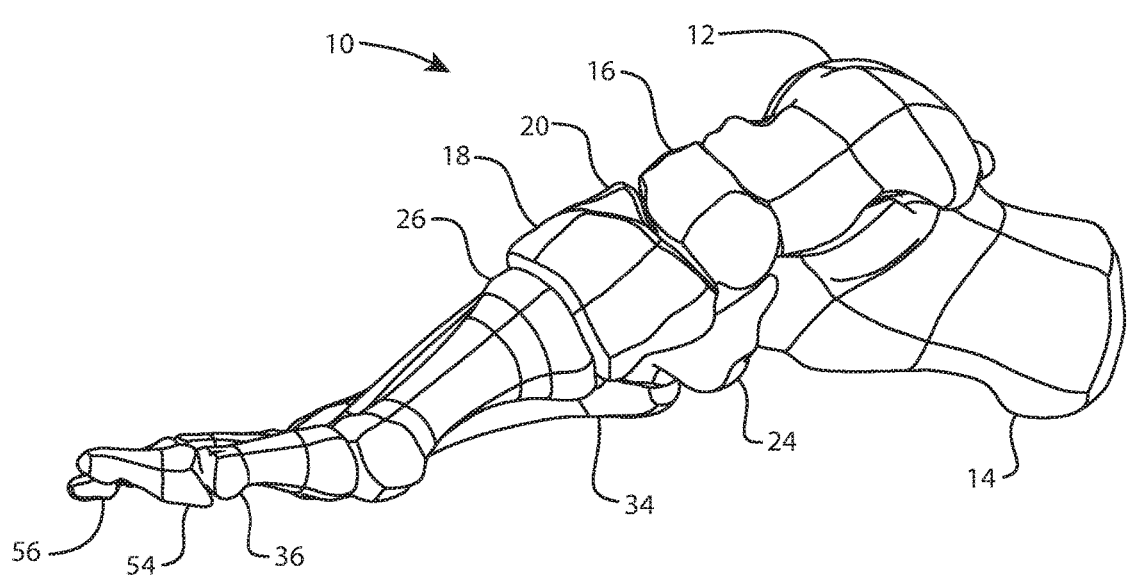
FIG. 9B is a medial view of the bones of a human right foot.

Referring to FIGS. 9A and 9B, a normal human foot 10 includes twenty-six bones, including a talus 12, a calcaneus 14, a navicular 16, a medial cuneiform 18, an intermediate cuneiform 20, a lateral cuneiform 22, a cuboid 24, a first metatarsal 26, a second metatarsal 28, a third metatarsal 30, a fourth metatarsal 32, a fifth metatarsal 34, a first proximal phalanx 36, a second proximal phalanx 38, a third proximal phalanx 40, a fourth proximal phalanx 42, a fifth proximal phalanx 44, a first middle phalanx 46, a second middle phalanx 48, a third middle phalanx 50, a fourth middle phalanx 52, a first distal phalanx 54, a second distal phalanx 56, a third distal phalanx 58, a fourth distal phalanx 60, and a fifth distal phalanx 62.

Figure 14:
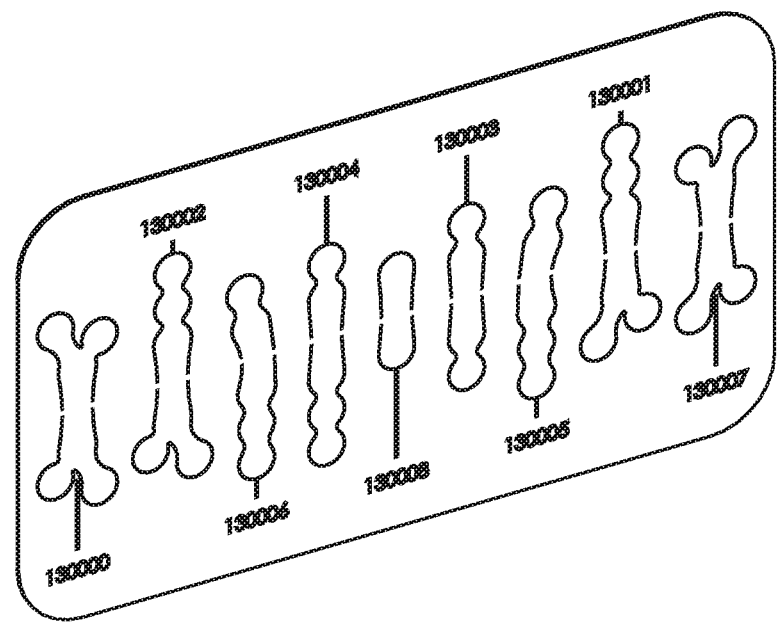
FIG. 14 is an oblique view of a kit of surgical instruments.
Figure 14:
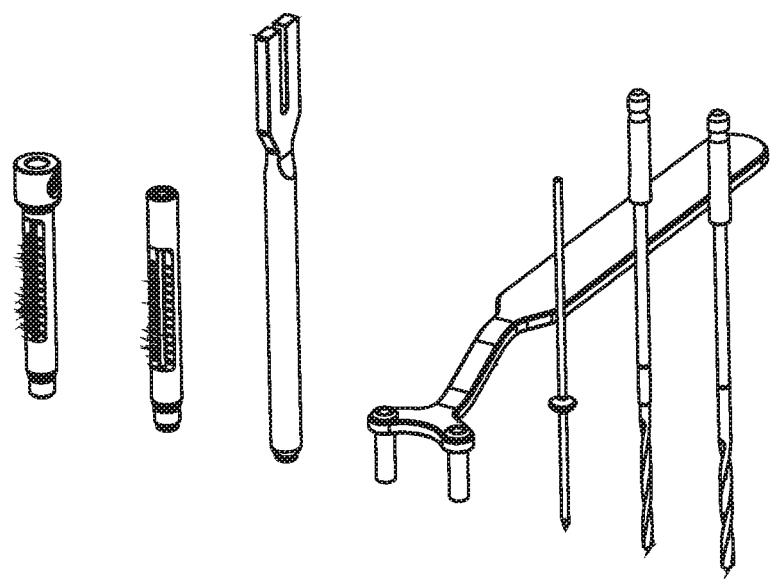

Referring to FIG. 14, several different surgical instruments may be provided in a kit or a set. From top to bottom, left to right, FIG. 14 illustrates a plate template, a threaded drill guide/depth gage, a polyaxial drill guide/depth gage, a bender/handle, a staple drill guide, an olive wire, drills (such as 2.0 mm and 2.5 mm diameters), and a self-retaining screwdriver (not shown) and a screwdriver handle, such as an AO quick connect handle (not shown).

Figure 15:
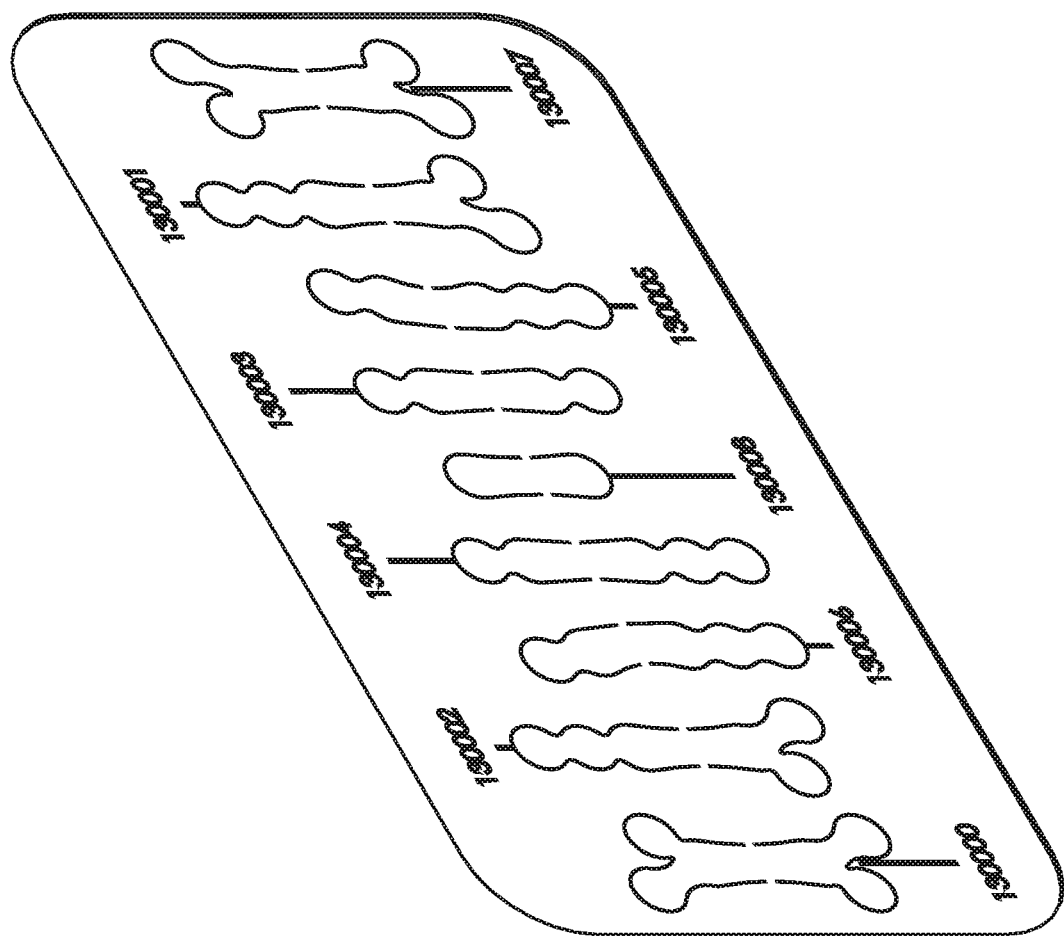
FIG. 15 is an oblique view of a sizing template of the kit of FIG. 14.

Referring to FIG. 15, a plate sizing template may include several individual templates for different plate shapes, each of which may be removed from, or "punched out" of, or torn away from the sizing template. The template may be provided sterile. Templating may be a step in a method for using the disclosed apparatus.

Figure 17A:
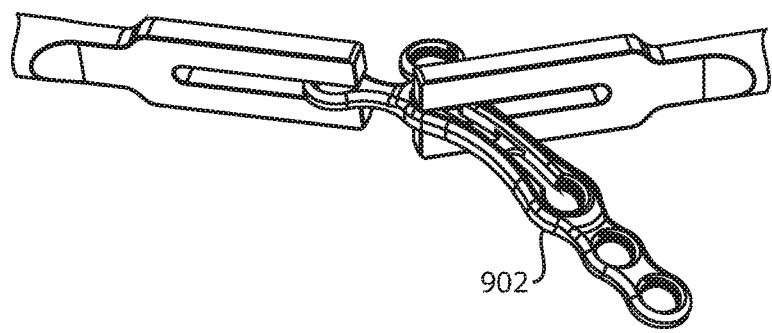
FIG. 17A is an oblique detail view of the plate and benders of FIG. 16A.
Figure 17B:
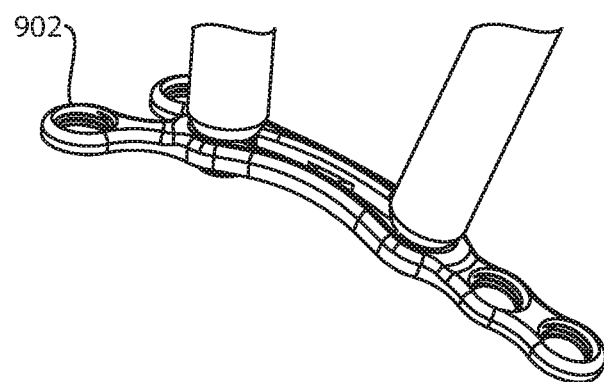
FIG. 17B is an oblique detail view of the plate and bender of FIG. 16B, with an additional bender.
Figure 17C:
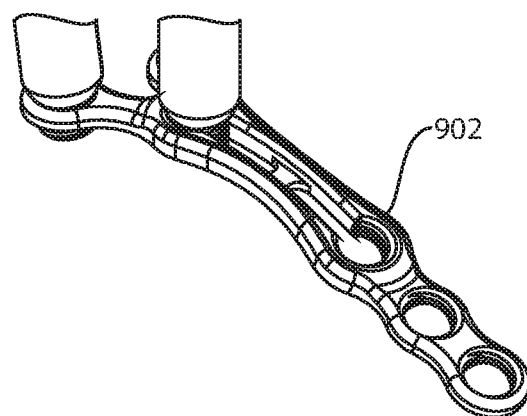
FIG. 17C is an oblique detail view of the plate and benders of FIG. 17B.

Referring to FIGS. 16A, 16B, and 17A-17C, a plate bender may include a threaded end and a forked end opposite the threaded end. The threaded end threads into the plate holes, as shown in FIGS. 17B and 17C. The forked end receives the plate, as shown in FIGS. 16A and 17A. The plate bender may also be used as a handle for the non-locking polyaxial drill guide (FIG. 20). Multiple plate benders may be provided in a kit or set of instruments. The plate bender(s) may be provided sterile. Plate bending or plate contouring may be a step in a method for using the disclosed apparatus. Plates may be bent in-situ or on a back table in an operating room.

Figure 18:
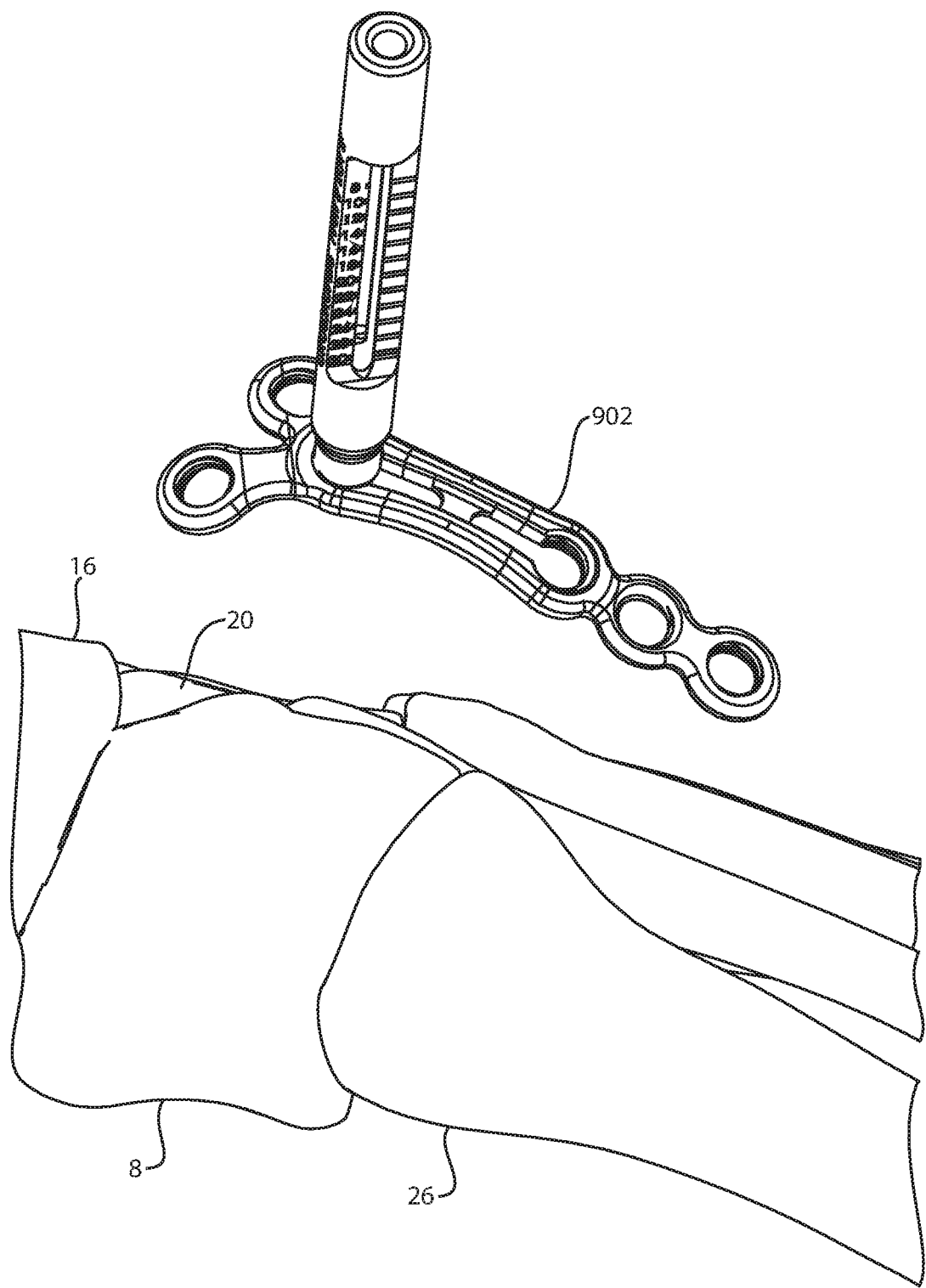
FIG. 18 is a medial oblique view of some of the bones of a human left foot, a bone plate, and a threaded drill guide of the kit of FIG. 14 which doubles as a plate inserter tool.

Referring to FIG. 18, a threaded drill guide may lock into a threaded hole in a bone plate, for example bone plate 902, to accurately guide a drill to make a hole in the bone to receive a locking screw 106. The threaded drill guide may also be used as a bone plate inserter instrument. Multiple threaded drill guides may be included in a kit or set of instruments. Inserting a bone plate may be a step in a method for using the disclosed apparatus.

Figure 19A:
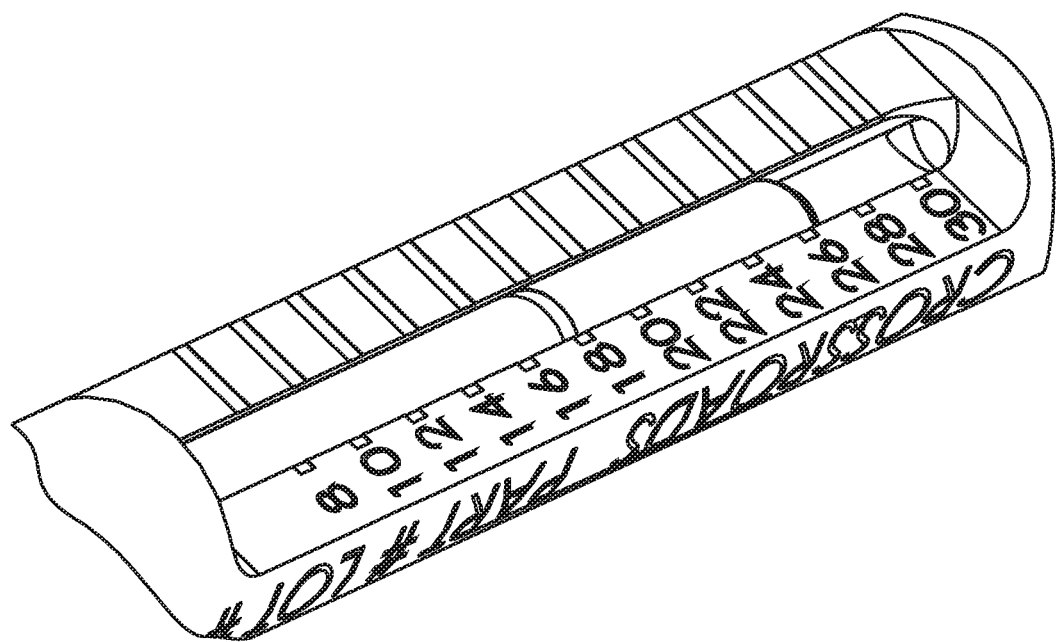
FIG. 19A is a detail view of a portion of the threaded drill guide of FIG. 18.
Figure 19B:
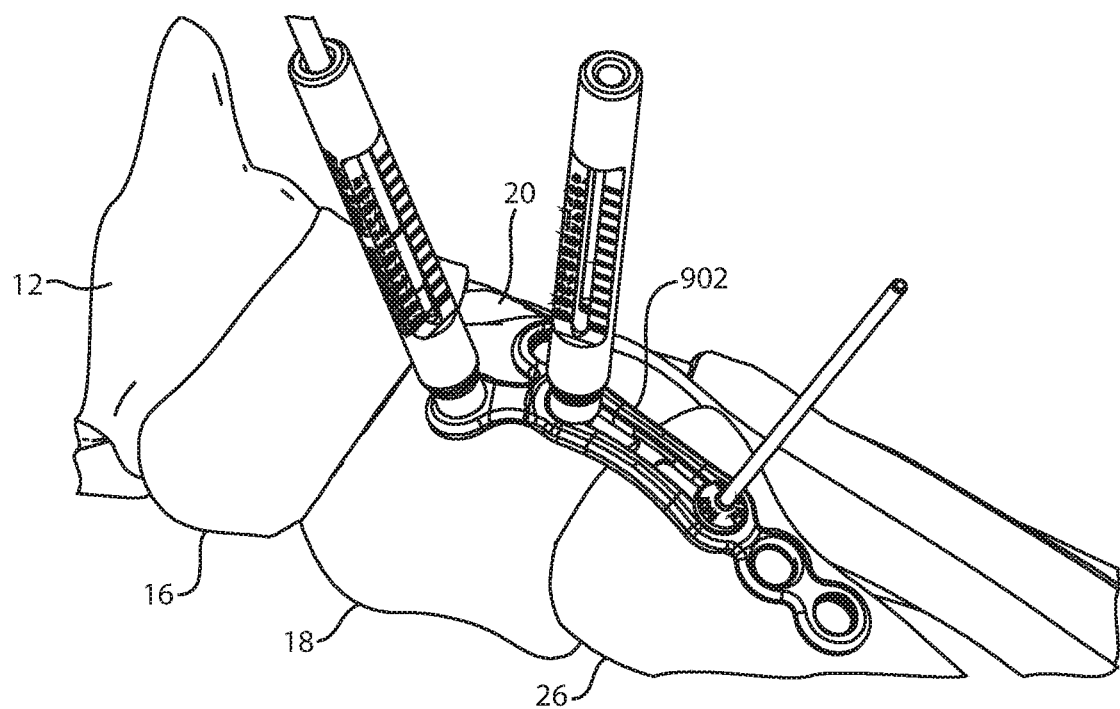
FIG. 19B is a medial oblique view of some of the bones of a human left foot, the bone plate of FIG. 18, two threaded drill guides of FIG. 18, and an olive wire of the kit of FIG. 14.

Referring to FIGS. 19A and 19B, an olive wire may be used for temporary fixation in a hole in a bone plate, for example bone plate 902. A laser mark on a drill may register with drill guide depth markings to indicate drilling depth (FIG. 19A). Drilling for a locking bone screw, and/or tapping for the locking bone screw, may be steps in a method for using the disclosed apparatus.

Figure 20A:
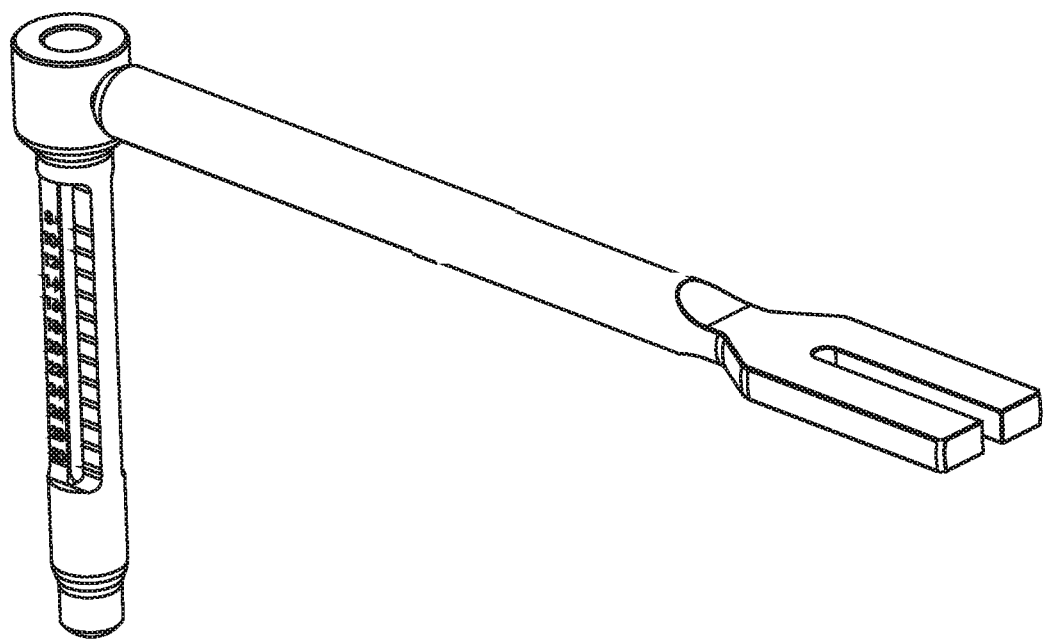
FIG. 20A is an oblique view of a non-locking polyaxial drill guide of the kit of FIG. 14 and a threaded plate bender of the kit of FIG. 14 which doubles as a handle for the non-locking polyaxial drill guide.
Figure 20B:
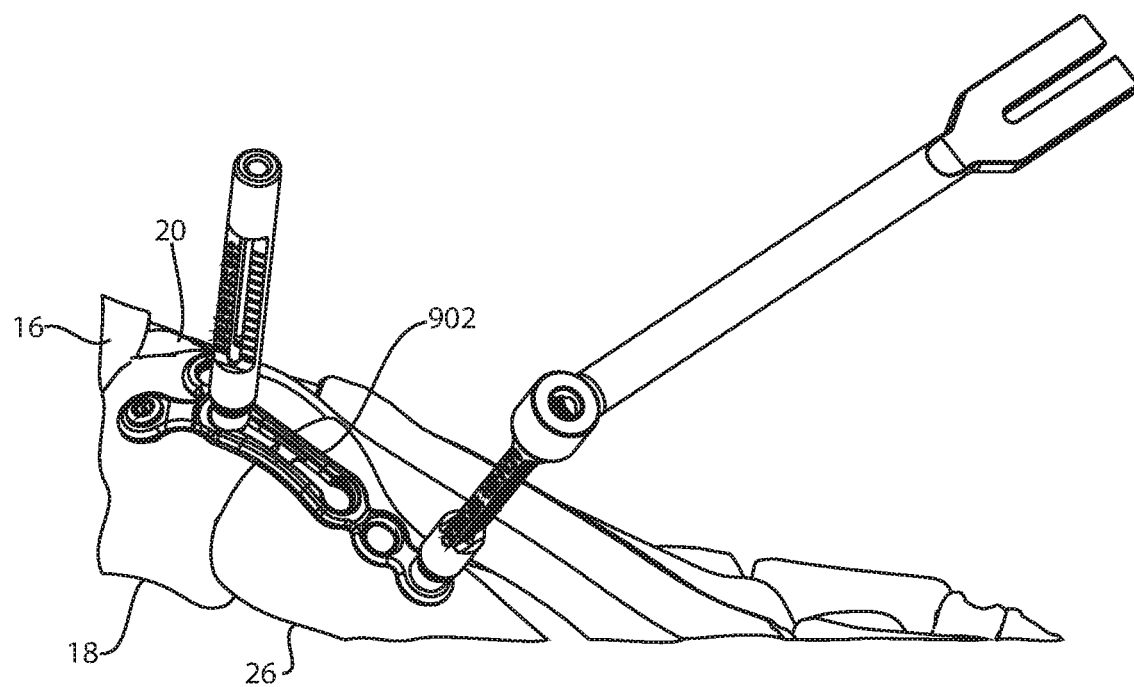
FIG. 20B is a medial oblique view of some of the bones of a human left foot, the bone plate and threaded drill guide of FIG. 18, and the non-locking polyaxial drill guide with threaded plate bender of FIG. 20A.

Referring to FIGS. 20A and 20B, a non-locking polyaxial drill guide may engage a hole in a bone plate, for example bone plate 902, to accurately guide a drill to make a hole in the bone to receive a non-locking screw 108. The plate bender may serve as a handle for the non-locking polyaxial drill guide (FIG. 20A). Drilling for a non-locking bone screw, and/or tapping for the non-locking bone screw, may be steps in a method for using the disclosed apparatus.

Figure 21:
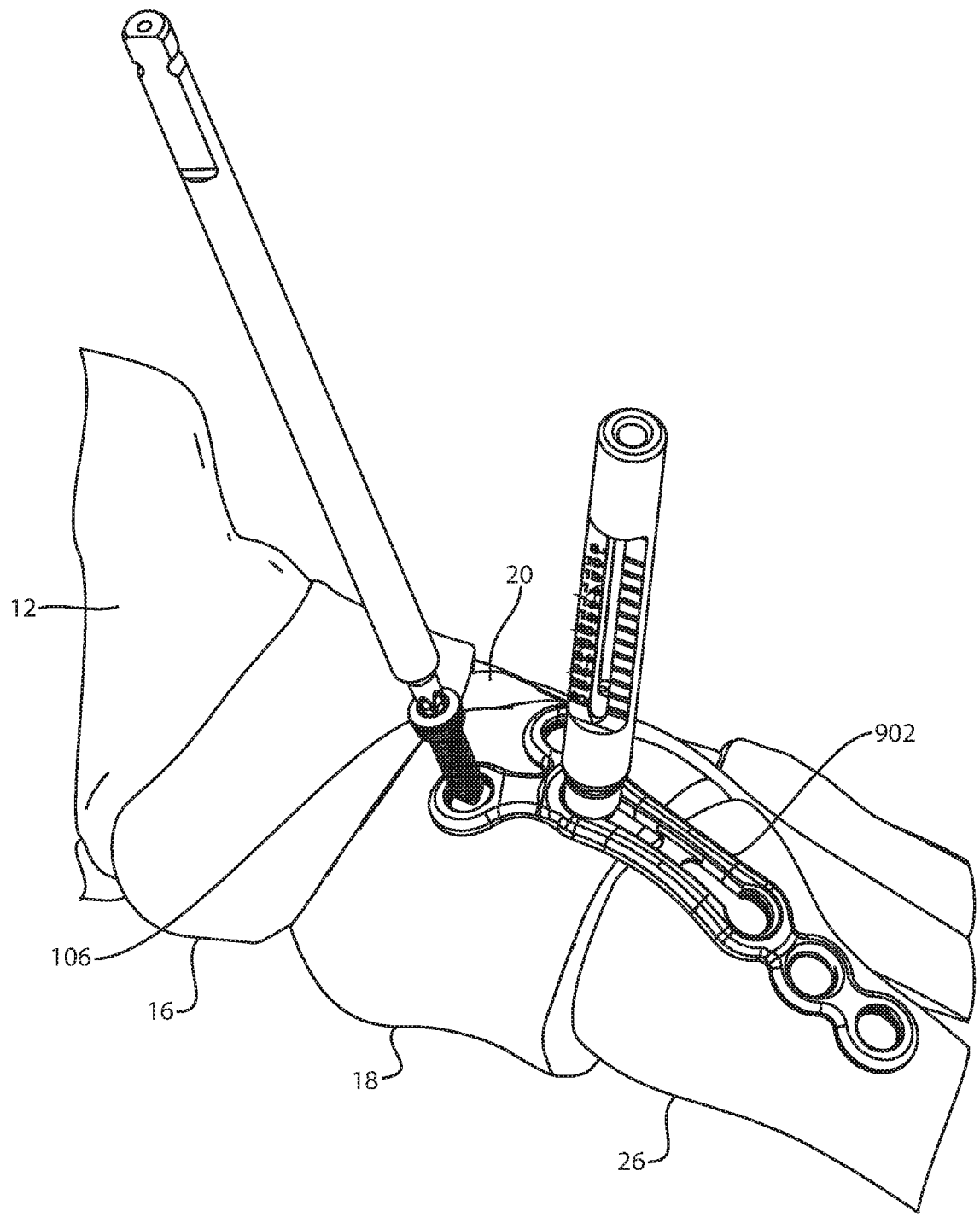
FIG. 21 is a medial oblique view of some of the bones of a human left foot, the bone plate and threaded drill guide of FIG. 18, the screw of FIG. 1A, and a screw driver of the kit of FIG. 14.

Referring to FIG. 21, locking or non-locking screws may be used interchangeably in the screw holes of the bone plates after bone holes are drilled. A screw driver instrument transmits torque from a manual or power source to the screw to drive the screw into the bone and, if a locking screw, into the screw hole threads of the bone plate. While FIG. 21 shows locking screws 106 placed proximally, but the procedure may progress from distal to proximal instead. Driving a screw into threaded engagement with the bone and, if a locking screw, with the screw hole threads of the bone plate, may be a step in a method for using the disclosed apparatus.

Figure 22A:
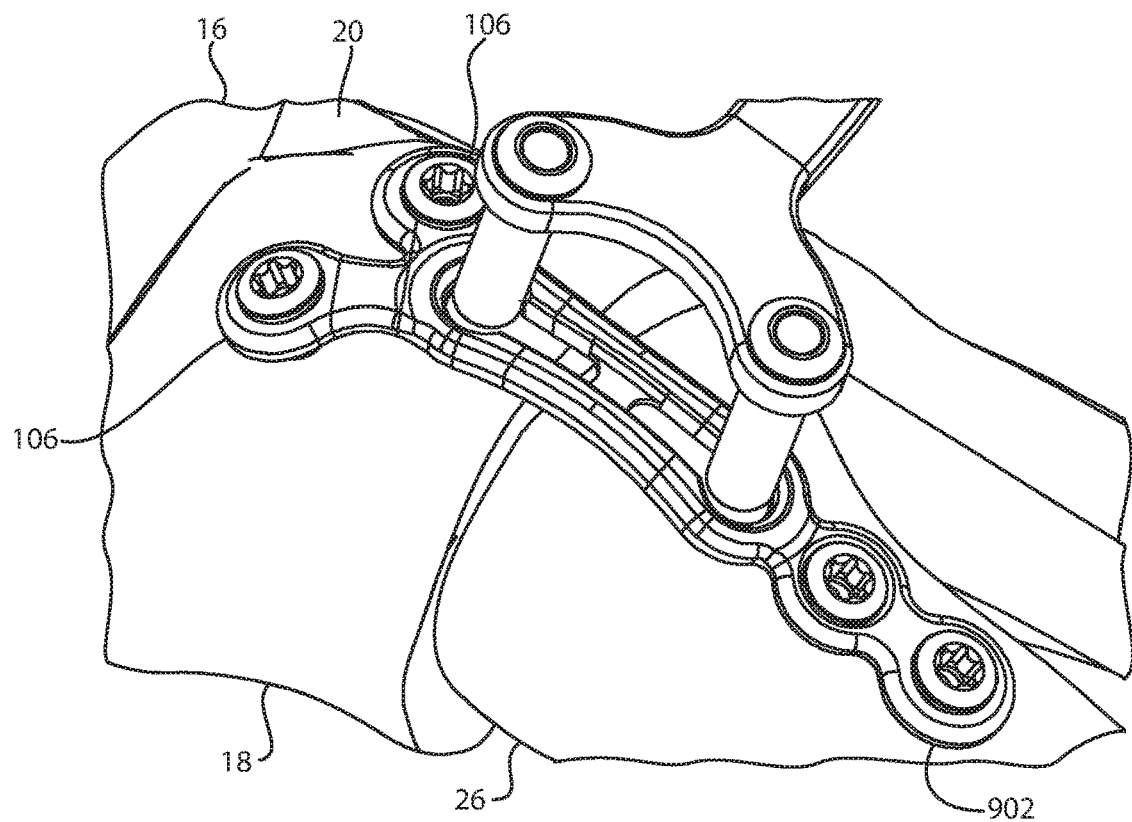
FIG. 22A is a medial oblique view of some of the bones of a human left foot, the bone plate of FIG. 18, the screws of FIG. 1A, and a staple drill guide of the kit of FIG. 14.
Figure 22B:
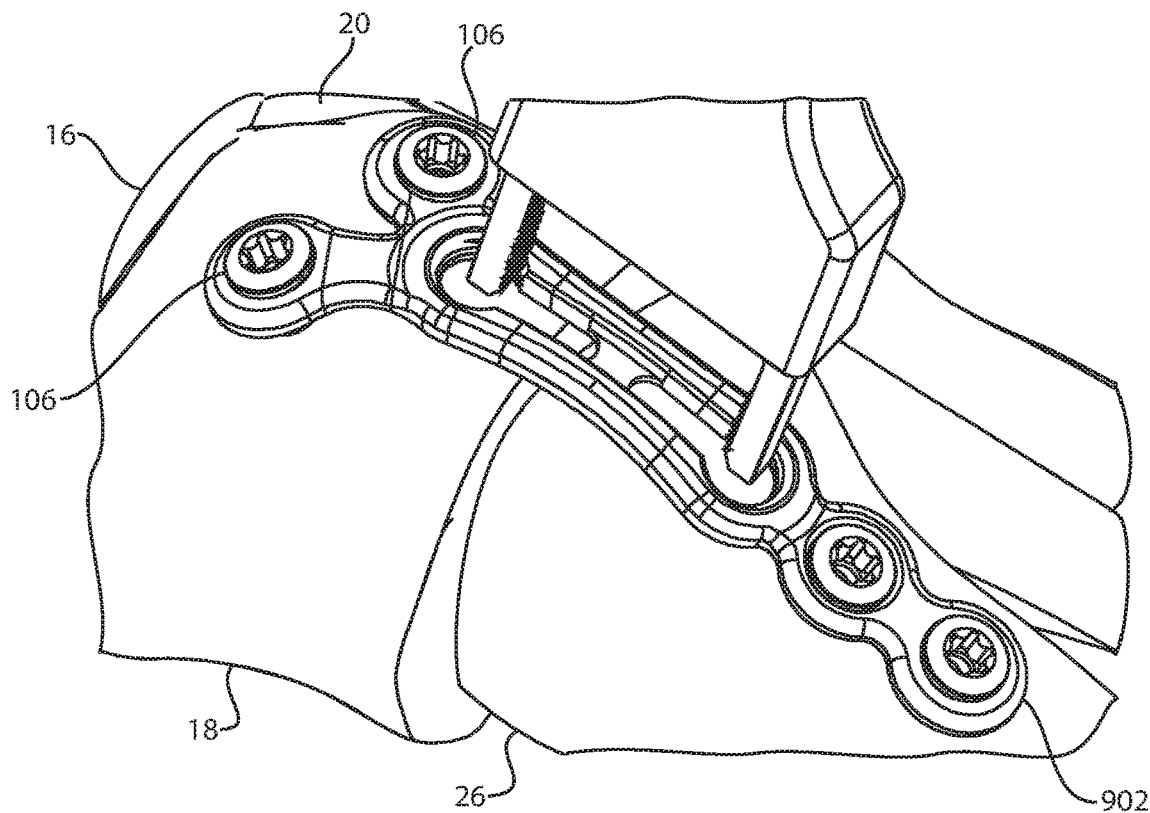
FIG. 22B is a medial oblique view of some of the bones of a human left foot, the bone plate of FIG. 18, the screws of FIG. 1A, and a staple inserter of the kit of FIG. 14.
Figure 22C:
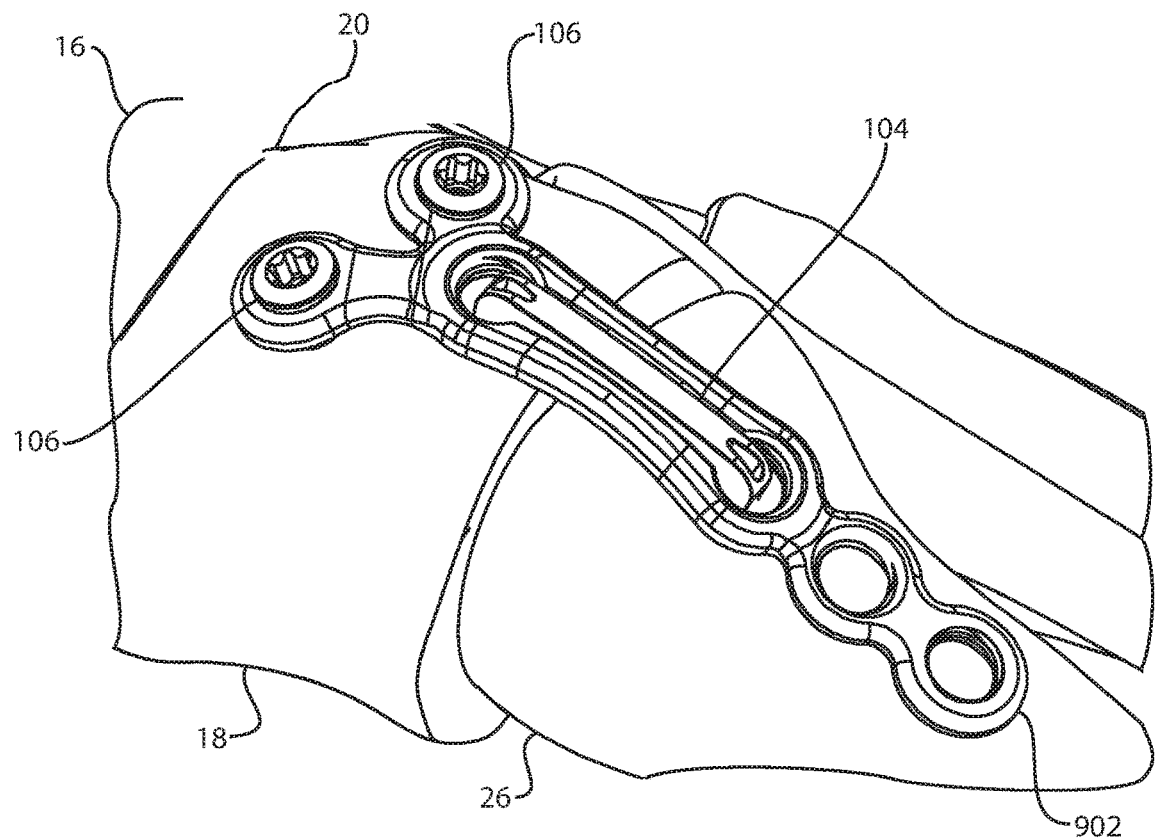
FIG. 22C is a medial oblique view of some of the bones of a human left foot, the bone plate of FIG. 18, the screws of FIG. 1A, and a staple.

Referring to FIGS. 22A-22C, a staple drill guide may engage a pair of holes in a bone plate, for example bone plate 902, to accurately guide a drill to make holes in the bone to receive a staple 104. Drilling for a staple may be a step in a method for using the disclosed apparatus. The step of drilling for the staple may occur after one end (proximal or distal) of the plate is secured to bone.

A staple inserter may hold the staple 104 for insertion (FIG. 22B). The staple inserter is described in at least one of the cross-referenced patent applications identified in paragraph [0001] of this application. For example, the staple 104 may be held with its legs forced into a parallel state for insertion. The staple inserter may engage the staple 104 strictly from a side of the staple opposite the side that faces the bone plate and bone portions, so that the staple 104 may be fully seated in the receiver while the staple inserter is attached to the staple 104. After the staple has been inserted through the bone plate, removing the staple inserter may allow the staple legs to relax and attempt to resume the free state, in which the staple legs are acutely angled with respect to each other (FIGS. 1A-1F). Inserting a staple may be a step in a method for using the disclosed apparatus.

FIG. 22C shows the bone plate 902 and the staple 104 extending across the first Lisfranc joint (or first tarsometatarsal joint) of a human left foot. The staple extends through holes in the bone plate 902 so that each staple leg is on a different side of the joint. As the staple relaxes after the staple inserter is removed, the staple legs apply mechanical load or stress across the joint. As the staple 104 relaxes towards its free state shown in FIGS. 1A-1F, the staple legs apply compressive load or stress across the joint. Conversely, a staple with divergent legs would apply tensile load or stress across the joint.

Figure 23:
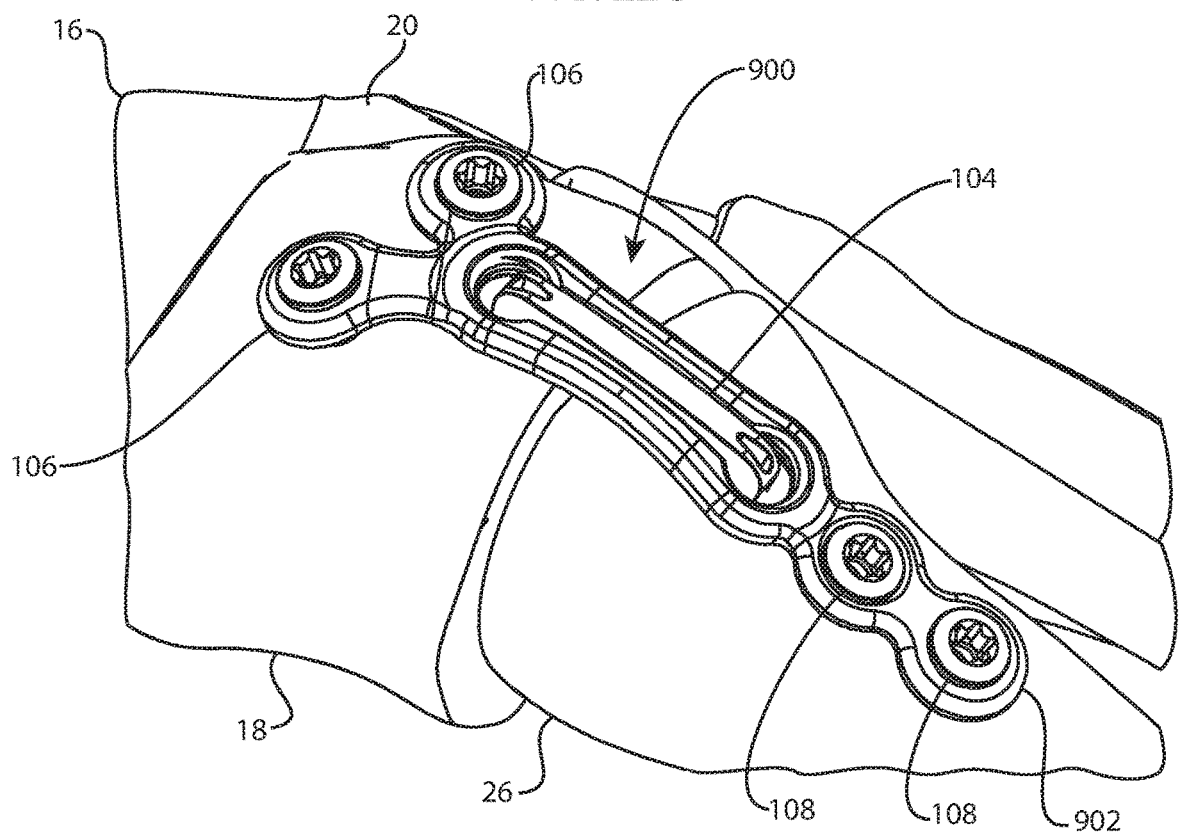
FIG. 23 is a medial oblique view of some of the bones of a human left foot, the bone plate of FIG. 18, the screws of FIG. 1A, and a staple.

Referring to FIG. 23, the bone plate 902, staple 104, locking screws 106, and non-locking screws 108 are shown in the final implanted state across the first Lisfranc joint. It may be particularly advantageous to use locking screws 106 adjacent to one leg of the staple 104, and non-locking screws 108 adjacent to the other leg of the staple 104. This is illustrated in FIG. 23, where locking screws 106 are used in the medial cuneiform 18 and non-locking screws 108 are used in the first metatarsal 26. However, an opposite arrangement is contemplated, with non-locking screws 108 are used in the medial cuneiform 18 and locking screws 106 are used in the first metatarsal 26.

Methods of using the disclosed apparatus may include any combination of the above mentioned steps, in any order.

One example of a method of using the disclosed apparatus includes the steps of: inserting a bone plate adjacent to a first bone portion and a second bone portion, wherein a discontinuity separates the second bone portion from the first bone portion, wherein the bone plate extends across the discontinuity, wherein the bone plate includes at least four holes; locking a threaded drill guide to a first hole through the bone plate, wherein the first hole of the bone plate is adjacent to the first bone portion; drilling a first bone hole through the threaded drill guide into the first bone portion; driving a locking screw through the first hole of the bone plate into threaded engagement with the first bone hole and the first hole of the bone plate; engaging a staple drill guide with a second hole through the bone plate and a third hole through the bone plate, wherein the second hole of the bone plate is adjacent to the first bone portion, wherein the third hole of the bone plate is adjacent to the second bone portion; drilling a second bone hole through the staple drill guide into the first bone portion; drilling a third bone hole through the staple drill guide into the second bone portion; inserting a first leg of a staple through the second hole of the bone plate into engagement with the second bone hole and inserting a second leg of the staple through the third hole of the bone plate into engagement with the third bone hole, wherein the first leg of the staple is parallel to the second leg of the staple while the staple is inserted, wherein the first and second legs of the staple compress towards each other after the staple is inserted; engaging a non-locking polyaxial drill guide with a fourth hole through the bone plate, wherein the fourth hole of the bone plate is adjacent to the second bone portion; drilling a fourth bone hole through the non-locking polyaxial drill guide into the second bone portion; and driving a non-locking screw through the fourth hole of the bone plate into threaded engagement with the fourth bone hole and non-locking engagement with the fourth hole of the bone plate.

The preceding method may also include the step of securing the staple to the bone plate. The staple may be secured to the bone plate with a set screw, a ductile tab, or a snap fit. The staple may be secured to the bone plate by a portion of the staple being molded within a portion of the bone plate. The staple may be secured to the bone plate by being integrally formed with the bone plate.

Another example of a method of using the disclosed apparatus includes the steps of: inserting a bone plate adjacent to a first bone portion and a second bone portion, wherein a discontinuity separates the second bone portion from the first bone portion, wherein the bone plate extends across the discontinuity; drilling a first bone hole through a first hole through the bone plate into the first bone portion; drilling a second bone hole through a second hole through the bone plate into the second bone portion; inserting a leg of a first elbow peg through the first hole of the bone plate into engagement with the first bone hole and placing a head of the first elbow peg adjacent to the first hole of the bone plate; inserting a leg of a second elbow peg through the second hole of the bone plate into engagement with the second bone hole and placing a head of the second elbow peg adjacent to the second hole of the bone plate; driving a first bone screw through an aperture through the head of the first elbow peg and the first hole of the bone plate into threaded engagement with the first bone portion beside the leg of the first elbow peg; and driving a second bone screw through an aperture through the head of the second elbow peg and the second hole of the bone plate into threaded engagement with the second bone portion beside the leg of the second elbow peg.

Yet another example of a method of using the disclosed apparatus includes the steps of: inserting a bone plate adjacent to a first bone portion and a second bone portion, wherein a discontinuity separates the second bone portion from the first bone portion, wherein the bone plate extends across the discontinuity; drilling a first bone hole through a first hole through the bone plate into the first bone portion; drilling a second bone hole through a second hole through the bone plate into the second bone portion; inserting a leg of a first elbow peg through the first hole of the bone plate into engagement with the first bone hole and placing a head of the first elbow peg over the first hole of the bone plate; inserting a leg of a second elbow peg through the second hole of the bone plate into engagement with the second bone hole and placing a head of the second elbow peg over the second hole of the bone plate; tightening a first set screw against the head of the first elbow peg; and tightening a second set screw against the head of the second elbow peg.

Yet another example of a method of using the disclosed apparatus includes the steps of: inserting a bone plate adjacent to a first bone portion and a second bone portion, wherein a discontinuity separates the second bone portion from the first bone portion, wherein the bone plate extends across the discontinuity; drilling a first bone hole through a first hole through the bone plate into the first bone portion; drilling a second bone hole through a second hole through the bone plate into the second bone portion; inserting a leg of a first straight peg through the first hole of the bone plate into engagement with the first bone hole and placing a head of the first straight peg in the first hole of the bone plate; inserting a leg of a second straight peg through the second hole of the bone plate into engagement with the second bone hole and placing a head of the second straight peg in the second hole of the bone plate; tightening a first set screw against the head of the first straight peg; and tightening a second set screw against the head of the second straight peg.

The preceding method may also include the step of rotating the first and/or second straight pegs to position the leg(s) in desired orientation(s) relative to the bone plate before tightening the set screws.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

What is claimed is:

1. A bone fixation system, comprising:
    a bone fixation device comprising:
        a stabilizing body comprising:
            an obverse side;
            a reverse side opposite the obverse side; and
            a plurality of fastener openings extending through the obverse side and the reverse side; and
        a first leg integrally formed with the stabilizing body and extending from the reverse side of the stabilizing body to a first free end; and
        a second leg integrally formed with the stabilizing body and extending from the reverse side of the stabilizing body to a second free end;
        wherein the first free end is separated from the second free end by a first distance when bone fixation device is in an elastically deformed state;
        wherein the first free end is separated from the second free end by a second distance when the bone fixation device is in a relaxed state, the first distance being different than the second distance such that the bone fixation device provides a force at the first and second free ends when the bone fixation devices is in the elastically deformed state;
        wherein a longitudinal axis of the first leg and a longitudinal axis of the second leg are configured to converge when the bone fixation device is in the relaxed state; and
        wherein at least a portion of the stabilizing body between the first leg and the second leg is configured to deform when the bone fixation device transitions from the elastically deformed state to the relaxed state; and
    a plurality of fasteners configured to be positioned within the one or more fasteners openings of the stabilizing body and to extend through the stabilizing body.

2. The bone fixation system of claim 1, wherein the first distance is greater than the second distance such that the bone fixation device provides a compressive force between the first and second free ends when the bone fixation devices is in an elastically deformed state.

3. The bone fixation system of claim 1, wherein at least a portion of the bone fixation device is formed of a superelastic material.

4. The bone fixation system of claim 3, wherein at least a portion of the bone fixation device is formed of nitinol.

5. The bone fixation system of claim 1, wherein the plurality of fasteners comprises a plurality of bone screws.

6. The bone fixation system of claim 1, wherein the plurality of fasteners are configured to rotate and translate within the plurality of fastener openings.

7. The bone fixation system of claim 1, wherein the plurality of fasteners are polyaxially positionable relative to the plurality of fastener openings.

8. The system of claim 1, wherein the plurality of fastener openings comprise a first fastener opening and a second fastener opening.

9. The system of claim 8, wherein the first leg extends from the stabilizing body at a first location and the second leg extends from the stabilizing body at a second location, the first location being separated from the second location by a third distance; and
    wherein the first fastener opening is separated from the second fastener opening by a fourth distance, the fourth distance being greater than the third distance.

10. The system of claim 8, wherein the first fastener opening and the second fastener opening are positioned along a longitudinal axis of the stabilizing body.

11. The system of claim 10, wherein the first leg extends from the stabilizing body at a position between the first fastener opening and the second fastener opening relative to the longitudinal axis.

12. The system of claim 11, wherein the second leg extends from the stabilizing body at a position between the first fastener opening and the second fastener opening relative to the longitudinal axis.

13. The system of claim 12, wherein first leg and the second leg extend from the stabilizing body along the longitudinal axis.

14. The system of claim 8, wherein at least one of the first fastener opening and the second fastener opening is positioned lateral to a longitudinal axis of the stabilizing body.

15. The system of claim 8, further comprising a third fastener opening.

16. The system of claim 1, wherein the first leg and the second leg are substantially parallel in the elastically deformed state.

17. The system of claim 1, wherein the stabilizing body comprises a bone plate.

18. The system of claim 17, wherein the first leg and the second leg are part of a staple integrally formed with the bone plate.

19. The system of 18, wherein the staple comprises a bridge extending between the first leg and the second leg.

* * * * *